(12) United States Patent
Hsieh-Wilson et al.

(10) Patent No.: US 9,766,245 B2
(45) Date of Patent: Sep. 19, 2017

(54) METHOD OF DETECTING CANCER BASED ON GLYCAN BIOMARKERS

(71) Applicant: California Institute of Technology, Pasadena, CA (US)

(72) Inventors: Linda C. Hsieh-Wilson, South Pasadena, CA (US); Wen Yi, Hangzhou (CH); Jean-Luc Chaubard, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 156 days.

(21) Appl. No.: 14/147,446

(22) Filed: Jan. 3, 2014

(65) Prior Publication Data

US 2014/0323699 A1    Oct. 30, 2014

Related U.S. Application Data

(60) Provisional application No. 61/748,895, filed on Jan. 4, 2013.

(51) Int. Cl.
| | | |
|---|---|---|
| *C07H 7/02* | (2006.01) | |
| *C07H 5/04* | (2006.01) | |
| *C12P 19/18* | (2006.01) | |
| *G01N 33/574* | (2006.01) | |
| *G01N 33/533* | (2006.01) | |

(52) U.S. Cl.
CPC ......... *G01N 33/57492* (2013.01); *C07H 5/04* (2013.01); *C07H 7/02* (2013.01); *C12P 19/18* (2013.01); *G01N 33/533* (2013.01); *G01N 33/57469* (2013.01); *G01N 2400/02* (2013.01)

(58) Field of Classification Search
CPC .............. C07H 5/04; C07H 7/02; C12P 19/18
See application file for complete search history.

(56) References Cited

U.S. PATENT DOCUMENTS

2005/0130235 A1*  6/2005  Hsieh-Wilson ........ C07H 19/10
                                                              435/7.5

OTHER PUBLICATIONS

Chaubard et al., J. Am. Chem. Soc., 2012, 134(10), p. 4489-4492 and supporting information p. S1-S22.*
Zheng et al., J. Am. Chem. Soc., 2005, 127, p. 9982-9983.*
Harris et al., eds., Advances in Human Genetics 10, 1980, Springer US, p. 1-136.*
Becker, et al. "Fucose: biosynthesis and biological function in mammals." Glycobiology (2003) 13 (7): 41R-53R. doi: 10.1093/glycob/cwg054.
Blixt, et al. Glycan microarrays for screening sialyltransferase specificities. Glycoconj J. Jan. 2008;25(1):59-68. Epub Oct. 4, 2007.
Blixt, et al. Printed covalent glycan array for ligand profiling of diverse glycan binding proteins. Proc Natl Acad Sci U S A. Dec. 7, 2004;101(49):17033-17038. Epub Nov. 24, 2004.
Chang, et al. Expression of Globo H and SSEA3 in breast cancer stem cells and the involvement of fucosyl transferases 1 and 2 in Globo H synthesis. Proc Natl Acad Sci U S A. Aug. 19, 2008;105(33):11667-11672. doi: 10.1073/pnas.0804979105. Epub Aug. 6, 2008.
Chang, et al. Rapid characterization of sugar-binding specificity by in-solution proximity binding with photosensitizers. Glycobiology. Jul. 2011;21(7):895-902. doi: 10.1093/glycob/cwr021. Epub Feb. 16, 2011.
Chen, et al. Advances of Olefin Polymerization in Aqueous Solutions. Progress in Chemisty. 2003; 15(5):401-408. (in Chinese with English abstract).
Clark, et al. Direct in-gel fluorescence detection and cellular imaging of O-GlcNAc-modified proteins. J Am Chem Soc. Sep. 3, 2008;130(35):11576-11577. doi: 10.1021/ja8030467. Epub Aug. 7, 2008.
Coats, et al. Trimethylsilyl-directed 1,3-dipolar cycloaddition reactions in the solid-phase synthesis of 1,2,3-triazoles. Org Lett. Apr. 14, 2005;7(8):1469-72.
Colnaghi, et al. A multiparametric study by monoclonal antibodies in breast cancer. In: R.L. Ceriani (ed.) Immunological approaches to the diagnosis and therapy of breast cancer. pp. 21-32, Plenum Publishing Corp., 1987.
Cornish, et al. Site-Specific Protein Modification Using a Ketone Handle. J. Am. Chem. Soc. 1996; 118(34):8150-8151.
Delves. The role of glycosylation in autoimmune disease. Autoimmunity. 1998;27(4):239-53.
Gama, et al. Sulfation patterns of glycosaminoglycans encode molecular recognition and activity. Nat Chem Biol. Sep. 2006;2(9):467-73. Epub Jul. 30, 2006.
Geoghegan, et al. Site-directed conjugation of nonpeptide groups to peptides and proteins via periodate oxidation of a 2-amino alcohol. Application to modification at N-terminal serine. Bioconjug Chem. Mar.-Apr. 1992;3(2):138-46.
Gololobov. Recent advances in the staudinger reaction. 1992; 48(8):1353-1406.
Gololobov, et al. Sixty years of staudinger reaction. Tetrahedron. 1981; 37(3):437-472.
Hang, et al. Ketone isosteres of 2-N-acetamidosugars as substrates for metabolic cell surface engineering. J Am Chem Soc. Feb. 14, 2001;123(6):1242-3.
Huisgen, Rolf. 1,3-Dipolar Cycloaddition Chemistry. Ed. Padwa, A., Wiley, New York. 1984; p. 1-176.
Jencks. Studies on the Mechanism of Oxime and Semicarbazone Formation. J. Am. Chem. Soc. 1959; 81(2): 475-481.
Jewett, et al. Cu-free click cycloaddition reactions in chemical biology. Chem Soc Rev. Apr. 2010;39(4):1272-9.
Khidekel, et al. A Chemoenzymatic Approach toward the Rapid and Sensitive Detection of O-GlcNAc Posttranslational Modifications. J. Am. Chem. Soc. 2003; 125(52):16162-16163.
Kim, et al. Perspectives on the significance of altered glycosylation of glycoproteins in cancer. Glycoconj J. Aug. 1997;14(5):569-76.

(Continued)

*Primary Examiner* — Jonathan S Lau
(74) *Attorney, Agent, or Firm* — Wilson Sonsini Goodrich & Rosati

(57) ABSTRACT

The present invention provides a method for labeling or detecting a protein with certain glycosyl groups. The methods are particularly useful for detecting cancer cells comprising the detected glycosyl groups. The present invention further provides labeling agents and detection agents, labeled proteins and mixtures, and kits and arrays thereof.

12 Claims, 14 Drawing Sheets

(56) References Cited

OTHER PUBLICATIONS

Lee, et al. Expression of blood-group antigen A—a favorable prognostic factor in non-small-cell lung cancer. N Engl J Med. Apr. 18, 1991;324(16):1084-90.
Lewis, et al. Click chemistry in situ: acetylcholinesterase as a reaction vessel for the selective assembly of a femtomolar inhibitor from an array of building blocks. Angew Chem Int Ed Engl. Mar. 15, 2002;41(6):1053-7.
Li, et al. 1,3-Dipolar cycloaddition of azides with electron-deficient alkynes under mild condition in water. Tetrahedron Letters. 2004; 45(15):3143-3146.
Liang, et al. Glycan array: a powerful tool for glycomics studies. Expert Rev Proteomics. Dec. 2009;6(6):631-45. doi: 10.1586/epr. 09.82.
Lynn, et al. Water-Soluble Ruthenium Alkylidenes: Synthesis, Characterization, and Application to Olefin Metathesis in Protic Solvents. J. Am. Chem. Soc. 2000; 122(28):6601-6609.
Mahal, et al. Engineering chemical reactivity on cell surfaces through oligosaccharide biosynthesis. Science. May 16, 1997;276(5315):1125-8.
Manimala, et al. High-throughput carbohydrate microarray analysis of 24 lectins.Angew. Chem. 2006;118:3689-3692.
Manimala, et al. High-throughput carbohydrate microarray profiling of 27 antibodies demonstrates widespread specificity problems. Glycobiology. Aug. 2007;17(8):17C-23C. Epub May 4, 2007.
McCabe, et al. "Passive avoidance training increases fucose incorporation into glycoproteins in chick forebrain slices in vitro." Neurochemical research 10.8 (1985): 1083-1095.
Menard, et al. Generation of monoclonal antibodies reacting with normal and cancer cells of human breast. Cancer Res. Mar. 1983;43(3):1295-300.
Miyake, et al. Correlation of expression of H/Le(y)/Le(b) antigens with survival in patients with carcinoma of the lung. N Engl J Med. Jul. 2, 1992;327(1):14-8.
Murrey, et al. Identification of the plasticity-relevant fucose-alpha(1-2)-galactose proteome from the mouse olfactory bulb. Biochemistry. Aug. 4, 2009;48(30):7261-70. doi: 10.1021/bi900640x.
Murrey, et al. Protein fucosylation regulates synapsin Ia/Ib expression and neuronal morphology in primary hippocampal neurons. Proc Natl Acad Sci U S A. Jan. 3, 2006;103(1):21-6. Epub Dec. 22, 2006.
Padwa. Comprehensive Organic Synthesis, vol. 4, (1991) Ed. Trost, B. M., Pergamon, Oxford, p. 1069-1109.
Peracaula, et al. Altered glycosylation pattern allows the distinction between prostate-specific antigen (PSA) from normal and tumor origins. Glycobiology. Jun. 2003;13(6):457-70. Epub Jan. 3, 2003.
Pohle, et al. "Incorporation of [3H]fucose in rat hippocampal structures after conditioning by perforant path stimulation and after LTP-producing tetanization." Brain research 1987; 410(2): 245-56.
Rexach, et al. Chemical approaches to understanding O-GlcNAc glycosylation in the brain. Nat Chem Biol. Feb. 2008;4(2):97-106. doi: 10.1038/nchembio.68.
Rexach, et al. Quantification of O-glycosylation stoichiometry and dynamics using resolvable mass tags. Nat Chem Biol. Sep. 2010;6(9):645-51. doi: 10.1038/nchembio.412. Epub Jul. 25, 2010.
Rostovtsev, et al. A stepwise huisgen cycloaddition process: copper(I)-catalyzed regioselective "ligation" of azides and terminal alkynes. Angew Chem Int Ed Engl. Jul. 15, 2002;41(14):2596-9.
Saxon, et al. Investigating cellular metabolism of synthetic azidosugars with the Staudinger ligation. J Am Chem Soc. Dec. 18, 2002;124(50):14893-902.
Schroder, et al. Screening and prostate-cancer mortality in a randomized European study. N Engl J Med. Mar. 26, 2009;360(13):1320-8. doi: 10.1056/NEJMoa0810084. Epub Mar. 18, 2009.
Seo, et al. Click chemistry to construct fluorescent oligonucleotides for DNA sequencing. J Org Chem. Jan. 24, 2003;68(2):609-12.
Shao, et al. Unprotected Peptides as Building Blocks for the Synthesis of Peptide Dendrimers with Oxime, Hydrazone, and Thiazolidine Linkages. J. Am. Chem. Soc. 1995; 117(14):3893-3899.
Shipp, et al. Profiling the sulfation specificities of glycosaminoglycan interactions with growth factors and chemotactic proteins using microarrays. Chem Biol. Feb. 2007;14(2):195-208.
Smith, et al. Use of glycan microarrays to explore specificity of glycan-binding proteins. Methods Enzymol. 2010;480:417-44. doi: 10.1016/S0076-6879(10)80033-3.
Tiunova, et al. "Two critical periods of protein and glycoprotein synthesis in memory consolidation for visual categorization learning in chicks," doi: 10.1101/lm. *Learning & Memory* 4.5 (1998): 401-410.
Tornoe, et al. Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.
Tully, et al. Discovery of a TNF-alpha antagonist using chondroitin sulfate microarrays. J Am Chem Soc. Jun. 21, 2006;128(24):7740-1.
Yi, et al. Bacterial homologue of human blood group A transferase. J Am Chem Soc. Nov. 5, 2008;130(44):14420-1. doi: 10.1021/ja805844y. Epub Oct. 9, 2008.
Zhang, et al. Selection of tumor antigens as targets for immune attack using immunohistochemistry: protein antigens. Clin Cancer Res. Nov. 1998;4(11):2669-76.
Zheng, et al. Tracking N-acetyllactosamine on cell-surface glycans in vivo. Angew Chem Int Ed Engl. Apr. 26, 2011;50(18):4113-8. doi: 10.1002/anie.201100265. Epub Mar. 29, 2011.

* cited by examiner

METHOD OF DETECTING CANCER BASED ON GLYCAN BIOMARKERS

CROSS-REFERENCE

This application claims the benefit under 35 USC §119(e) of U.S. Provisional Application No. 61/748,895, filed on Jan. 4, 2013, which application is incorporated herein by reference in its entirety.

STATEMENT AS TO FEDERALLY SPONSORED RESEARCH

This invention was made with government support under R01 GM084724 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 3, 2014, is named 38075-720.201_SL.txt and is 15,023 bytes in size.

BACKGROUND OF THE INVENTION

The disaccharide motif fucose-α(1-2)-galactose (Fucα(1-2)Gal) is involved in many important physiological processes, such as learning and memory, inflammation, asthma, and tumorigenesis. However, the size and structural complexity of Fucα(1-2)Gal-containing glycans has posed a significant challenge to their detection and study.

Defects in glycosylation are a hallmark of many human diseases, including autoimmune disorders, neurodegenerative diseases, and cancer. (Delves, P. J. *Autoimmunity* 1998, 27, 239; Rexach, J. E.; Clark, P. M.; Hsieh-Wilson, L. C. Nat. Chem. Biol. 2008, 4, 97; Kim, Y.; Varki, A. *Glycoconjugate J.* 1997, 14, 569.) Fucα(1-2)Gal is found on the non-reducing terminus of a large family of important glycans, including blood group H1 and H2, Globo H, Fuc-GM1, Lewis B, and Lewis Y.

SUMMARY OF THE INVENTION

The invention provides a method for labeling a glycan having a glycosyl group comprising a fucose linked to a galactose. In some embodiments, the method comprises reacting the glycan with a labeling agent in the presence of a glycosyltransferase to form a labeled glycan, wherein the labeling agent comprises a transferable glycosyl group recognized by the transferase and a reactive group capable of reacting with a detection agent, and wherein the glycosyltransferase is specific for the glycosyl group. In some embodiments, the method further comprises reacting the labeled glycan with a detection agent comprising a coupling moiety to covalently couple the detection agent to the labeling agent on the glycan. In some embodiments, the method further comprises detecting the detection agent covalently bound to the protein via the reactive group thereby detecting the presence of the protein. In some embodiments, he glycosyltransferase is specific for a fucose-α(1-2)-galactose group. In some embodiments, the glycan is a glycoprotein or glycolipid. In some embodiments, the glycosyltransferase is a bacteria homologue of the human blood group A antigen glycosyltransferase (BgtA) or a variant or fragment thereof. In some embodiments, the glycosyltransferase is a glycosyl transferase having 95% sequence identity to SEQ ID NO:1 or SEQ ID NO:2. In some embodiments, the glycosyl group comprises a fucose-α(1-2)-galactose group. In some embodiments, the detection agent recruits another agent selected from the group consisting of a secondary labeling agent, an enzyme, and a secondary detection agent. In some embodiments, the detection agent is biotin or biotin derivative. In some embodiments, the reactive group is selected from the group consisting of carbonyl group, azide group, nitril oxide group, diazoalkane group, alkyne group, and olefin group. In some embodiments, the detection agent comprises a coupling moiety selected from the group consisting of —C=C— (alkene), —C≡C— (alkyne), —NR$^1$—NH$_2$ (hydrazide), —NR$^1$ (C=O)NR$^2$NH$_2$ (semicarbazide), —NR$^1$ (C=S) NR$^2$NH$_2$ (thiosemicarbazide), —(C=O) NR$^1$NH$_2$ (carbonylhydrazide), —(C=S) NR$^1$NH$_2$ (thiocarbonylhydrazide), —(SO$_2$) NR$^1$NH$_2$ (sulfonylhydrazide), —NR$^1$NR$^2$ (C=O) NR$^3$NH$_2$ (carbazide), —NR$^1$NR$^2$ (C=S)NR$^3$NH$_2$ (thiocarbazide), and —O—NH$_2$ (aminooxy), wherein each R$^1$, R$^2$, and R$^3$ is independently H or alkyl having 1-6 carbons. In some embodiments, the detecting step is achieved by a means selected from the group consisting of radioactively, chemiluminescent, fluorescent, mass spectrometric, spin-labeling, and affinity labeling. In some embodiments, the labeling agent has the formula I:

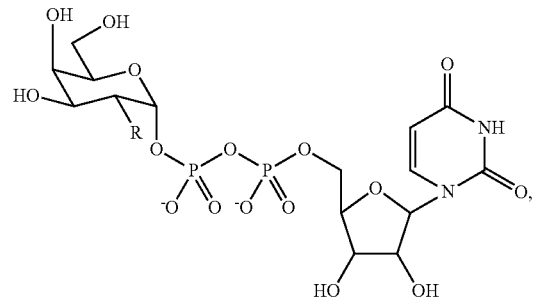

wherein R is a substituent selected from the group consisting of straight chain or branched C$_1$-C$_{12}$ carbon chain bearing a carbonyl group, azide group, straight chain or branched C$_1$-C$_{12}$ carbon chain bearing an azide group, straight chain or branched C$_1$-C$_{12}$ carbon chain bearing an alkyne, straight chain or branched C$_1$-C$_{12}$ carbon chain bearing an alkene, and —NHC(O)CH$_2$N$_3$. In some embodiments, the labeling agent has the formula II:

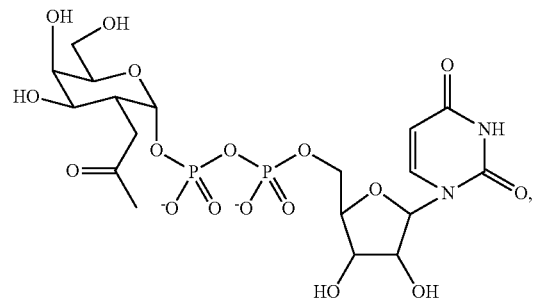

or formula III:

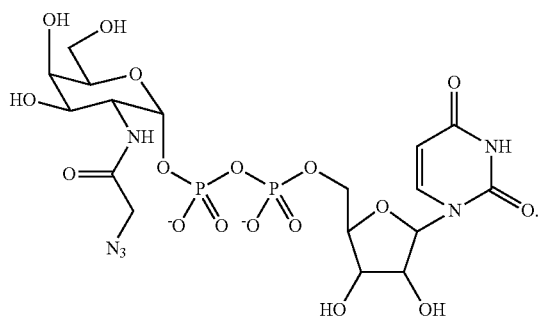

Also provided herein is a labeled glycan obtained by the method of the present invention.

Also provided herein is a labeled glycan comprising 1) a first glycosyl group comprising a fucose linked to a galactose; and 2) a second glycosyl group covalently linked to the first glycosyl group, wherein the second glycosyl group comprises a reactive group. In some embodiments, the glycan is attached to a glycoprotein or glycolipid. In some embodiments, the second glycosyl group is covalently linked to the first glycosyl group via the galactose on the first glycosyl group. In some embodiments, the second glycosyl group is covalently linked to the first glycosyl group at C-3 position of the galactose on the first glycosyl group. In some embodiments, the glycan further comprises a detection agent covalently linked to the second glycosyl group, wherein the detection agent is covalently linked to the second glycosyl group via a reaction between a coupling moiety on the detection agent and the reactive group. In some embodiments, the first glycosyl group is a fucose-α(1-2)-galactose. In some embodiments, the glycan has the formula of

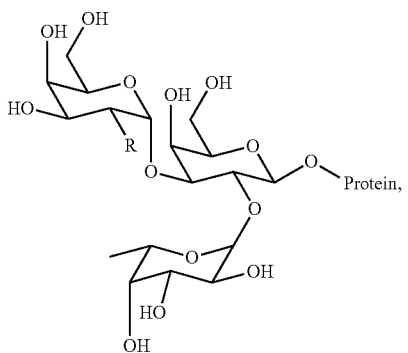

wherein R is a substitution comprising the reactive group.

In another aspect, the present invention provides a reaction mixture. In some embodiments, the reaction mixture comprises (1) a glycan having a glycosyl group comprising a fucose linked to a galactose, and (2) a labeling agent comprising a transferable glycosyl group recognized by a transferase capable of transfer the group to the glycoprotein, and a reactive group. In some embodiments, the glycan is attached to a glycoprotein or glycolipid. In some embodiments, the reaction mixture further comprises a glycosyltransferase specific for the glycosyl group on the glycoprotein. In some embodiments, the reaction mixture further comprises a detection agent, wherein the detection agent comprises a coupling moiety that is capable of reacting with the reactive group on the labeling agent to form a covalent bond. In some embodiments, the glycosyltransferase is specific for a fucose-α(1-2)-galactose group. In some embodiments, the glycosyl transferase is a bacteria homologue of the human blood group A antigen glycosyltransferase (BgtA) or a variant or fragment thereof. In some embodiments, the glycosyltransferase is a human blood group A antigen glycosyltransferase or a variant or fragment thereof. In some embodiments, the glycosyl group comprises a fucose-α(1-2)-galactose group. In some embodiments, the labeling agent has the formula I:

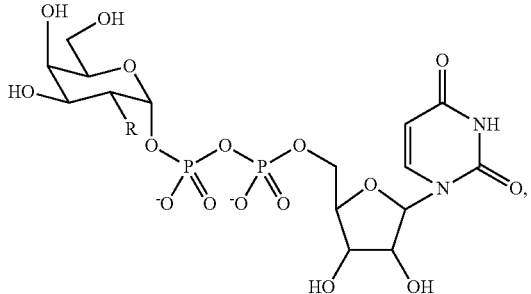

wherein R is a substituent selected from the group consisting of straight chain or branched $C_1$-$C_{12}$ carbon chain bearing a carbonyl group, azide group, straight chain or branched $C_1$-$C_{12}$ carbon chain bearing an azide group, straight chain or branched $C_1$-$C_{12}$ carbon chain bearing an alkyne, straight chain or branched $C_1$-$C_{12}$ carbon chain bearing an alkene. In some embodiments, the labeling agent has the formula II:

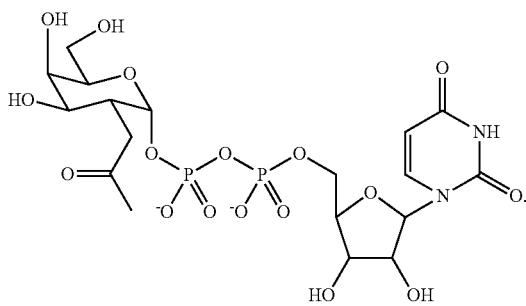

In some embodiments, the labeling agent has the formula III:

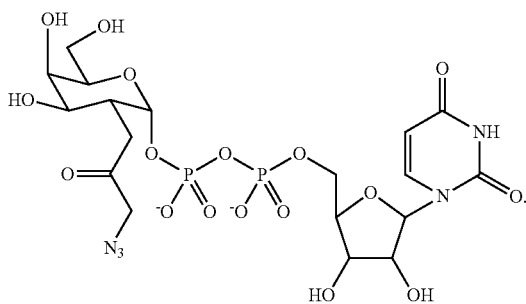

In some embodiments, the reaction mixture is placed on a solid support.

In another aspect, the present invention provides a kit for labeling a glycan with a glycosyl group comprising a fucose linked to a galactose. In some embodiments, the kit comprises: (a) a glycosyltransferase, wherein the glycosyltransferase is specific for the glycosyl group comprising a fucose linked to a galactose and is capable of catalyzing the transfer of a transferable glycosyl group on a labeling agent to the glycosyl group on the glycan; and (b) instructions instructing a user to perform the labeling using component (a). In some embodiments, the glycan is attached to a glycoprotein or glycolipid. In some embodiments, the kit further comprises a labeling agent comprising a transferable glycosyl group recognized by the transferase, and a reactive group. In some embodiments, the kit further comprises a detection agent comprising a coupling moiety capable of reacting with the reactive group on the labeling agent to form a covalent bond. In some embodiments, the glycosyl transferase is specific for a fucose-α(1-2)-galactose group. In some embodiments, the glycosyltransferase is a bacteria homologue of the human blood group A antigen glycosyltransferase (BgtA) or a variant or fragment thereof. In some embodiments, the glycosyltransferase is a human blood group A antigen glycosyltransferase or a variant or fragment thereof. In some embodiments, the glycosyl group of the glycoprotein comprises a fucose-α(1-2)-galactose group. In some embodiments, the detection agent is selected from the group consisting of fluorescent reagent, enzymatic reagent capable of converting substrates calorimetrically or fluorometrically, fluorescent and luminescent probe, metal-binding probe, protein-binding probe, probe for antibody-based binding, radioactive probe, photocaged probe, spin-label or spectroscopic probe, heavy-atom containing probe, polymer containing probe, probe for protein cross-linking, and probe for binding to particles or surfaces that contain complementary functionality. In some embodiments, the detection agent is biotin or biotin derivative. In some embodiments, the reactive group is selected from the group consisting of carbonyl group, azide group, nitril oxide group, diazoalkane group, alkyne group, and olefin group. In some embodiments, the detection agent comprises a coupling moiety selected from the group consisting of —C=C— (alkene), —C≡C— (alkyne), —NR$^1$—NH$_2$ (hydrazide), —NR$^1$(C=O)NR$^2$NH$_2$ (semicarbazide), —NR$^1$ (C=S)NR$^2$NH$_2$ (thiosemicarbazide), —(C=O) NR$^1$NH$_2$ (carbonylhydrazide), —(C=S) NR$^1$NH$_2$ (thiocarbonylhydrazide), —(SO$_2$) NR$^1$NH$_2$ (sulfonylhydrazide), —NR$^1$NR$^2$ (C=O)NR$^3$NH$_2$ (carbazide), —NR$^1$NR$^2$ (C=S)NR$^3$NH$_2$ (thiocarbazide), and —O—NH$_2$ (aminooxy), wherein each R$^1$, R$^2$, and R$^3$ is independently H or alkyl having 1-6 carbons. In some embodiments, the labeling agent has the formula I:

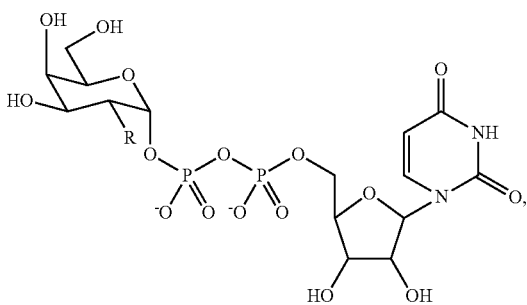

wherein R is a substituent selected from the group consisting of straight chain or branched $C_1$-$C_{12}$ carbon chain bearing a carbonyl group, azide group, straight chain or branched $C_1$-$C_{12}$ carbon chain bearing an azide group, straight chain or branched $C_1$-$C_{12}$ carbon chain bearing an alkyne, straight chain or branched $C_1$-$C_{12}$ carbon chain bearing an alkene. In some embodiments, the labeling agent has the formula II:

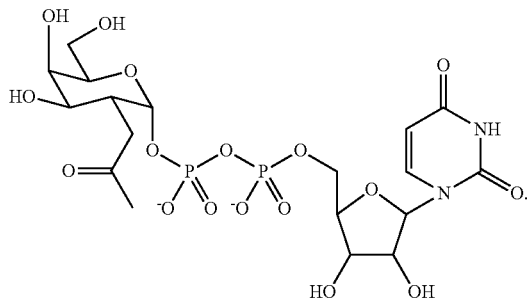

In some embodiments, the labeling agent has the formula III:

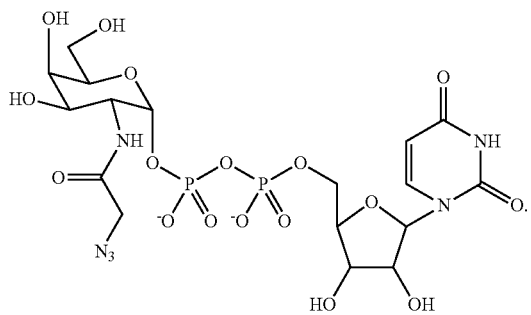

In some embodiments, the kit further comprises a separation device for purifying a labeled glycan.

In another aspect, the present invention provides a method of identifying a glycan comprising a fucose linked to a galactose. In some embodiments, the method comprises 1) providing one or more homogenous population of glycans on a solid support; 2) contacting a glycosyltransferase with the glycans in the presence of a labeling agent comprising a transferable glycosyl group, wherein the transferable glycosyl group comprises a reactive group, wherein the glycosyltransferase is specific for the glycosyl group comprising a fucose linked to a galactose and catalyzes the transfer of the transferable glycosyl group to the glycosyl group comprising a fucose linked to a galactose; 3) contacting the glycans with a detection agent, the reactive group on the transferred glycosyl group reacts with a coupling moiety on the detection agent to form a covalent bond; and 4) identifying a glycan having the covalently bound detection agent via the reactive group on the transferred glycosyl group as the glycan comprising a fucose linked to a galactose. In some embodiments, the glycans are attached to the solid support in the form of an array comprising one or more addressable locations.

In another aspect, the present invention provides a method of detecting cancer cells expressing a glycoprotein comprising a glycosyl group comprising a fucose linked to a galactose. In some embodiments, the method comprises the steps of: 1) contacting the cell with a glycosyltransferase and a labeling agent, the labeling agent comprises a transferable glycosyl group that is transferable by the transferase to the glycoprotein, wherein the transferable glycosyl group comprises a reactive group capable of reacting with a coupling moiety of a detection agent; 2) contacting the cell with a detection agent, wherein the reactive group on a transferred glycosyl group reacts with a coupling moiety on the detection agent to effect covalent coupling of the detection agent to the labeling agent; 3) detecting the amount of the detection agent covalently bound to the cell via the reactive group on the transferred labeling agent; and 4) comparing the amount of the detection agent covalently bound to the cell to the amount of the detection agent covalently bound in a non-cancerous control. An increase in the amount of the detection agent covalently bound to the cell as compared to the amount of the detection agent covalently bound in a non-cancerous control indicates a presence of cancer cells having the glycosyl group comprising a fucose linked to a galactose. In some embodiments, the detection agent recruits another agent selected from the group consisting of a labeling agent, an enzyme, and a secondary detection agent. In some embodiments, the detection agent is biotin or biotin derivative. In some embodiments, the biotin or biotin derivative recruits a secondary detection agent selected from the group consisting of fluorescent reagent, enzymatic reagent capable of converting substrates colorimetrically or fluorometrically, fluorescent and luminescent probe, metal binding probe, protein-binding probe, probe for antibody-based binding, radioactive probe, photocaged probe, spin-label or spectroscopic probe, heavy-atom containing probe, polymer containing probe, probe for protein cross-linking, and probe for binding to particles or surfaces that contain complementary functionality. In some embodiments, the reactive group is selected from the group consisting of carbonyl group, azide group, nitril oxide group, diazoalkane group, alkyne group, and olefin group. In some embodiments, the reactive group is a carbonyl group. In some embodiments, the reactive group is an azide group. In some embodiments, the detection agent comprises a coupling moiety selected from the group consisting of —C=C— (alkene), —C≡C— (alkyne), —NR$^1$—NH$_2$ (hydrazide), —NR$^1$ (C=O) NR$^2$NH$_2$ (semicarbazide), —NR$^1$(C=S)NR$^2$NH$_2$ (thiosemicarbazide), —(C=O) NR$^1$NH$_2$ (carbonylhydrazide), —(C=S) NR$^1$NH$_2$ (thiocarbonylhydrazide), —(SO$_2$) NR$^1$NH$_2$ (sulfonylhydrazide), —NR$^1$NR$^2$ (C=O)NR$^3$NH$_2$ (carbazide), —NR$^1$NR$^2$ (C=S)NR$^3$NH$_2$ (thiocarbazide), and —O—NH$_2$ (aminooxy), wherein each R$^1$, R$^2$, and R$^3$ is independently H or alkyl having 1-6 carbons. In some embodiments, the detection agent comprises a coupling moiety selected from the group consisting of —C=C— (alkene), —C≡C— (alkyne), hydrazide, aminooxy, semicarbazide, carbohydrazide, and sulfonyihydrazide. In some embodiments, the cancer is selected from the group consisting of breast cancer, lung cancer, prostate cancer, colon cancer, colorectal cancer, cervical cancer, and pancreatic cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DEFINITIONS

Figure 1:
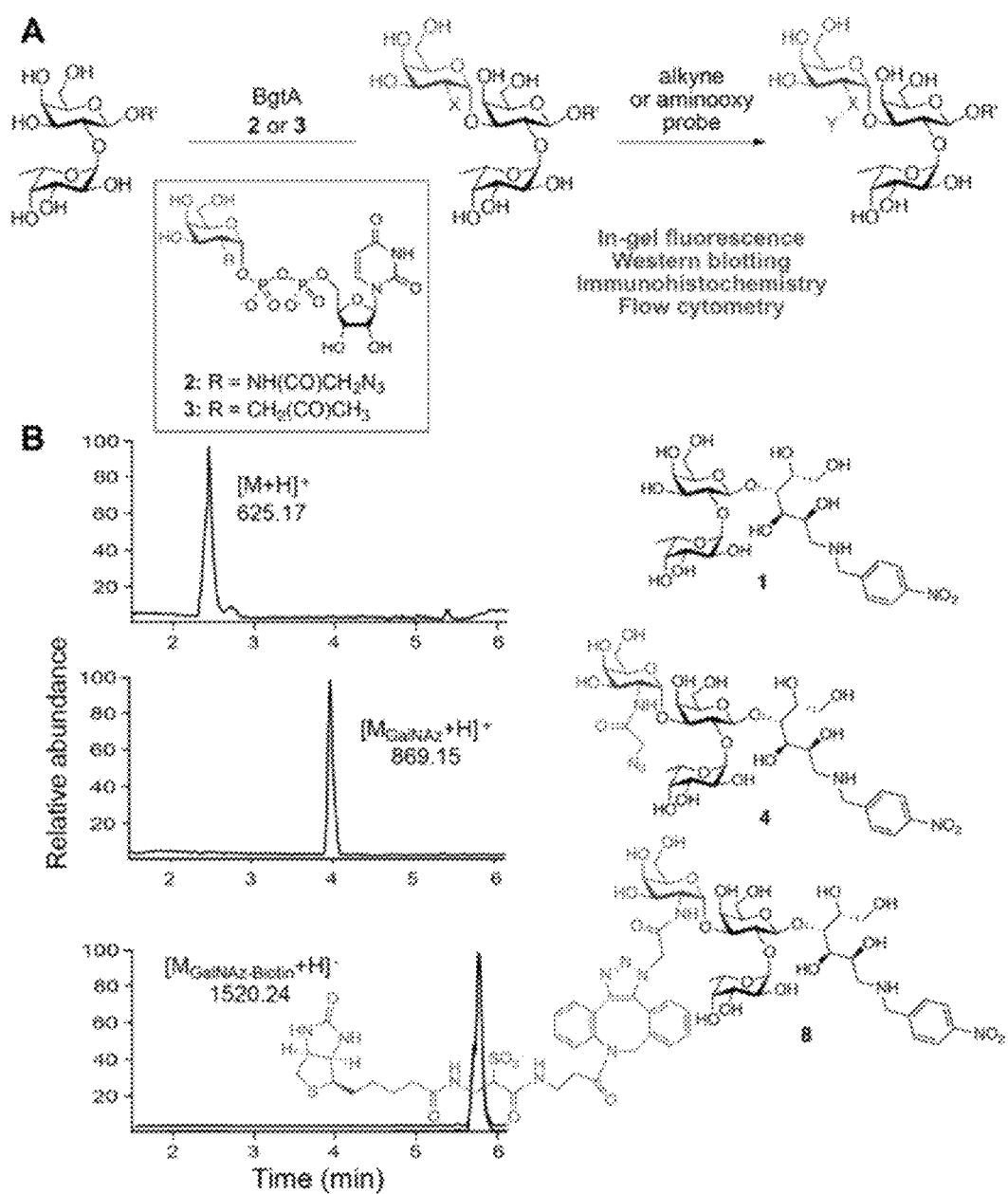
FIG. 1. (A) Chemoenzymatic strategy for the detection of Fucα(1-2)Gal glycans. (B) Labeling of substrate 1. LC-MS traces monitoring the reaction progress at time 0 (top), 12 h after the addition of BgtA and 2 (middle), and 3 h after the addition of ADIBO-biotin 6 (bottom). See SI for details.

As used in the specification and claims, the singular forms "a", "an" and "the" include plural references unless the context clearly dictates otherwise. For example, the term "a cell" includes a plurality of cells, including mixtures thereof.

A "subject," "individual" or "patient" is used interchangeably herein, which refers to a vertebrate, in some embodiments a mammal, in some embodiments a human. Mammals include, but are not limited to mice, rats, dogs, pigs, monkey (simians) humans, farm animals, sport animals, and pets. Tissues, cells and their progeny of a biological entity obtained in vivo or cultured in vitro are also encompassed.

As used herein, "labeling agent" is an agent that can react with a glycosyl group comprising a fucose linked to a galactose (e.g., a fucose-α(1-2)-galactose group). In some embodiments, a labeling agent can further comprise a reactive group for further elaboration or detection.

As used herein, "reactive group" is a functional group. In some embodiments, the reactive group can be one of a number of groups as set forth below that can react in a selective manner with a detection agent via a coupling moiety in the presence of various biomolecules. Alternatively, the reactive group can itself comprise a detection agent. Such detection agent can be a radioactive atom, as described below.

As used herein and described below, "coupling moiety" is a functional moiety that undergoes a chemical reaction with the reactive group. A coupling moiety can be contained on a detection agent to react with the reactive group.

As used herein, "detection agent" is an agent that has a property that can be observed spectroscopically or visually. Methods for production of detectably labeled proteins using detection agents are well known in the art. Detectable labels include, but are not limited to, radioisotopes, fluorophores, paramagnetic labels, antibodies, enzymes (e.g., horseradish peroxidase), or other moieties or compounds which either emit a detectable signal (e.g., radioactivity, fluorescence, color) or emit a detectable signal after exposure of the detection agent to its substrate.

A "variant" is a protein with sequence homology to the native biologically active protein that retains at least a portion of the therapeutic and/or biological activity of the biologically active protein. For example, a variant protein may share at least 70%, 75%, 80%, 85%, 90%, 95%, 96%, 97%, 98% or 99% amino acid sequence identity compared with the reference biologically active protein. As used herein, the term "biologically active protein" includes proteins modified deliberately, as for example, by site directed mutagenesis, insertions, or accidentally through mutations. A "variant" includes a "fragment", which is a truncated form of a native or non-native biologically active protein that retains at least a portion of the therapeutic and/or biological activity.

The term "sequence variant" means polypeptides that have been modified compared to their native or original sequence by one or more amino acid insertions, deletions, or substitutions. Insertions may be located at either or both termini of the protein, and/or may be positioned within internal regions of the amino acid sequence. In deletion variants, one or more amino acid residues in a polypeptide as described herein are removed. In substitution variants, one or more amino acid residues of a polypeptide are removed and replaced with alternative residues. In one aspect, the substitutions are conservative in nature and conservative substitutions of this type are well known in the art.

"Percent (%) sequence identity," with respect to the polypeptide sequences identified herein, is defined as the percentage of amino acid residues in a query sequence that are identical with the amino acid residues of a second, reference polypeptide sequence or a portion thereof, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Percent identity may be measured over the length of an entire defined polypeptide sequence, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

DETAILED DESCRIPTION OF THE INVENTION

The present invention provides methods and compositions for labeling (e.g., detecting) a protein having a glycosyl group comprising a fucose linked to a galactose. The invention also provides a labeled protein obtained from contacting the protein with a labeling agent and optionally a detection agent. Typically, the labeling agent comprises a reactive group and a transferable glycosyl group. Where desired, the reactive group is located on the transferable glycosyl group. The reactive group on the transferred glycosyl group is capable of reacting with a coupling moiety on the detection agent to form a covalent bond. An exemplary labeled protein comprises a first glycosyl group comprising a fucose linked to a galactose and a second glycosyl group covalently linked to the first glycosyl group. The present invention further provides methods, compositions, kits, and arrays for detecting certain disease states, such as cancer.

Methods of Labeling or Detecting a Glycan

The present invention provides methods for labeling (e.g., detecting) a glycan (e.g., a glycoprotein), particularly glycan having a glycosyl group comprising a fucose linked to a galactose. In some embodiments, the methods involve reacting the glycan with a labeling agent in the presence of a glycosyltransferase to form a labeled glycan. The labeling agent comprises a transferable glycosyl group recognized by the transferase, and further comprises a reactive group capable of reacting with a detection agent. The glycosyltransferase is specific for a glycosyl group comprising a fucose linked to a galactose and can catalyze the transfer of the transferable glycosyl group on the labeling agent to the glycosyl group comprising a fucose linked to a galactose on a glycan (e.g., a glycoprotein). A modified glycan results from reaction of the labeling agent with the glycosyl group comprising a fucose linked to a galactose on the protein. In some embodiments, the glycosyl group is a fucose-$\alpha$(1-2)-galactose group. In some embodiments, the glycosyltransferase is specific for a fucose-$\alpha$(1-2)-galactose group. Exemplary glycosyltransferases include a human blood group A antigen glycosyltransferase or a variant or fragment thereof, e.g., a bacteria homologue of the human blood group A antigen glycosyltransferase (BgtA) or a variant or fragment thereof.

The labeling agent can further comprise a reactive group. The reactive group on the labeling agent can react with a detection agent via a reaction between the reactive group and a coupling moiety on the detection agent. Where desired, the reactive group does not react substantially with a protein or other components of a biological mixture. In some embodiments, the detection agent is covalently coupled to the labeling agent after the labeling agent is conjugated to the glycan in the presence of a glycosyltransferase to form a labeled glycan. The reactive group on the labeling agent can be used to further react the modified protein with a detection agent via a reaction between the reactive group and a coupling moiety on the detection agent. In some embodiments, the detection agent is first covalently coupled to the labeling agent. The resulting compound is then reacted with the glycan to form a labeled glycan.

The detection agent can be detectable through various detection means, such as, but not limited to, radioactively, chemiluminescence, fluorescence, mass spectrometry, spin labeling, affinity labeling, or the like. The detection agent can be, for example, a radiolabeled compound or a fluorescent compound. The detection agent also can be detectable indirectly, for example, by recruitment of one or more additional factors.

In some embodiments, the glycan is attached to a glycoprotein or glycolipid. Glycoproteins comprise proteins covalently linked to carbohydrate. The predominant sugars found in glycoproteins are glucose, galactose, mannose, fucose, GalNAc, GlcNAc and NANA. Carbohydrates can be linked to the protein component through O-glycosidic, N-glycosidic, or C-glycosidic bonds. In some embodiments, the methods described herein are useful for detecting glycosylated proteins. In some embodiments, certain post-translational modifications will append a glycosyl group. In some embodiments, the glycosyl group is a glycosyl group comprising a fucose linked to a galactose. In some embodiments, proteins having a glycosyl group comprising a fucose linked to a galactose are detected. In some embodiments, proteins having a fucose-$\alpha$(1-2)-galactose group are detected. Changes in fucose-$\alpha$(1-2)-galactose levels have been associated with disease states such as cancer.

In some embodiments, a labeling agent is an agent that can react with a target glycosyl group of a glycan (e.g., a glycoprotein) while further comprising a reactive group for further reaction. A glycosyltransferase specific for the target glycosyl group can be used to transfer a transferable glycosyl group on the labeling agent to the target glycosyl group on the glycan of interest. The glycosyltransferase can be a naturally occurring glycosyltransferase, a mutant glycosyltransferase, or an evolved glycosyltransferase that is specific for the target glycosyl group. In some embodiments, the glycosyltransferase is specific for a glycosyl group comprising a fucose linked to a galactose. In some embodiments, the glycosyltransferase is specific for a fucose-$\alpha$(1-2)-galactose group.

Exemplary glycosyltransferases include, but are not limited to, a human blood group A antigen glycosyltransferase or a variant or fragment thereof. In some embodiments, glycosyltransferases include a bacteria homologue of the human blood group A antigen glycosyltransferase or a variant or fragment thereof, e.g., a *Helicobacter mustelae* homologue of the human blood group A antigen glycosyltransferase or a variant or fragment thereof (Yi, W.; Shen, J.; Zhou, G.; Li, J.; Wang, P. G. *J. Am. Chem. Soc.* 2008, 130, 14420). In some embodiments, glycosyltransferases are engineered to accept unnatural substrates. For example, in some embodiments, glycosyltransferases are engineered to tolerate unnatural substrates containing substitutions at one or more positions on the sugar ring (e.g., the C-2 position).

In some embodiment, the glycosyltransferase is a variant (e.g., a sequence variant) or fragment of a glycosyl transferase having SEQ ID NO:1, 2, 3, 4, or 5. In some embodiments, the glycosyltransferase is a glycosyltransferase having at least 70%, 75%, 80%, 85%, 90%, 95%, 96%, 97%, 98% or 99% amino acid sequence identity to SEQ ID NO:1, 2, 3, 4, or 5. In some embodiment, the glycosyltransferase is SEQ ID NO:1, 2, 3, 4, or 5.

The reactive group can be one of a number of groups that can react in a selective manner with the coupling moiety of a detection agent in the presence of various biomolecules, and particularly in an aqueous solution. Alternatively, the reactive group can itself comprise a detection agent. In some embodiments, the reactive group comprises a radioactive substance. A reactive group is contained on a labeling agent, e.g., on a transferable glycol group of the labeling agent.

In some embodiments, the reactive group is a carbonyl group reactive group. The carbonyl group participates in a large number of reactions from addition and decarboxylation reactions to aldol condensations. Moreover, the unique reactivity of the carbonyl group allows it to be selectively modified with hydrazide and aminooxy derivatives in the presence of the other amino acid side chains. See, e.g., Cornish, V. W., Hahn, K. M. & Schultz, P. G. (1996) *J. Am. Chem. Soc.* 118:8150-8151; Geoghegan, K. F. & Stroh, J. G. (1992) *Bioconjug. Chem.* 3:138-146; and, Mahal, L. K., Yarema, K. J. & Bertozzi, C. R. (1997) *Science* 276:1125-1128. This functional group is generally absent from proteins and thus can serve as a reactive group for subsequent protein modification.

For reaction with the carbonyl group reactive group, a coupling moiety can be —NR$^1$—NH$_2$ (hydrazide), —NR$^1$(C=O)NR$^2$NH$_2$ (semicarbazide), —NR$^1$(C=S)NR$^2$NH$_2$ (thiosemicarbazide), —(C=O)NR$^1$NH$_2$ (carbonylhydrazide), —(C=S)NR$^1$NH$_2$ (thiocarbonylhydrazide), —(SO$_2$)NR$^1$NH$_2$ (sulfonylhydrazide), —NR$^1$NR$^2$ (C=O)NR$^3$NH$_2$ (carbazide), —NR$^1$NR$^2$(C=S)NR$^3$NH$_2$ (thiocarbazide), —O—NH$_2$ (aminooxy), and/or the like, where each R$^1$, R$^2$, and R$^3$ is independently H, or alkyl having 1-6 carbons, in some embodiments H. In some embodiments, the coupling moiety is a —C=C— (alkene), —C≡C— (alkyne), hydrazide, aninooxy, semicarbazide, carbohydrazide, a sulfonylhydrazide, or the like.

The product of the reaction between the reactive group and the coupling moiety typically incorporates the atoms originally present in the coupling moiety. Typical linkages obtained by reacting the aldehyde or ketone reactive groups with certain coupling moieties include but are not limited to reaction products such as an oxime, a hydrazone, a reduced hydrazone, a carbohydrazone, a thiocarbohydrazone, a sulfonylhydrazone, a semicarbazone, a thiosemicarbazone, or similar functionality, depending on the nucleophilic moiety of the coupling moiety and the aldehyde or ketone reactive group. Linkages with carboxylic acids are also possible and result in carbohydrazides or hydroxamic acids. Linkages with sulfonic acid reactive groups are also possible with the above coupling moiety s and result in sulfonylhydrazides or N-sulfonylhydroxylamines. The resulting linkage can be subsequently stabilized by chemical reduction. For instance, the carbonyl group reacts readily with hydrazides, aminooxy, and semicarbazides under mild conditions in aqueous solution, and forms hydrazone, oxime, and semicarbazone linkages, respectively, which are stable under physiological conditions. See, e.g., Jencks, W. P. (1959) *J. Am. Chem. Soc.* 81, 475-481; Shao, J. & Tam, J. P. (1995) *J. Am. Chem. Soc.* 117:3893-3899.

A native or mutated glycosyltransferase can be employed to transfer a monosaccharide labeling agent containing an azide reactive group, an alkyne reactive group, a nitril oxide reactive group, or a diazoalkane reactive group, onto the target glycosyl group (e.g., a glycosyl group comprising a fucose linked to a galactose). Once incorporated, the azide, alkyne, nitril oxide, or diazoalkane reactive group on the saccharide labeling agent can then be modified by, e.g., a Huisgen [3+2] cycloaddition reaction in aqueous conditions in the presence of a catalytic amount of copper (See, e.g., Tornoe, et al., (2002) *Org. Chem.* 67:3057-3064; and, Rostovtsev, et al., (2002) *Angew. Chem. Int. Ed.* 41:2596-2599; Padwa, A. in *Comprehensive Organic Synthesis, Vol.* 4, (1991) Ed. Trost, B. M., Pergamon, Oxford, p. 1069-1109; and, Huisgen, R. in 1,3-*Dipolar Cycloaddition Chemistry*, (1984) Ed. Padwa, A., Wiley, New York, p. 1-176). In a [3+2] cycloaddition addition reaction, where either an azide, alkyne, nitril oxide, or diazoalkane is a reactive group, the other functionality would act as a coupling moiety. The [3+2] cycloaddition addition reaction can be used to introduce affinity probes (biotin), dyes, polymers (e.g., poly (ethylene glycol) or polydextran) or other monosaccharides (e.g., glucose, galactose, fucose, 0-GlcNAc, mannose-derived saccharides bearing the appropriate reactive group). The Huisgen 1,3-dipolar cycloaddition of azides and acetylenes can give 1,2,3-triazoles, also called "click chemistry." (see Lewis W G, Green L G, Grynszpan F, Radic Z, Carlier P R, Taylor P, Finn M G, Sharpless K B. *Angewandte Chemie—Int'l Ed.* 41 (6): 1053.). In addition, strain-promoted, Cu-free reactions of azides with cyclooctynes and dibenzocyclooctynes can also be used (See, e.g., Jewett and Bertozzi, Chem. Soc. Rev., 2010, 39, 1272-1279; Coats, et al., Org. Lett. 7:1469-1472, 2005; Seo, et al., J. Org. Chem. 68:609-612, 2003; Li, et al., Tet. Lett., 45:3143-3146, 2004).

An exemplary method disclosed herein involves a cycloaddition rather than a nucleophilic substitution reaction, modification of proteins can be performed with extremely high selectivity (as opposed to reactions with amines, carboxylates or sulfhydryl groups which are found more commonly on the surface of proteins). The reaction can be carried out at room temperature in aqueous conditions with excellent regioselectivity (1,4>1,5) by the addition of catalytic amounts of Cu(I) salts to the reaction mixture. See, e.g., Tomoe, et al., (2002) *Org. Chem.* 67:3057-3064; and, Rostovtsev, et al., (2002) *Angew. Chem. Int. Ed.* 41:2596-2599. The resulting five-membered ring that is attached to the labeling agent and the detection agent that results from the Huisgen [3+2] cycloaddition is not generally reversible in reducing environments and is stable against hydrolysis for extended periods in aqueous environments.

The reactive group also can be an azido group capable of reacting in a Staudinger reaction (see, for example, Saxon, E.; Luchansky, S. J.; Hang, H. C.; Yu, C.; Lee, S. C.; Bertozzi, C. R.; *J. Am. Chem. Soc.;* 2002; 124(50); 14893-14902.). The Staudinger reaction, which involves reaction between trivalent phosphorous compounds and organic azides (Staudinger et al. Helv. Chim. Acta 1919, 2, 635), has been used for a multitude of applications. (Gololobov et al. Tetrahedron 1980, 37, 437); (Gololobov et al. Tetrahedron 1992, 48, 1353). There are almost no restrictions on the nature of the two reactants. The phosphine can have a neighboring acyl group such as an ester, thioester or N-acyl imidazole (i.e. a phosphinoester, phosphinothioester, phosphinoimidazole) to trap the aza-ylide intermediate and form a stable amide bond upon hydrolysis. The phosphine can also be typically a di- or triarylphosphine to stabilize the phosphine.

The labeling agent can comprise an olefin reactive group and can be reacted with a coupling moiety on a detection agent using a cross metathesis reaction in the presence of a catalyst. In a cross metathesis reaction, where the reactive group is an olefin, a coupling moiety is an olefin, an alkyne, or an appropriate substrate for a metathesis reaction with an olefin. Commonly, where the reactive group is an olefin, a coupling moiety is also an olefin. Catalysts for a cross metathesis reaction are well-known and include water-soluble catalysts. such as those described in Lynn D M, Mohr B, Grubbs R H, Henling L M, and Day M W (2000) *J. Am. Chem. Soc.;* 2000; 122: 6601-6609 and those review in Chen L Y, Yang H J, Sun W H (2003) *Progress In Chemistry* 15: 401-408.

The reactive group is substantially not reactive with components of a biological mixture, such as a typical cellular extract, including for example, nucleic acids and proteins. An exemplary reactive group is a carbonyl reactive group, which can react with a coupling moiety, such as an aminoxy, hydrazide or thiosemicarbazide group on the detection agent. Another exemplary reactive group is an azide group, which can react with a coupling moiety, such as an alkene group or an alkyne group in a reaction, e.g., a Huisgen [3+2] cycloaddition reaction.

In some embodiments, the labeling agent is a UDP-Gal having a substituent R appeneded at any suitable position of the galactose ring. For example, the substituent R can be appended at C-2, C-3, C-4, or C-6 position of the galactose ring. In some embodiments, the labeling agent has a formula of

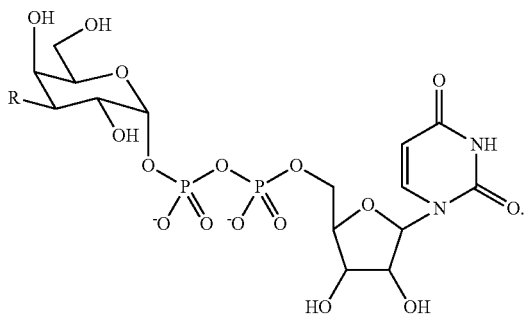

In some embodiments, the labeling agent has a formula of

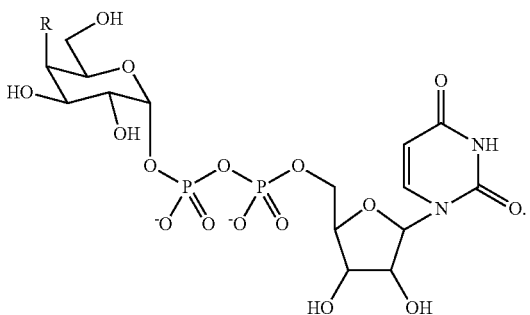

In some embodiments, the labeling agent has a formula of

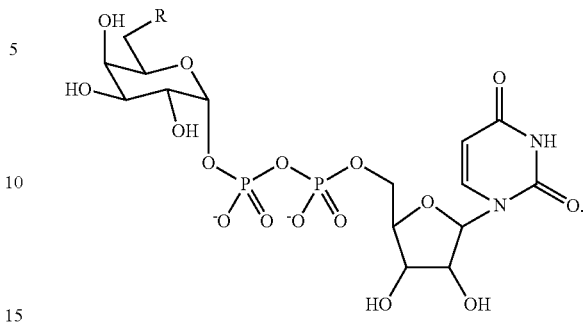

In some embodiments, the substituent R was appended at the C-2 position of the galactose ring because the glycosyltransferase of the present invention have been shown to tolerate unnatural substrates containing minor substitutions at the C-2 position. In some embodiments, the labeling agent has a formula I:

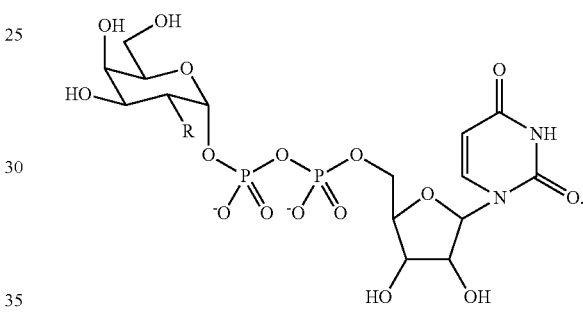

In some embodiments, R is a substituent selected from the group consisting of straight chain or branched $C_1$-$C_{12}$ carbon chain bearing a carbonyl group, azide group, straight chain or branched $C_1$-$C_{12}$ carbon chain bearing an azide group, straight chain or branched $C_1$-$C_{12}$ carbon chain bearing an alkyne, and straight chain or branched $C_1$-$C_{12}$ carbon chain bearing an alkene. In some embodiments, R is selected from the group consisting of straight chain or branched $C_2$-$C_4$ carbon chain bearing a carbonyl group, azide group, straight chain or branched $C_2$-$C_4$ carbon chain bearing an azide group, straight chain or branched $C_2$-$C_4$ carbon chain bearing an alkyne, and straight chain or branched $C_2$-$C_4$ carbon chain bearing an alkene.

In some embodiments, R is —OH, —NH$_2$, —NHC(O)CH$_3$, —NHC(O)—C$_{1-6}$alkyl, —NHC(O)CH$_2$N$_3$, —NHC(O)—C$_{1-6}$alkyl-N$_3$, —NHC(O)CH$_2$C≡CH, or —NHC(O)—C$_{1-6}$alkyl-C≡CH. In some embodiments, R is not —OH.

In some embodiments, R is optionally substituted aliphatic. In certain embodiments, R is —CH2C(O)R$^2$. In certain embodiments, R is —C(O)R$^2$. In certain embodiments, R is —C(O)CH$_3$, —CH2C(O)CH$_3$, —C(O)CH=CH$_2$, —CH$_2$C(O)CH=CH$_2$, —C$_{1-6}$alkyl-C(O)CH=CH$_2$, —NHC(O)CH=CH$_2$, —CH$_2$NHC(O)CH=CH$_2$, —C$_{1-6}$alkyl-NHC(O)CH=CH$_2$, —NHS(O)CH=CH$_2$, —CH$_2$NHS(O)CH=CH$_2$, or —C$_{1-6}$alkyl-NHS(O)CH=CH$_2$. In some embodiments, R is —(CH$_2$)q-C(O)R$^2$, wherein q is 0, 1, 2, 3, 4, 5, 6, 7, 8, 9, 10, 11, 12, 13, 14, 15, 16, 17, 18, 19, 20, 21, 22, 23, or 24. In some embodiments, R$^2$ is aliphatic optionally substituted with —N$_3$, —CN, —NC, —NCO, —OCN, —NCS, —SCN, —NO, or —N$_2$. In certain embodiments, R is —(CH$_2$)qC(O)CH$_2$N$_3$, —(CH₂)qC(O)CH₂CN, —(CH₂)qC(O)CH2NC, —(CH₂)qC(O)CH₂OCN, —(CH₂)qC(O)CH₂NCO, —(CH₂)qC(O)CH₂NCS, —(CH₂)qC(O)CH₂SCN, —(CH₂)qC(O)CH₂NO, or —(CH₂)qC(O)CHN₂. In certain embodiments, R is —C(O)CH₂N₃, —C(O)CH₂CN, —C(O)CH₂NC, —C(O)CH₂OCN, —C(O)CH₂NCO, —C(O)CH₂NCS, —C(O)CH₂SCN, —C(O)CH₂NO, or —C(O)CHN₂, wherein q is 0, 1, 2, 3, 4, 5, 6, 7, 8, 9, 10, 11, 12, 13, 14, 15, 16, 17, 18, 19, 20, 21, 22, 23, or 24. In certain embodiments, R is —CH₂C(O)CH₂N₃, —CH₂C(O)CH₂CN, —CH₂C(O)CH₂NC, —CH₂C(O)CH₂OCN, —CH₂C(O)CH₂NCO, —CH₂C(O)CH₂NCS, —CH₂C(O)CH₂SCN, —CH₂C(O)CH₂NO, or —CH₂C(O)CH₂N₂. In some embodiments, R² is optionally aliphatic substituted with halo, e.g., aliphatic substituted with fluoro, chloro, bromo, or iodo. In certain embodiments, R is —(CH₂)qC(O)CH₂Cl, —(CH₂)qC(O)CH₂Br, or —(CH₂)qC(O)CH₂I, wherein q is 0, 1, 2, 3, 4, 5, 6, 7, 8, 9, 10, 11, 12, 13, 14, 15, 16, 17, 18, 19, 20, 21, 22, 23, or 24. In certain embodiments, R is —C(O)CH₂Cl, —C(O)CH₂Br, or —C(O)CH₂I. In certain embodiments, R is —CH₂C(O)CH₂Cl, —CH₂C(O)CH₂Br, or —CH₂C(O)CH₂I. In certain embodiments, R is —(CH₂)qC(O)CH₂CF₃, wherein q is 0, 1, 2, 3, 4, 5, 6, 7, 8, 9, 10, 11, 12, 13, 14, 15, 16, 17, 18, 19, 20, 21, 22, 23, or 24. In certain embodiments, R is —C(O)CH₂CF₃. In certain embodiments, R is —CH₂C(O)CH₂CF₃. In some embodiments, R² is optionally aliphatic substituted with amino. In certain embodiments, R is —(CH₂)qC(O)CH₂NH₂, wherein q is 0, 1, 2, 3, 4, 5, 6, 7, 8, 9, 10, 11, 12, 13, 14, 15, 16, 17, 18, 19, 20, 21, 22, 23, or 24. In certain embodiments, R is —C(O)CH₂NH₂. In certain embodiments, R is —CH₂C(O)CH₂NH₂. In certain embodiments, R² is optionally aliphatic substituted with hydroxy. In certain embodiments, R is —(CH₂)qC(O)CH₂OH, wherein q is 0, 1, 2, 3, 4, 5, 6, 7, 8, 9, 10, 11, 12, 13, 14, 15, 16, 17, 18, 19, 20, 21, 22, 23, or 24. In certain embodiments, R is —C(O)CH₂OH. In certain embodiments, R is —CH₂C(O)CH₂OH. In certain embodiments, R² is optionally aliphatic substituted with aryl or heteroaryl. In certain embodiments, R² is optionally —CH₂-aryl or —CH₂-heteroaryl. In certain embodiments, R² is optionally aliphatic substituted with optionally substituted heterocyclyl.

In certain embodiments, R is —N(R³)2. In certain embodiments, R is —NH2. In certain embodiments, R is —NHC(O)R², wherein R² is optionally substituted aliphatic. In certain embodiments, R is —NHC(O)CH₃, or —NHC(O)CH=CH₂. In certain embodiments, R is —NHC(O)R², wherein R² is aliphatic substituted with halo. In certain embodiments, R is —NHC(O)R², wherein R² is aliphatic substituted with chloro, bromo, or iodo. In certain embodiments, R is —NHC(O)R², wherein R² is aliphatic substituted with fluoro. In certain embodiments, R is —NHC(O)CH₂Cl, —NHC(O)CH₂Br, or —NHC(O)CH₂I. In certain embodiments, R is —NHC(O)CH₂CF₃. In certain embodiments, R is —NHC(O)R², wherein R² is aliphatic substituted with —N₃, —CN, —NC, —NCO, —OCN, —NCS, —SCN, —NO, or —N₂. In certain embodiments, R is —NHC(O)CH₂N₃, —NHC(O)CH₂CN, —NHC(O)CH₂NC, —NHC(O)CH₂OCN, —NHC(O)CH₂NCO, —NHC(O)CH₂NCS, —NHC(O)CH₂SCN, —NHC(O)CH₂NO, or —NHC(O)CHN₂. In certain embodiments, R is —NHC(O)R², wherein R² is aliphatic substituted with amino. In certain embodiments, R is —NHC(O)CH₂NH₂. In certain embodiments, R is —NHC(O)R², wherein R² is aliphatic substituted with hydroxy. In certain embodiments, R is —NHC(O)CH₂OH. In certain embodiments, R is —NHC(O)R², wherein R² is aliphatic substituted with aryl or heteroaryl. In certain embodiments, R is —NHC(O)R², wherein R² is —CH₂-aryl or —CH₂heteroaryl. In certain embodiments, R is —NHC(O)R², wherein R² is aliphatic substituted with optionally substituted heterocyclyl.

In certain embodiments, R is —OR⁴. In certain embodiments, R is —OH. In certain embodiments, R is —O—(protecting group). In certain embodiments, R is —OAc. In certain embodiments, R is —OC(O)R². In certain embodiments, R is —OC(O)R², wherein R² is optionally substituted aliphatic. In certain embodiments, R is —OC(O)CH₃, or —OC(O)CH=CH₂. In certain embodiments, R is —OC(O)R², wherein R² is aliphatic substituted with halo. In certain embodiments, R is —OC(O)R², wherein R² is aliphatic substituted with chloro, bromo, or iodo. In certain embodiments, R is —OC(O)R², wherein R² is aliphatic substituted with fluoro. In certain embodiments, R is —OC(O)CH₂Cl, —OC(O)CH₂Br, or —OC(O)CH₂I. In certain embodiments, R is —OC(O)CH2CF. In certain embodiments, R is —OC(O)R², wherein R² is aliphatic substituted with —N3, —CN, —NC, —NCO, —OCN, —NCS, —SCN, —NO, or —N₂. In certain embodiments, R is —OC(O)CH₂N₃, —OC(O)CH₂CN, —OC(O)CH₂NC, —OC(O)CH₂OCN, —OC(O)CH₂NCO, —OC(O)CH₂NCS, —OC(O)CH₂SCN, —OC(O)CH₂NO, or —OC(O)CHN₂. In certain embodiments, R is —OC(O)R², wherein R² is aliphatic substituted with amino. In certain embodiments, R is —OC(O)CH₂NH₂. In certain embodiments, R is —OC(O)R², wherein R² is aliphatic substituted with hydroxy. In certain embodiments, R is —OC(O)CH₂OH. In certain embodiments, R is —OC(O)R², wherein R² is aliphatic substituted with aryl or heteroaryl. In certain embodiments, R is —OC(O)R², wherein R² is —CH₂-aryl or —CH₂-heteroaryl. In certain embodiments, R is —OC(O)R², wherein R² is aliphatic substituted with optionally substituted heterocyclyl.

In some embodiments, the labeling agent has a formula II:

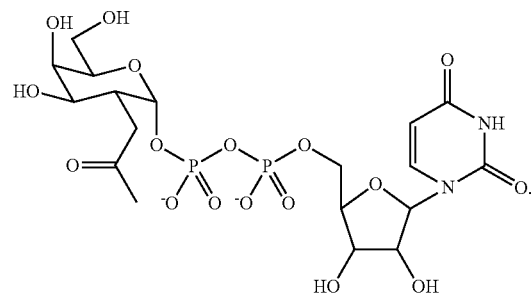

In some embodiments, the labeling agent has a formula III:

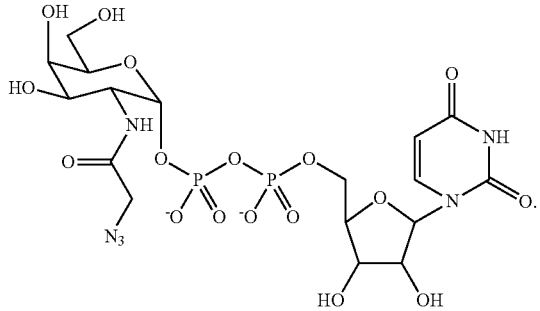

A labeling agent has a formula II was synthesized from the previously reported synthesis scheme (Hang, H. C.; Bertozzi, C. R. J. Am. Chem. Soc. 2001, 123, 1242-1243). The following conditions can be used: (a) Me$_2$NH, THF (53%); (b) (BnO)$_2$PNiPr$_2$, then mCPBA (54%); (c) Pd/C, H$_2$, tri-n-octylamine; (d) UMP-morpholidate, 1H-tetrazole, pyr; (e) TEA, H$_2$O/MeOH (45%, 3 steps). Synthesis of a agent has a formula I follows closely this scheme, except with the use a different starting material.

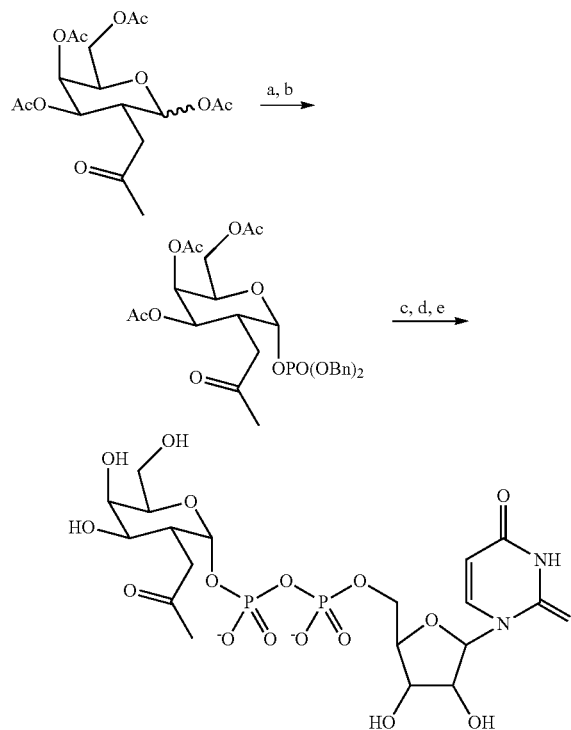

A variety of detection agents can be used. The detection agent can itself be detectable, or can be used to recruit another labeling molecule or enzyme, a secondary detection agent. The detection agent has a coupling moiety that can bind to or react with the reactive group.

A detection agent is an agent that has a property that can be observed spectroscopically or visually. Methods for production of detectably labeled proteins using detection agents are well known in the art. The detection agent can be detectable through various detection means, such as radioactively, chemiluminescence, fluorescence, mass spectrometry, spin labeling, affinity labeling, or the like. The detection agent also can be detectable indirectly, for example, by recruitment of one or more additional factors.

A radioactive substance refers to a radioactive atom, a substance having radioactive atoms incorporated therein, or a substance radiolabeled with an additional or substituted radioactive atom not normally found in the native substance. Examples of radioactive atoms include, but are not limited to, $^{32}$P, $^{33}$P, $^{35}$S, 125I, $^{3}$H, $^{13}$C, $^{14}$C, $^{51}$Cr and $^{18}$O. In one embodiment, the reactive group further comprises such a radioactive substance.

Most chemiluminescence methods involve chemical components to actually generate light. Chemiluminescence is the generation of electromagnetic radiation as light by the release of energy from a chemical reaction. While the light can, in principle, be emitted in the ultraviolet, visible or infrared region, those emitting visible light are the most common. Chemiluminescent reactions can be grouped into three types:

1) Chemical reactions using synthetic compounds and usually involving a highly oxidized species, such as peroxide, are commonly termed chemiluminescent reactions.

2) Light-emitting reactions arising from a living organism, such as the firefly or jellyfish, are commonly termed bioluminescent reactions.

3) Light-emitting reactions which take place by the use of electrical current are designated electrochemiluminescent reactions.

Examples of chemiluminescent detection agents include, but are not limited to, luminol chemiluminescence, peroxyoxalate chemiluminescence, and diphenylanthracene chemiluminescence.

Fluorescence is the phenomenon in which absorption of light of a given wavelength by a fluorescent molecule is followed by the emission of light at longer wavelengths. Examples of fluorescent detection agents include, but are not limited to, rhodamine, fluorescein, Texas red, cyanine dyes, nanogold particles coated with gold, and analogues thereof and alike.

Mass spectrometry is an analytical technique that is used to identify unknown compounds, quantify known materials, and elucidate the structural and physical properties of ions. Mass Spectrometry can be used in conjunction with chromatography techniques, such as LC-MS and GC-MS. Examples of mass spectrometry tools for use as detection agents include, but are not limited to, electron ionisation (EI), chemical ionisation (CI), fast atom bombardment (FAB)/liquid secondary ionisation (LSIMS), matrix assisted laser desorption ionisation (MALDI), and electrospray ionisation (ESI). See, for example, Gary Siuzdak, *Mass Spectrometry for Biotechnology*, Academic Press, San Diego, 1996.

Electron paramagnetic resonance (EPR), also known as electron spin resonance (ESR) and electron magnetic resonance (EMR), is the name given to the process of resonant absorption of microwave radiation by paramagnetic ions or molecules, with at least one unpaired electron spin, and in the presence of a static magnetic field. Species that contain unpaired electrons include free radicals, odd electron molecules, transition-metal complexes, lanthanide ions, and triplet-state molecules.

Affinity labeling is a method for tagging molecules so that they can be more easily detected and studied. Affinity labeling can be based on substituting an analogue of a native substrate.

In one embodiment, the detection agent is a biotin or a biotin derivative. Biotin and biotin derivatives are well known to one of skill in the art, and are described in the *Handbook of Fluorescent Probes and Research Products*, Ninth Edition, Molecular Probes, Eugene, Oreg., 2002. Additional detection schemes also are provided in the *Handbook*. Secondary detection agents also are disclosed, including fluorescent reagents (e.g., fluorescently labeled streptavidin) and enzymatic reagents that can convert substrates colorimetrically or fluorometrically (e.g., streptavidin alkaline phosphatase and streptavidin-horseradish peroxidase conjugates). A number of detection schemes are known to one of skill in the art and include, for example: fluorescent and luminescent probes (e.g., fluoroscein hydrazide, metal nanoparticles or quantum dots) (see, e.g., Geoghegan, K. F. & Stroh, J. G. (1992) *Bioconjug. Chem.* 3:138-146); metal-binding probe (e.g., polyhistidine tag or metal chelate); protein-binding probes (e.g., FLAG-tag); probe (e.g., dinitrophenol) for antibody-based binding; radioactive probe (circumvent challenging synthesis and handling of radiolabeled monosaccharides); photocaged probe; spin-label or spectroscopic probe; heavy-atom containing probe (i.e., Br, I) for x-ray crystallography studies; polymer (e.g. PEG- or poly(propylene)glycol) containing probe; probes that permit protein cross-linking (e.g., to covalently modify binding partners to protein being modified, such as containing diazirene, benzophenone, or azidophenyl groups); and binding to particles or surfaces that contain complementary functionality.

In some embodiments, the present invention provide methods for the rapid and sensitive detection of fucose-α (1-2)-galactose group containing glycans (e.g., glycoproteins). One approach capitalizes on the substrate tolerance of glycosyltransferases of the present invention, which allows for chemoselective installation of a non-natural reactive group (e.g., a ketone or azide reactive group) to fucose-α (1-2)-galactose group containing proteins (FIG. 1A). These reactive groups (e.g., a ketone or azide reactive group) have been well-characterized in cellular systems as a neutral, yet versatile reactive group. In some embodiments, the ketone or azide reactive group serves as a unique marker to "tag" fucose-α(1-2)-galactose group containing proteins with biotin. Once biotinylated, the modified proteins can be readily detected by fluorescence or chemiluminescence, such as using streptavidin conjugated to horseradish peroxidase (HRP).

FIG. 1A shows a general strategy for detection of fucose-α(1-2)-galactose group containing proteins. In some exemplary embodiments, as shown in FIG. 1A, the methods are used to detect fucose-α(1-2)-galactose moiety on a protein or a mixture of proteins. According to the methods, a protein having the fucose-α(1-2)-galactose moiety is contacted with a labeling agent comprising a reactive group. The labeling agent can be a substrate of a particular enzyme that reacts with the fucose-α(1-2)-galactose moiety on the protein to be labeled, for example, the labeling agent can be an analog of uridyl phosphate sugar. A glycosyltransferase can transfer the labeling agent to the fucose-α(1-2)-galactose pendant moiety on the protein. In one embodiment, the reactive group is a ketone or azide moiety, which is substantially unreactive with biological constituents. When the reactive group is a ketone, the labeled protein can then be reacted with a detection agent comprising a coupling moiety, for example, a detection agent having an aminoxy, hydrazide or thiosemicarbazide coupling moiety. When the reactive group is an azide, the labeled protein can then be reacted with a detection agent comprising a coupling moiety, for example, via a Huisgen [3+2] cycloaddition reaction. The detection agent can be a biotin moiety, which allows recruitment of a variety of avidin- or streptavidin-linked secondary detection agents, including fluorescent dyes and enzymes that can convert substrates to give a detectable signal.

In one embodiment, the present method is applied to label or detect a glycan in a biological sample. Exemplary biological samples include tissue samples or bodily fluid samples. The sample can be a tumor biopsy sample, a blood, plasma, or serum sample, lymphatic fluid, saliva, a lung aspirate, a nipple aspirate, breast duct lavage sample, a pelvic lavage sample, a swab or scraping, etc. In some embodiments, the samples include whole cells (e.g., tumor cells or blood cells).

In one embodiment, the detection agent is a biotin moiety. When the detection agent is a biotin moiety, it can be used to noncovalently recruit a number of secondary detection agents, including, for example, enzymes capable of making reacting with fluorogenic, chemiluminescent, calorimetric products. The biotin is also useful for affinity chromatography using streptavidin/avidin conjugated to sepharose/agarose. Affinity enrichment allows for the enrichment of glycopeptides present in low cellular abundance. Fucose-α(1-2)-galactose containing peptides can be challenging to detect by mass spectrometry in the absence of enrichment strategies. According to some embodiments, biological mixtures, such as cell lysates, can be labeled with the labeling agent having a formula I, II or III. Such biological mixtures can then be: digested with protease such as trypsin, captured glycopeptides using monomeric avidin conjugated to agarose, eluted the glycopeptides and identified the peptides by LC-MS. Accordingly, a protein having a fucose-α(1-2)-galactose moiety in a nuclear lysate, can be labeled using the methods of the present invention with a ketone or azide reactive group-containing labeling agent and reacted with a biotin derivative. The labeled protein can then be detected by blotting with streptavidin-HRP. Such procedures can allow for high-throughput identification of the fucose-α(1-2)-galactose proteome. Another advantage of the streptavidin-agarose is that intact glycoproteins can be isolated. This procedure can be useful for rapid and fairly high-throughput detection by Western blotting (e.g., label proteins, isolate fucose-α(1-2)-galactose glycosylated proteins, and then probe the Western blot with antibodies against proteins of interest. This procedure can circumvent developing ways to immunoprecipitate or purify each protein of interest.). This procedure can also be used in conjunction with chromatin immunoprecipitation (CHIP assays) protocols to identify the genes regulated by post-translationally modified transcription factors.

One approach capitalizes on the substrate tolerance of glycosyltransferases, which allows for chemoselective installation of a non-natural functionality, such as a ketone or azide reactive group, to fucose-α(1-2)-galactose moiety on modified proteins (FIG. 1A).

Human blood group A antigen glycosyltransferase or bacteria homologue thereof has been shown to tolerate unnatural substrates containing substitutions at one or more positions on the sugar ring (e.g., the C-2 position). Enzyme design to enlarge binding pockets to accommodate altered substrates for these glycosyltransferases is contemplated. Generally, the binding pocket for the glycosyltransferase is identified, for instance, through crystal structure analysis. Then, the individual residues of the binding pocket of the glycosyltransferase can be mutated. Through homology modeling, the binding pocket of the mutated glycosyltransferase can be envisioned. Further modeling studies can explore binding of substrates in the binding pocket of the mutated glycosyltransferase. An exemplary mutated enzyme would enlarge the binding pocket of the enzyme and/or enhance the catalytic activity toward substrates without compromising specificity.

In general, a novel chemoenzymatic strategy that detects a glycosyl group comprising a fucose linked to a galactose with a high efficiency and sensitivity is disclosed. A variety of applications, including direct fluorescence detection, affinity enrichment, and isotopic labeling for comparative proteomics, is also contemplated.

The present invention therefore provides a labeled protein obtained by the methods described above. For example, a composition comprising a labeled protein substantially free of unlabeled protein can be made from the processes described in the specification.

Specifically, in some embodiments, the labeled protein comprises two glycosyl groups linked together. The first glycosyl group is a glycosyl group comprising a fucose linked to a galactose. The second glycosyl group is a glycosyl group covalently linked to the first glycosyl group. The second glycosyl group can be covalently linked to the first glycosyl group at any positions. For example, the second glycosyl group can be covalently linked to the fucose group on the first glycosyl group, or via the galactose on the first glycosyl group. In some embodiments, the first glycosyl group is covalently linked to the first glycosyl group at C-3 position of galactose on the first glycosyl group.

The second glycosyl group can be any sugar suitable for covalently conjugating with the first glycosyl group. In some embodiments, the second glycosyl group comprises a reactive group. In some embodiments, the second glycosyl group is a modified galactose, e.g., a GalNac. In some embodiments, the labeled protein has a formula of

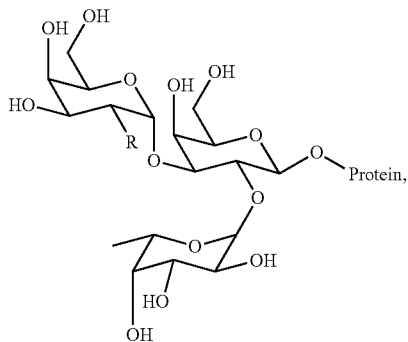

wherein R is a substituent comprising a reactive group, e.g., carbonyl group, azide group, nitril oxide group, diazoalkane group, alkyne group, and olefin group. In some embodiments, the labeled protein has a formula of

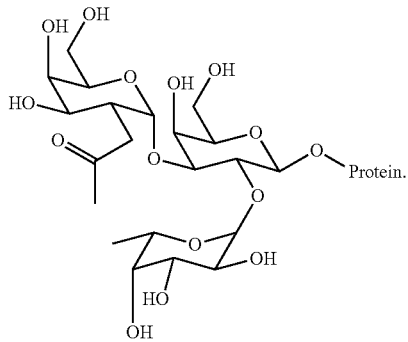

In some embodiments, the labeled protein has a formula of

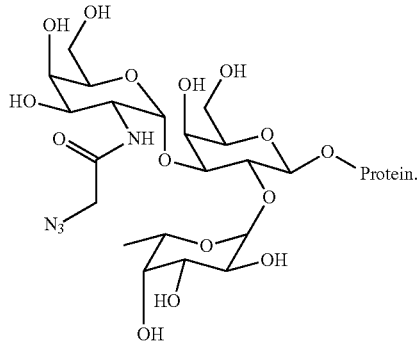

In some embodiments, the labeled protein further comprises a detection agent covalently linked to the second glycosyl group. For example, the detection agent can be covalently linked to the second glycosyl group via a reaction between the reactive group on the second glycosyl group and a coupling moiety on the detection agent. In some embodiments, the detection agent is biotin or biotin derivative. In some embodiments, the labeled protein has a formula of

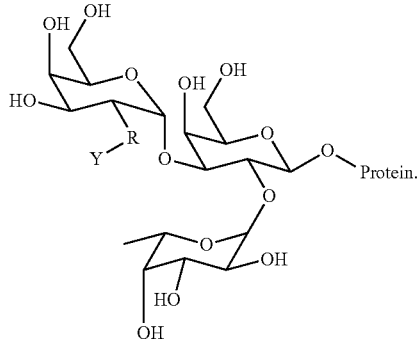

Y is the detection agent covalently linked to the second glycosyl group via the reaction between the reactive group on the second glycosyl group and the coupling moiety on the detection agent. In some embodiments, the labeled protein has a formula of

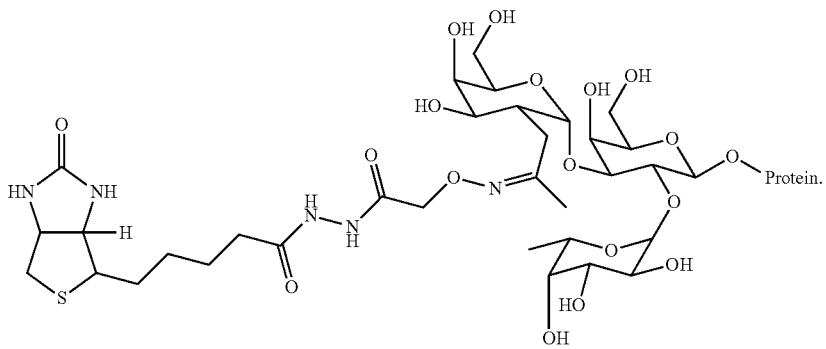

In some embodiments, the labeled protein has a formula of

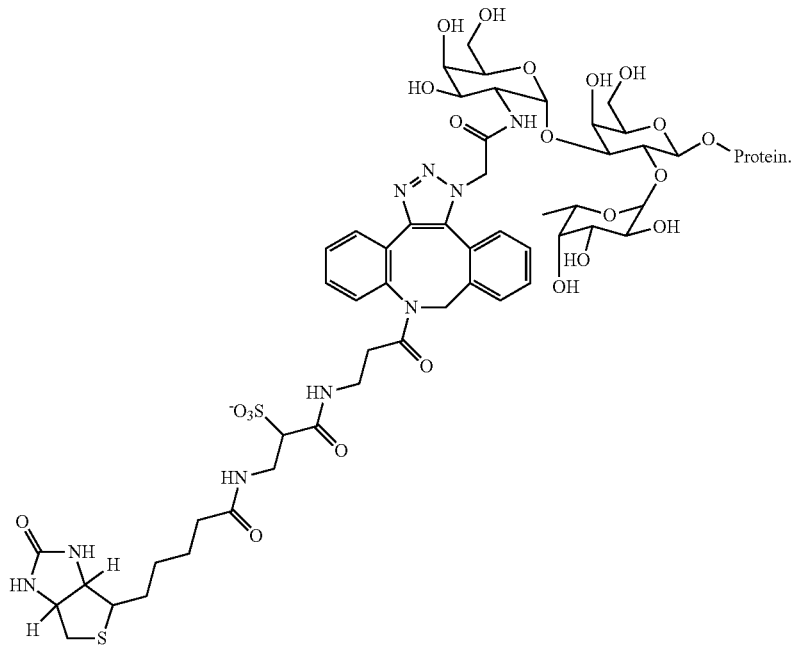

In some embodiments, the labeled protein further comprises an additional agent recruited by the detection agent as described herein. Exemplary additional agents include a secondary labeling agent, an enzyme, and a secondary detection agent. The additional agent can be non-covalently attached or covalently linked to the detection agent.

The present invention also provides a reaction mixture comprising (1) a glycan (e.g., a glycoprotein) with a glycosyl group comprising a fucose linked to a galactose, and (2) a labeling agent comprising a transferable glycosyl group recognized by a transferase capable of transferring the transferable glycosyl group to the glycan. In some embodiments, the transferable glycosyl group comprises a reactive group. In some embodiments, the reactive group is capable of reacting with a coupling moiety on a detection agent to form a covalent bond.

In some embodiments, the mixture further comprises a detection agent as described herein. In some embodiments, the detection agent comprises a coupling moiety that is capable of reacting with the reactive group on the labeling agent to form a covalent bond.

In some embodiments, the mixture further comprises a glycosyltransferase as described herein. In some embodiments, the glycosyltransferase is specific for a glycosyl group comprising a fucose linked to a galactose and is capable of catalyzing the transfer of the transferable glycosyl group on the labeling agent to the glycosyl group comprising a fucose linked to a galactose. In some embodiments, the glycosyltransferase is a glycosyltransferase specific for a fucose-α(1-2)-galactose group. For example, the glycosyltransferase can be a human blood group A antigen glycosyltransferase or a variant or fragment thereof, e.g., a bacteria homologue of the human blood group A antigen glycosyltransferase (BgtA) or a variant or fragment thereof.

In some embodiments, the mixture further comprises a secondary agent as described herein. For example, the secondary agent can be a secondary labeling agent, an enzyme, or a secondary detection agent. In some embodiments, the secondary agent is an agent that can be recruited by the detection agent. Exemplary secondary detection agents include fluorescent reagent, enzymatic reagent capable of converting substrates colorimetrically or fluorometrically, fluorescent and luminescent probe, metal binding probe, protein-binding probe, probe for antibody-based binding, radioactive probe, photocaged probe, spin-label or spectroscopic probe, heavy-atom containing probe, polymer containing probe, probe for protein cross-linking, and probe for binding to particles or surfaces that contain complementary functionality.

The present invention further provides a kit for labeling (e.g., detecting) a glycan (e.g., a glycoprotein) with a glycosyl group comprising a fucose linked to a galactose as described herein. In some embodiments, the kit comprises a glycosyltransferase specific for a glycosyl group comprising a fucose linked to a galactose, e.g., a glycosyltransferase is specific for a fucose-α(1-2)-galactose group. The glycosyltransferase is capable of catalyzing the transfer of a labeling agent to the glycan. Glycosyltransferases useful for the present invention are described herein. Exemplary glycosyltransferases include a human blood group A antigen glycosyltransferase or a variant or fragment thereof, e.g., a bacteria homologue of the human blood group A antigen glycosyltransferase (BgtA) or a variant or fragment thereof. In some embodiments, the kit further comprises instructions instructing a user to perform the detection. In some embodiments, the kit can be used for detecting cancer.

In some embodiments, the kit further comprises a labeling agent as described herein. In some embodiments, the labeling agent is an agent comprising a reactive group and a transferable glycosyl group recognized by the transferase. Where desired, the reactive group is located on the transferable glycosyl group.

In some embodiments, the kit further comprises a detection agent as described herein. In some embodiments, the detection agent comprises a coupling moiety capable of reacting with the reactive group on the labeling agent to form a covalent bond. Exemplary detection agents include fluorescent reagent, enzymatic reagent capable of converting substrates calorimetrically or fluorometrically, fluorescent and luminescent probe, metal-binding probe, protein-binding probe, probe for antibody-based binding, radioactive probe, photocaged probe, spin-label or spectroscopic probe, heavy-atom containing probe, polymer containing probe, probe for protein cross-linking, and probe for binding to particles or surfaces that contain complementary functionality.

In some embodiments, the kit further comprises a storage buffer. The storage buffer can comprise a stabilizer such as bovine serum albumin, gelatin, glycerol, sodium azide, tris, or a combination thereof.

In some embodiments, the kit further comprises a separation device for purifying a target glycan (e.g., a target glycoprotein) before labeling, and/or for purifying a labeled target glycan. Methods for purifying glycan (e.g., glycoprotein) are known in the art, non-limiting examples of which include protein A-based affinity chromatography, size-exclusion chromatography, and ultra membrane filtration. Exemplary separation devices include biotin affinity chromatography column. Commercial kits for protein purification, such as antibody cleaning kits, may also be used for target protein purification. Size-exclusion column chromatography and ultra membrane filtration are useful for removing stabilizers/preservatives of relatively small molecules, such as glycerol, Tris, and amino acids. Ultra membrane filtration may also be used to adjust target protein concentration to a desired value. Ultra membrane filtration can be conveniently and rapidly carried out on a centrifuge using a commercial ultra membrane filtration vial. The membranes in such ultra filtration devices typically have different pore sizes, or so-called Molecular Weight Cut-off sizes (MWCO), permitting relatively small molecules to go through while retaining bigger molecules, such as proteins. In some embodiments, a membrane with a MWCO of about, less than about, or more than about 1, 5, 10, 15, 20, 25, 50, 100, or more kD is provided to purify a target protein before and/or after labeling. Columns for size exclusion chromatography typically comprise particles or beads having pores of a particular MWCO. Particles larger than the MWCO pass through the column faster than particles at or below the MWCO. In some embodiments, a column with a MWCO of about, less than about, or more than about 1, 2, 10, 15, 20, 25, 50, 100, or more kD is provided to purify a target protein before and/or after labeling.

In some embodiments, the kit further comprises a stain stabilizing reagent for enhancing dye fluorescence, such as by enhancing fluorescent intensity or reducing a rate of decrease in fluorescent intensity. Stain stabilizing reagents are known in the art, non-limiting examples of which include EverBrite (Biotium), Vectashield (Vector Laboratories), and SlowFade Gold (Invitrogen). In some embodiments, fluorescent intensity of a dye in the presence of the stain stabilizing reagent is increased by at least about 10%, 20%, 30%, 40%, 50%, 60%, 70%, 80%, 90%, 100%, 150%, 200%, 300%, 400%, 500% or more above the intensity of the dye in the absence of the stain stabilizing reagent. In some embodiments, fluorescent intensity of a dye in the presence of the stain stabilizing reagent is maintained above a threshold level for a time that is at least about 0.5, 1, 2, 3, 4, 5, 6, 7, 8, 9, 10, 15, 20, 25, 30, 35, 40, 45, 50, 55, 60, or more minutes. In some embodiments, the threshold level is at least about 10%, 20%, 30%, 40%, 50%, 60%, 70%, 75%, 80%, 85%, 90%, 95%, 96%, 97%, 98%, 99%, 99.5%, or more of the starting fluorescent intensity.

In some embodiments, the kit further comprises a detectable label such as a radio-opaque label, nanoparticle, PET label, MRI label, radioactive label, and the like.

The present invention further provides a method of identifying a glycan (e.g., a glycoprotein) comprising a fucose linked to a galactose. The method comprises the steps of 1) providing one or more homogenous population of glycans; 2) contacting a glycosyl transferase with the glycans in the presence of a labeling agent comprising a transferable glycosyl group, wherein the transferable glycosyl group comprises a reactive group, wherein the glycosyl transferase is specific for the glycosyl group comprising a fucose linked to a galactose and catalyzes the transfer of the transferable glycosyl group to the glycosyl group comprising a fucose linked to a galactose; 3) contacting the glycans with a detection agent, wherein the reactive group on the labeling agent is capable of reacting with a coupling moiety on the detection agent to form a covalent bond; and 4) identifying a glycan having the covalently bound detection agent via the reactive group on the transferred glycosyl group as the glycan comprising a fucose linked to a galactose.

In some embodiments, the glycans are covalently or non-covalently attached to a solid support. In some embodiments, the glycans are attached to the solid support in the form of an array. In some embodiments, the array comprises two or more addressable locations. Each addressable location may comprise a homogenous population of glycans displaying different carbohydrate sequences.

In some embodiments, arrays of glycans are formed on a substrate. Glycan molecules can be arranged directly on a substrate for use in, for example, the identification of one or more glycans, e.g., a glycan comprising a fucose linked to a galactose. The glycan molecules can be attached to the substrate via linkers, using methods well known in the art and as described herein. Alternatively, the glycan molecules can be synthesized directly on the substrate. In some embodiments, glycan molecules are non-covalently attached to PLL coated substrates, or glass slides. Antibodies to specific glycan molecules can be used to determine that the array is composed of the desired glycan molecules.

In a typical array a substrate comprises one or more addressable locations of glycan molecules. The addressable locations can be directly adjacent to each other or can be physically separated by a gap or a barrier.

In some embodiments, each addressable location comprises one type of glycan molecule or more than one type of glycan molecules. Glycan molecules may differ in the length of the oligosaccharide chains or may also differ as different subtypes of glycan molecules.

In the case where each location comprises a single type of glycan molecule, the number of locations on the array of glycan molecules is at least as great as the number of different types of glycan molecules to be used. In one embodiment, each addressable location comprises at least about $10^5$ glycan molecules.

In some embodiments, the particular location of a particular type of glycan molecule is not predetermined. The identity of the glycan can be determined using the methods described herein. In some embodiments, the glycan molecule composition and physical location of each addressable location is known. In one embodiment, each of the addressable locations in the array comprises a different type of glycan molecule. For example, if a target protein is to be assayed for its ability to bind various types of glycans containing a fucose linked to a galactose, the array may comprise multiple addressable locations, each comprising a different type of glycan molecule containing a fucose linked to a galactose. In an alternative embodiment, more than one addressable location comprising a particular type of glycan molecule is present.

The overall size of the array is not limited and will be determined based on a variety of factors, including the number of glycan molecules in each addressable locations, the number of addressable locations and the physical nature of the solid support on which the array is formed.

In some embodiments, a glycan microarray can be created using a general, highly efficient strategy for attaching glycans to the array surface, details of which are provided in Tully, S. E. et al., *J. Am. Chem. Soc.* (2006) 128:7740-7741; Gama, C. I. et al., *Nature Chemical Biology* (2006) 2(9): 467-473; and Shipp, E. L. and Hsieh-Wilson, L. C., *Chemistry & Biology* (2007) 14:195-208; each of which are incorporated herein by reference in its entirety. Briefly, glycan molecules are synthesized with an allyl functionality on the reducing end of the sugar. This group is stable to the chemical manipulations used to synthesize the oligosaccharides, yet it can be readily functionalized for surface conjugation.

In a particular embodiment, solutions of aminooxy oligosaccharides in buffer (for example, 300 mM $NaH_2PO_4$, pH 5.0) can be arrayed on slides, such as Hydrogel Aldehyde slides (NoAb Biodiscoveries) by using a robotic arrayer, such as a Microgrid 11 arrayer (Biorobotics), to deliver sub-nanoliter volumes. In one embodiment, for example, spots are approximately 1 to 1000 μm, in some embodiments 1 to 500 μm and in some embodiments about 100-200 μm in diameter. In some embodiments, concentrations of carbohydrates range from 0-1000 μM. The resulting arrays can be incubated in a 70% humidity chamber at room temperature overnight and then stored in a low humidity, dust-free dessicator prior to use.

Importantly, this strategy requires minimal manipulation of the glycan, enabling their direct conjugation in two short, high-yielding steps. Moreover, the approach is compatible with standard DNA robotic printing and fluorescence scanning technology, which requires only minimal amounts of material and allows a large number of molecular interactions to be probed simultaneously.

An exemplary glycan array is the printed glycan array provided by the Consortium for Functional Glycomics (www.functionalglycomics.org). The printed array uses a library of natural and/or synthetic glycans printed on to glass microscope slides. One or more glycosyl transferases, labeling agents, and detection agents can be added to the array in conditions where the transferable glycosyl group on the labeling agent may be transferred to the glycan having a glycosyl group comprising a fucose linked to a galactose. Other glycan arrays include for example the glycan array discussed in Liang et al. 2009 (*Expert Rev Proteomics.* 2009 December; 6(6):631-45) and Blixt et al. 2004 (*PNAS* 2004 101(49): pp 17033-17038), the contents of which are hereby incorporated by reference.

The glycan array may include at least one positive and at least one negative control. In some embodiments the glycan array may also include at least one background control. The use of positive, negative and background controls in arrays is well known in the art. A negative control is known to give a negative result. The negative control may be a molecule which is known not to have a glycosyl group comprising a fucose linked to a galactose. Alternatively the negative control may be created by the absence of a glycan bound to the solid support, i.e., so there is nothing for a candidate antibody to bind. The positive control confirms that the basic conditions of the experiment were able to produce a positive result. The positive control may be a molecule, e.g. a glycan, which is known to a glycosyl group comprising a fucose linked to a galactose (e.g., a fucose-α(1-2)-galactose group).

The present invention further provides a method of detecting cancer cells. The method comprises the steps of 1) contacting a cell with a glycosyltransferase and a labeling agent comprising a transferable glycosyl group as described herein, wherein the transferable glycosyl group comprises a reactive group, wherein the glycosyltransferase is specific for the glycosyl group comprising a fucose linked to a galactose and catalyzes the transfer of the transferable glycosyl group to the glycosyl group comprising a fucose linked to a galactose; 2) contacting the cell comprising the transferred labeling agent with a detection agent, wherein the reactive group on the labeling agent reacts with a coupling moiety on the detection agent to form a covalent bond; and 3) detecting the amount of the detection agent covalently bound to the cell via the reactive group on the transferred labeling agent.

In some embodiments, the method further comprises 4) comparing the amount of the detection agent covalently bound to the cell to the amount of the detection agent covalently bound in a non-cancerous control. An increase (e.g., 10%, 20%, 30%, 40%, 50%, 60%, 70%, 80%, 90%, 100%, 200%, 300% or more) in the amount of the detection agent covalently bound to the cell from the tissue sample as compared to the amount of the detection agent covalently bound in a non-cancerous control indicates a presence of cancer cell having the glycosyl group comprising a fucose linked to a galactose. An amount of the detection agent covalently bound to the cell from the tissue sample that is comparable to the amount of the detection agent covalently bound in a non-cancerous control indicates an absence of cancer cell having the glycosyl marker group comprising a fucose linked to a galactose.

In some embodiments, the method further comprises 4) comparing the amount of the detection agent covalently bound to the cell to the amount of the detection agent covalently bound in a cancerous positive control. An amount of the detection agent covalently bound to the cell from the tissue sample that is comparable to the amount of the detection agent covalently bound in a cancerous positive control indicates a presence of cancer cell having the glycosyl group comprising a fucose linked to a galactose. A decrease (e.g., 10%, 20%, 30%, 40%, 50%, 60%, 70%, 80%, 90% or more) in the amount of the detection agent covalently bound to the cell from the tissue sample as compared to the amount of the detection agent covalently bound in a cancerous positive control indicates an absence of cancer cell having the glycosyl group comprising a fucose linked to a galactose.

Various cancer cells can be detected using the method described herein. The cells can be cultured cell or cells from a tissue sample of a subject. Expression levels of a glycosyl group comprising a fucose linked to a galactose (e.g., a fucose-α(1-2)-galactose group) are linked to (e.g., up-regulated) various cancers, e.g., breast cancer (e.g., highly invasive breast cancer), lung cancer (e.g., small cell lung cancer), prostate cancer, colon cancer, colorectal cancer, cervical cancer, and pancreatic cancer. Using the method described herein, these cancer cells can be detected.

The unique glycan biomarker also enables more efficient drug development through the discovery of protein targets associated with the glycan marker. In addition, the unique glycan biomarker as described herein can serve as a basis for novel diagnostics, including companion diagnostics. Examples of proteins or lipids associated with fucose-α(1-2)

galactose in cancers include prostate specific antigen (PSA), Globo H antigen (a glycosphingolipid upregulated in breast cancer), and CD44v6 (colon cancer).

The present invention further provides diagnostic methods for detection cancer. In some embodiments, the compositions and methods described herein can be used for in vivo or ex vivo diagnosis of cancer. For these diagnostic applications, the labeling agent and/or detection agent can comprise a detectable label or an epitope tag that is capable of binding to a detectable label. Suitable detectable labels include, but are not limited to radio-opaque labels, nanoparticles, PET labels, MRI labels (e.g., gadolinium-containing contrast agents, iron oxide, manganese, and iron platinum), radioactive labels (e.g., C14 label), and the like. Among the radionuclides useful in various embodiments of the present invention, gamma-emitters, positron-emitters, x-ray emitters and fluorescence-emitters are suitable for localization, diagnosis and/or staging, and/or therapy, while beta and alpha-emitters and electron and neutron-capturing agents, such as boron and uranium, also can be used for therapy.

The detectable labels can be used in conjunction with an external detector and/or an internal detector and provide a means of effectively localizing and/or visualizing cancer cells associated with fucose-α(1-2) galactose. Such detection/visualization can be useful in various contexts including, but not limited to pre-operative and intraoperative settings. Thus, in certain embodiment this invention relates to a method of intraoperatively detecting and cancers (e.g., breast cancer, lung cancer, prostate cancer, colon cancer, colorectal cancer, cervical cancer, and pancreatic cancer) in the body of a mammal.

The examples disclosed below illustrated preferred embodiments and are not intended to limit the scope. It would be obvious to those skilled in the art that modifications or variations may be made to the preferred embodiments described herein without departing from the teachings of the present invention.

Example 1: Chemoenzymatic Probes for Detecting and Imaging Fucose-α(1-2)-Galactose Glycans Biomarkers Here we report a new chemoenzymatic strategy for the rapid, sensitive, and selective detection of Fucα(1-2)Gal glycans. We demonstrate that the approach is highly selective for the Fucα(1-2)Gal motif, detects a variety of complex glycans and glycoproteins, and can be used to profile the relative abundance of the motif on live cells, discriminating malignant from normal cells. This approach represents a new potential strategy for biomarker detection and expands the technologies available for understanding the roles of this important class of carbohydrates in physiology and disease.

Our approach capitalizes on the substrate tolerance of a bacterial glycosyltransferase to covalently tag specific glycans of interest with a non-natural sugar analog. As the reaction proceeds in quantitative yield, stoichiometric addition of the non-natural sugar can be achieved, affording higher detection sensitivity relative to antibodies, lectins, and metabolic labeling. Although chemoenzymatic approaches have been reported for two saccharides, O-linked-β-N-acetylglucosamine (O-GlcNAc) ((a) Khidekel, N.; Arndt, S.; Lamarre-Vincent, N.; Lippert, A.; Poulin-Kerstien, K. G.; Ramakrishnan, B.; Qasba, P. K.; Hsieh-Wilson, L. C. *J. Am. Chem. Soc.* 2003, 125, 16162. (b) Clark, P. M.; Dweck, J. F.; Mason, D. E.; Hart, C. R.; Buck, S. B.; Peters, E. C.; Agnew, B. J.; Hsieh-Wilson, L. C. *J. Am. Chem. Soc.* 2008, 130, 11576.) and N-acetyllactosamine (LacNAc), (Zheng, T.; Jiang, H.; Gros, M.; Soriano del Amo, D.; Sundaram, S.; Lauvau, G.; Marlow, F.; Liu, Y.; Stanley, P.; Wu, P. *Angew. Chem. Int. Ed.* 2011, 50, 4113.) this study demonstrates the first direct detection of complex oligosaccharides, opening up the potential to track a broad range of physiologically important glycans.

Figure 5:
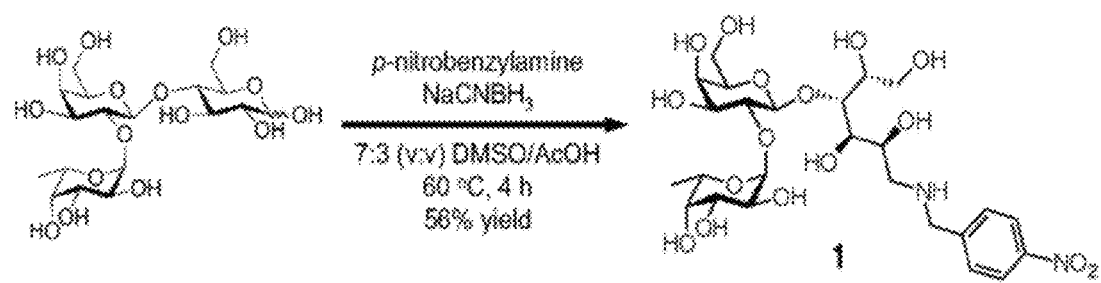
FIG. 5. Synthesis of Fucα(1-2)Gal substrate 1.
Figure 6:
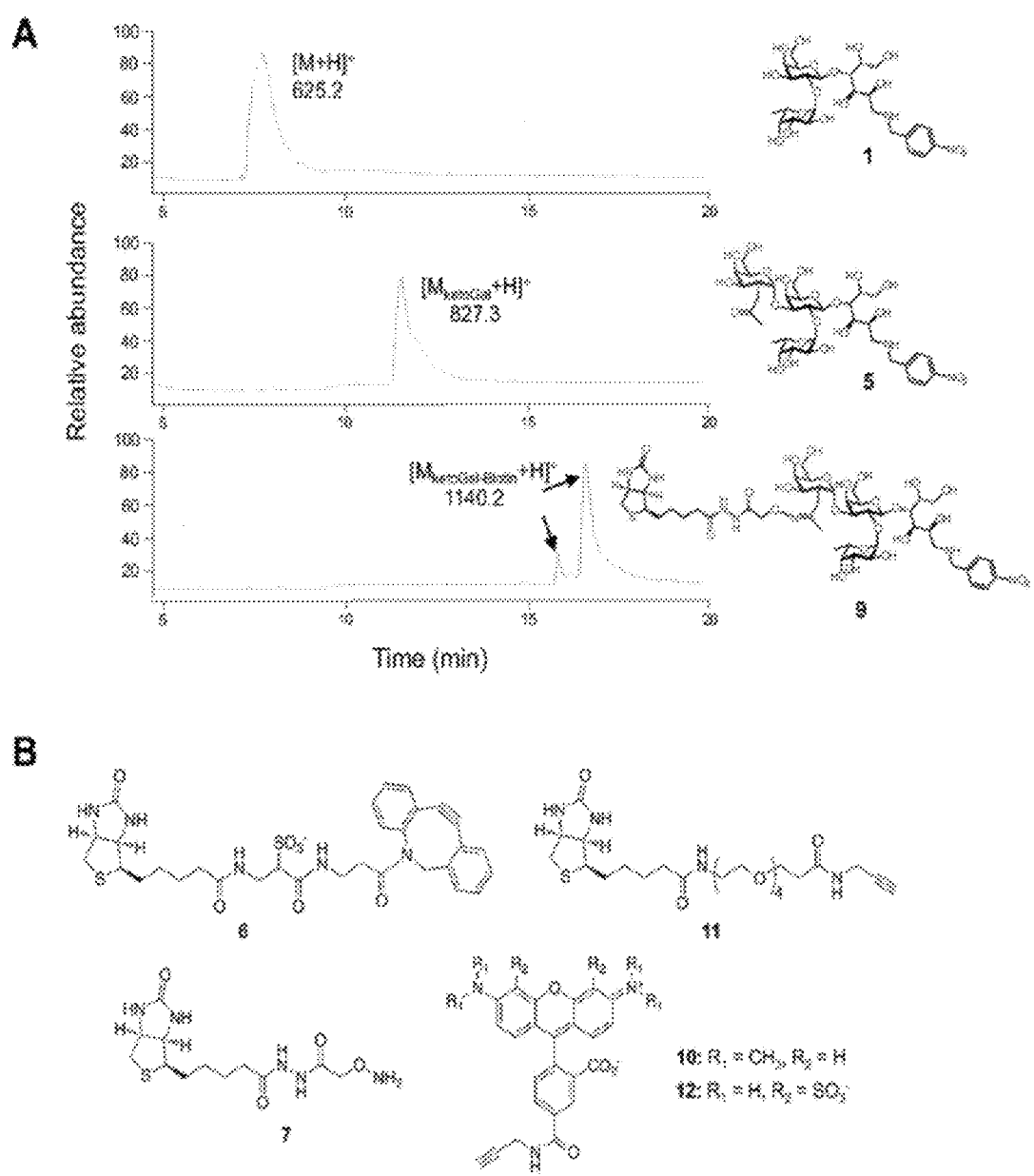
FIG. 6. (A) Chemoenzymatic labeling of substrate 1 with UDP-ketoGal 3. LC-MS analysis of the reaction progress at time 0 (top), 12 h after the addition of BgtA and 3 (middle), and 24 h after the addition of aminooxy-biotin derivative 7 (bottom). See Materials and Methods for details. (B) Compounds used for chemoenzymatic labeling of glycans.
Figure 7:
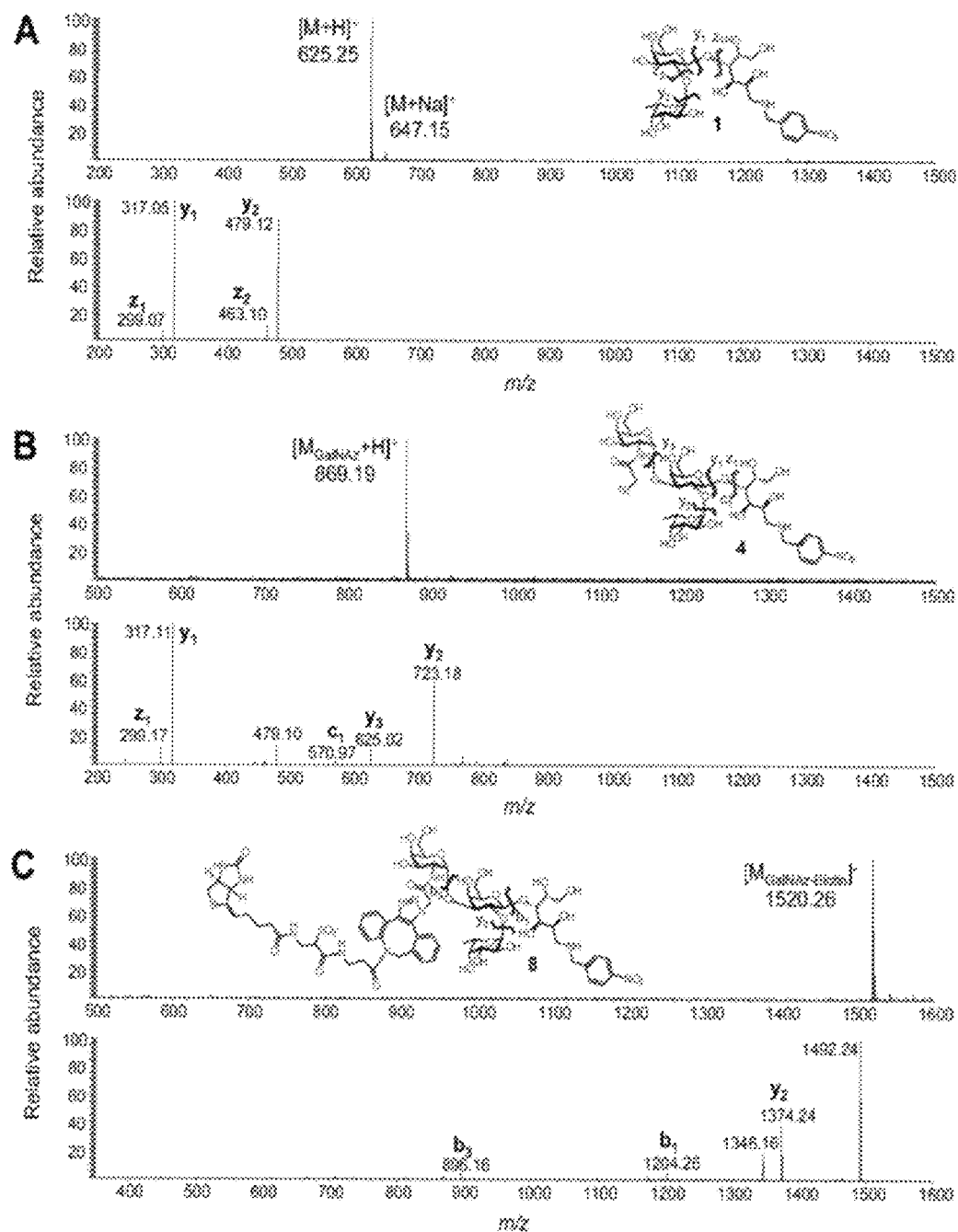
FIG. 7. LC-MS/MS analysis of 1, 4, and 8 during the chemoenzymatic labeling reaction. (A) Compound 1 at time 0. (B) Compound 4, generated 12 h after the addition of BgtA and UDP-GalNAz 2. (C) Biotinylated glycan 8, generated 3 h after reaction with ADIBO-biotin 6. The MS spectrum for each compound is shown on top; the MS/MS spectrum for the most abundant ion is shown on the bottom. The m/z of peaks found in each MS/MS analysis are shown as either b and y or c and z ions. The corresponding fragmentation products and probable cleavage sites are denoted in the respective structures. 1 and 4 were detected in positive scanning mode; 8 was detected in negative scanning mode.
Figure 8:
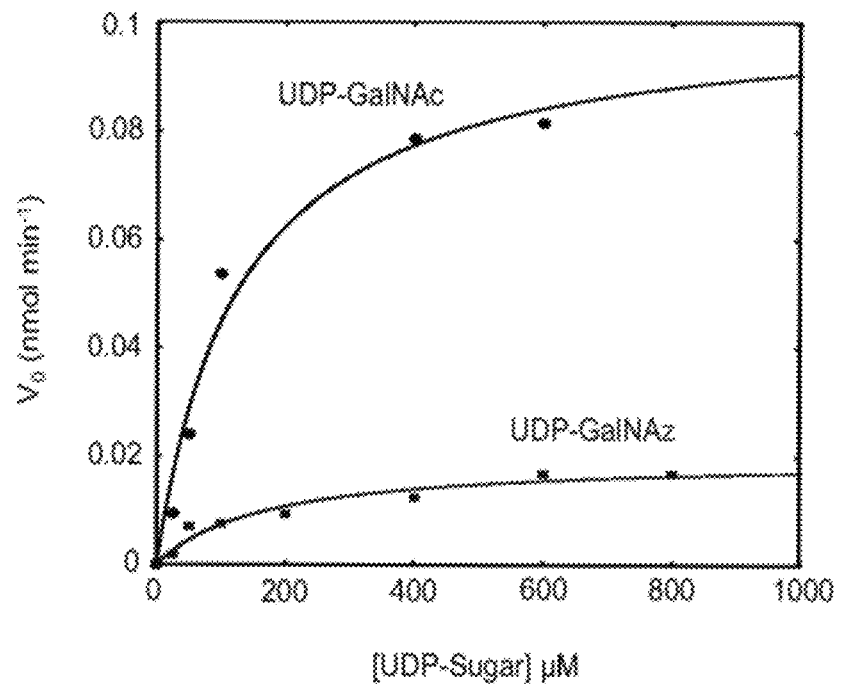
FIG. 8. Kinetic comparison of the BgtA-catalyzed reaction of 1 with UDP-GalNAc (black) and UDP-GalNAz (blue). Reactions were performed in duplicate using 100 μM of acceptor 1 and varying concentrations of the donor. Initial rates as a function of substrate concentration were plotted and revealed apparent $k_{cat}/K_m$ values of 5.7 nM$^{-1}$ min$^{-1}$ and 40.4 nM$^{-1}$ min$^{-1}$, respectively, and apparent $K_m$ values of 127±36 μM and 168±55 μM, respectively. The apparent $V_{max}$ value for UDP-GalNAc (0.100±0.010 nmol·min$^{-1}$) is approximately 5-fold higher than that of UDP-GalNAz (0.020±0.002 nmol·min$^{-1}$).

We exploited the bacterial homologue of the human blood group A antigen glycosyltransferase (BgtA), which has been shown to transfer N-acetylgalactosamine (GalNAc) from UDP-GalNAc onto the C-3 position of Gal in Fucα(1-2)Gal structures. (Yi, W.; Shen, J.; Zhou, G.; Li, J.; Wang, P. G. *J. Am. Chem. Soc.* 2008, 130, 14420.) We reasoned that BgtA might tolerate substitution at the C-2 position of GalNAc, which would allow for the selective tagging of Fucα(1-2) Gal with an azido or ketone functionality (FIG. 1A). To test the approach, Fucα(1-2)Gal substrate 1 was synthesized via reductive amination of 2'-fucosyllactose with p-nitrobenzylamine and sodium cyanoborohydride (FIGS. 1B and 5, Supporting Information (SI)). Indeed, treatment of 1 with BgtA and either UDP-N-azidoacetylgalactosamine (UDP-GalNAz, 2) or UDP-2-deoxy-2-(acetonyl)-β-D-galactopyranoside (UDP-ketoGal, 3) led to complete conversion to the desired products 4 and 5, respectively, after 12 h at 4° C., as determined by liquid chromatography-mass spectrometry (LC-MS; FIGS. 1B, 6 and 7, SI). Kinetic analysis revealed an apparent $k_{cat}/K_m$ value of 5.7 $nM^{-1}$ $min^{-1}$ for UDP-GalNAz, approximately 7-fold lower than the value of 40.4 $nM^{-1}$ $min^{-1}$ obtained for the natural UDP-GalNAc substrate (FIG. 8, SI). (Yi, W.; Shen, J.; Zhou, G.; Li, J.; Wang, P. G. *J. Am. Chem. Soc.* 2008, 130, 14420.) Subsequent reaction with an aza-dibenzo-cyclooctyne-biotin derivative (ADIBO-biotin, 6; FIG. 6, SI) using copper-free click chemistry (3 h, rt) or with the aminooxy-biotin derivative 7 (FIG. 6, SI; 24 h, rt) afforded the biotinylated products 8 and 9, respectively, in quantitative yield (FIGS. 1B, 6 and 7, SI).

Figure 2:
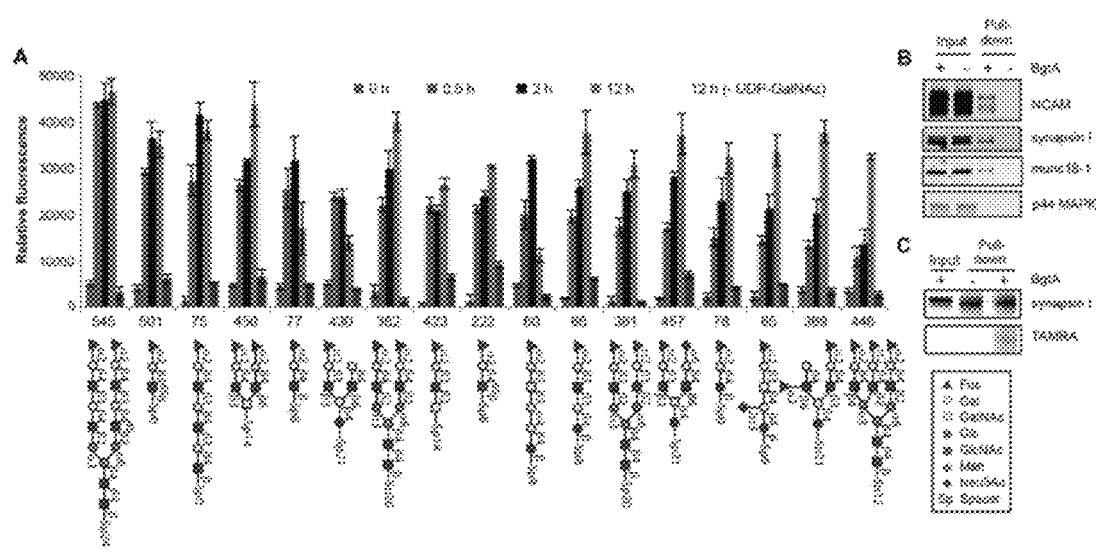
FIG. 2. (A) Time course analysis using glycan microarrays. Representative structures from the top 26 glycans with the highest relative fluorescence intensity after 0.5 h are plotted, all of which represent terminal Fucα(1-2)Gal structures. UDP-GalNAz was omitted from some of the reactions as a control (12 h, -UDP-GalNAz). (B) Chemoenzymatic detection of endogenous Fucα(1-2)Gal glycoproteins from neuronal lysates. (C) Chemoenzymatic detection of Flag-tagged synapsin I expressed in HeLa cells. See SI for experimental details.
Figure 9:
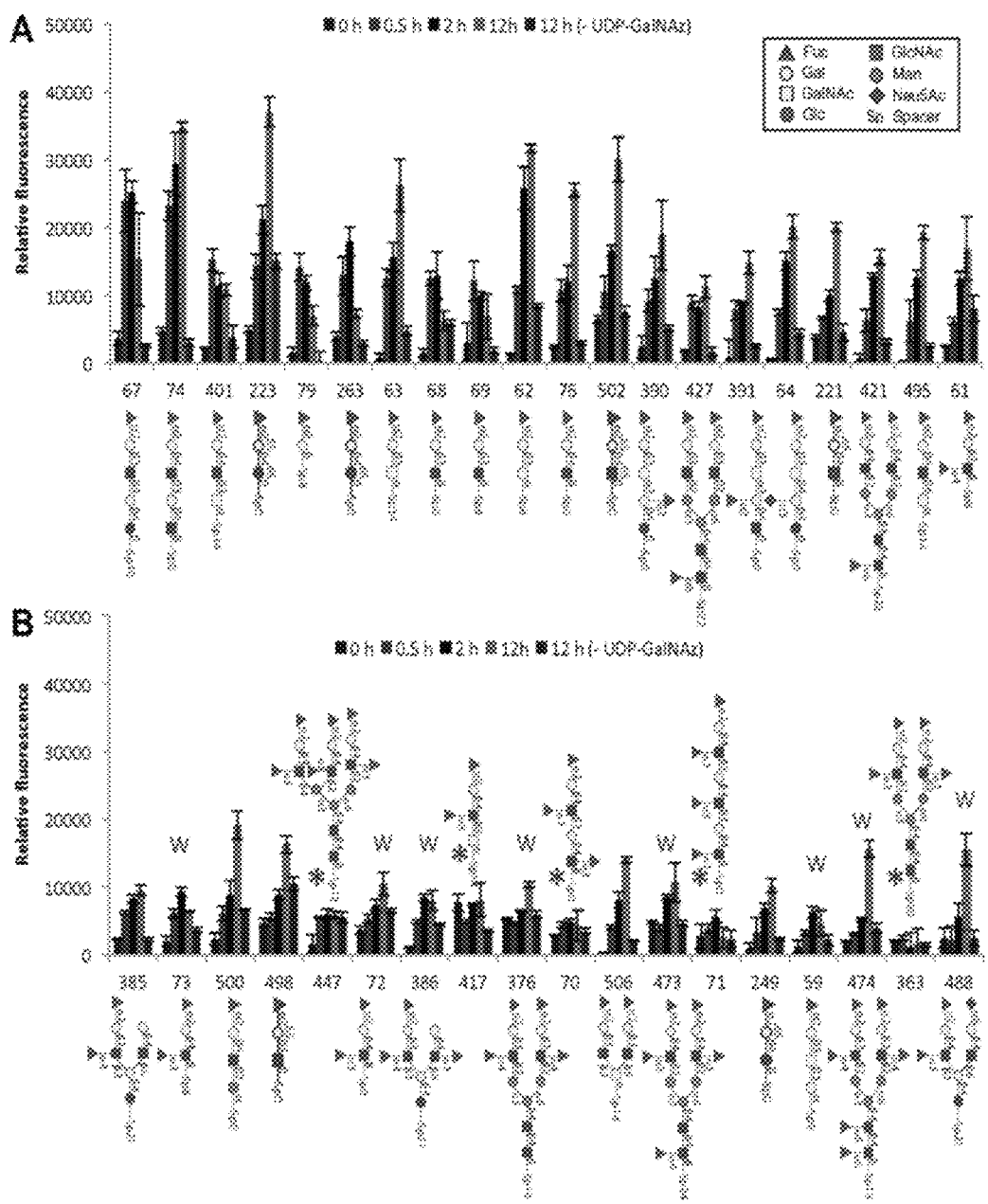
FIG. 9. Additional Fucα(1-2)Gal structures on the microarray and their ability to be labeled by BgtA (see also FIG. 2A). Relative fluorescence intensities are plotted as a function of time and represent the mean of 4 values. Error bars represent the standard deviation of the mean. Glycans were considered labeled if they showed a time-dependent increase in fluorescence labeling and their signal at 12 h after subtraction of the background in the absence of UDP-GalNAz (12 h, -UDP-GalNAz) was >1000 relative fluorescence units. The red asterisks indicate structures that were not considered to be labeled. W indicates very weak labeling.
Figure 10:
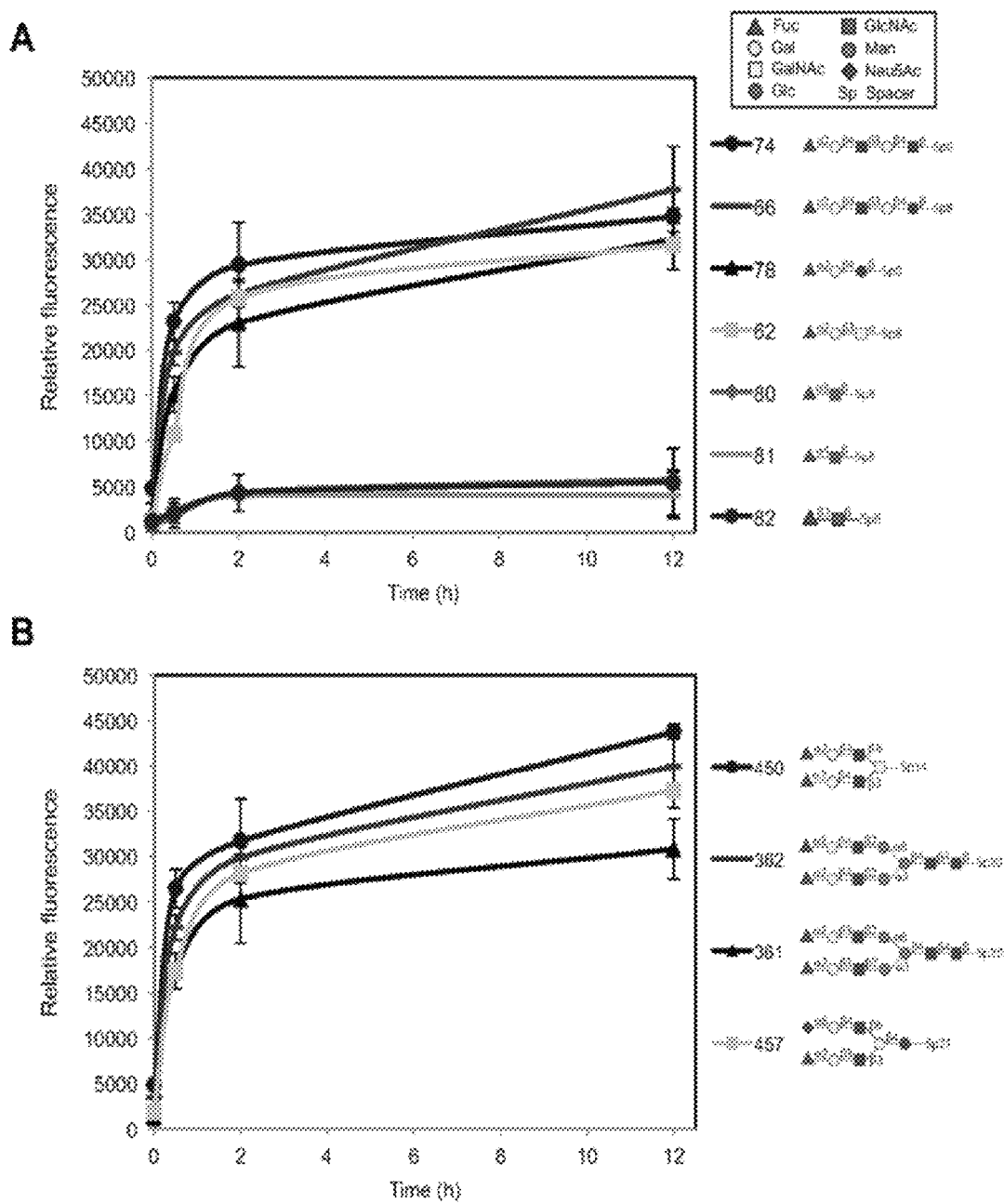
FIG. 10. The chemoenzymatic approach labels a variety of linear (A) and branched (B) Fucα(1-2)Gal structures. (A) The third sugar toward the reducing end of the glycan does not significantly affect the labeling reaction (eg. 62, 66, 74, and 78). Acceptor substrate structures that have a GlcNAc, instead of Gal, and change the linkage from α(1-2) to α(1-3), α(1-4), or β(1-3) are not modified by BgtA (eg 80, 81, and 82). Representative structures from the microarray are shown for comparison. Relative fluorescence intensities are plotted as a function of time to show how subtle changes in the structure affect the kinetics of labeling. Error bars represent the standard deviation of the mean of 4 values after removing the high and low values from n=6 replicates of each glycan printed on the array.

Having demonstrated that BgtA accepts non-natural substrates, we profiled the glycans detected by BgtA using carbohydrate microarrays from the Consortium for Functional Glycomics. ((a) Blixt, O.; Allin, K.; Bohorov, O.; Liu, X.; Andersson-Sand, H.; Hoffman, J.; Razi, N. *Glycoconjugate J.* 2008, 25, 59. (b) Blixt, O. et al. *Proc. Natl Acad. Sci. USA* 2004, 101, 17033.) Glycosylation reactions with BgtA and UDP-GalNAz were performed on 611 different glycans simultaneously at 3 different time points (0.5, 2 and 12 h). Following reaction with ADIBO-biotin, biotinylated glycans were detected using Cy5-conjugated streptavidin. Strong fluorescence labeling of Fucα(1-2)Gal structures was observed within 0.5 h (FIG. 2A). Notably, the top 26 glycans labeled contained terminal Fucα(1-2)Gal structures, highlighting the specificity of the chemoenzymatic approach. Moreover, ~91% of the terminal Fucα(1-2)Gal containing a free C-3 hydroxyl group on Gal were labeled on the array, including the H1 (68, 69) and H2 antigens (76, 77), the ganglioside Fuc-GM1 (65), and the Globo H antigen (60), a hexasaccharide overexpressed on breast, lung and prostate tumors ((b) Chang, W.-W.; Lee, C. H.; Lee, P.; Lin, J.; Hsu, C.-W.; Hung, J.-T.; Lin, J.-J.; Yu, J.-C.; Shao, L.-e.; Yu, J.; Wong, C.-H.; Yu, A. L. *Proc. Natl Acad. Sci. USA* 2008, 105, 11667. (c) Menard, S.; Tagliabue, E.; Canevari, S.; Fossati, G.; Colnaghi, M. I. *Cancer Res.* 1983, 43, 1295. (d) Zhang, S.; Zhang, H. S.; Cordon-Cardo, C.; Ragupathi, G.; Livingston, P. O. *Clin. Cancer Res.* 1998, 4, 2669. (e) Miyake, M.; Taki, T.; Hitomi, S.; Hakomori, S.-i. *N. Engl. J. Med.* 1992, 327, 14.) and associated with poor prognosis (FIGS. 2A and 9, SI). ((e) Miyake, M.; Taki, T.; Hitomi, S.; Hakomori, S.-i. *N. Engl. J. Med.* 1992, 327, 14. (f) Colnaghi, M. I.; Da Dalt, M. G.; Agresti, R.; Cattoretti, G.; Andreola, S.; Di Fronzo, G.; Del Vecchio, M.; Verderio, L.; Cascinelli, N.; Rilke, F. In Immunological Approaches to the Diagnosis and Therapy of Breast Cancer; Ceriani, R. L., Ed.; Plenum Publishing: New York, 1987, 21.) A wide variety of linear (e.g., 501, 75, and 60) and branched structures (e.g., 450, 362, and 457) containing the Fucα(1-2)Gal motif were efficiently labeled (FIGS. 2A and 10, SI). Modifications of the core disaccharide, such as replacing Gal with GlcNAc, or changing the α(1-2) linkage to an α(1-3), α(1-4) or β(1-3) linkage eliminated the enzymatic labeling by BgtA (e.g., 80, 81, and 82; FIG. 10, SI).

Figure 11:
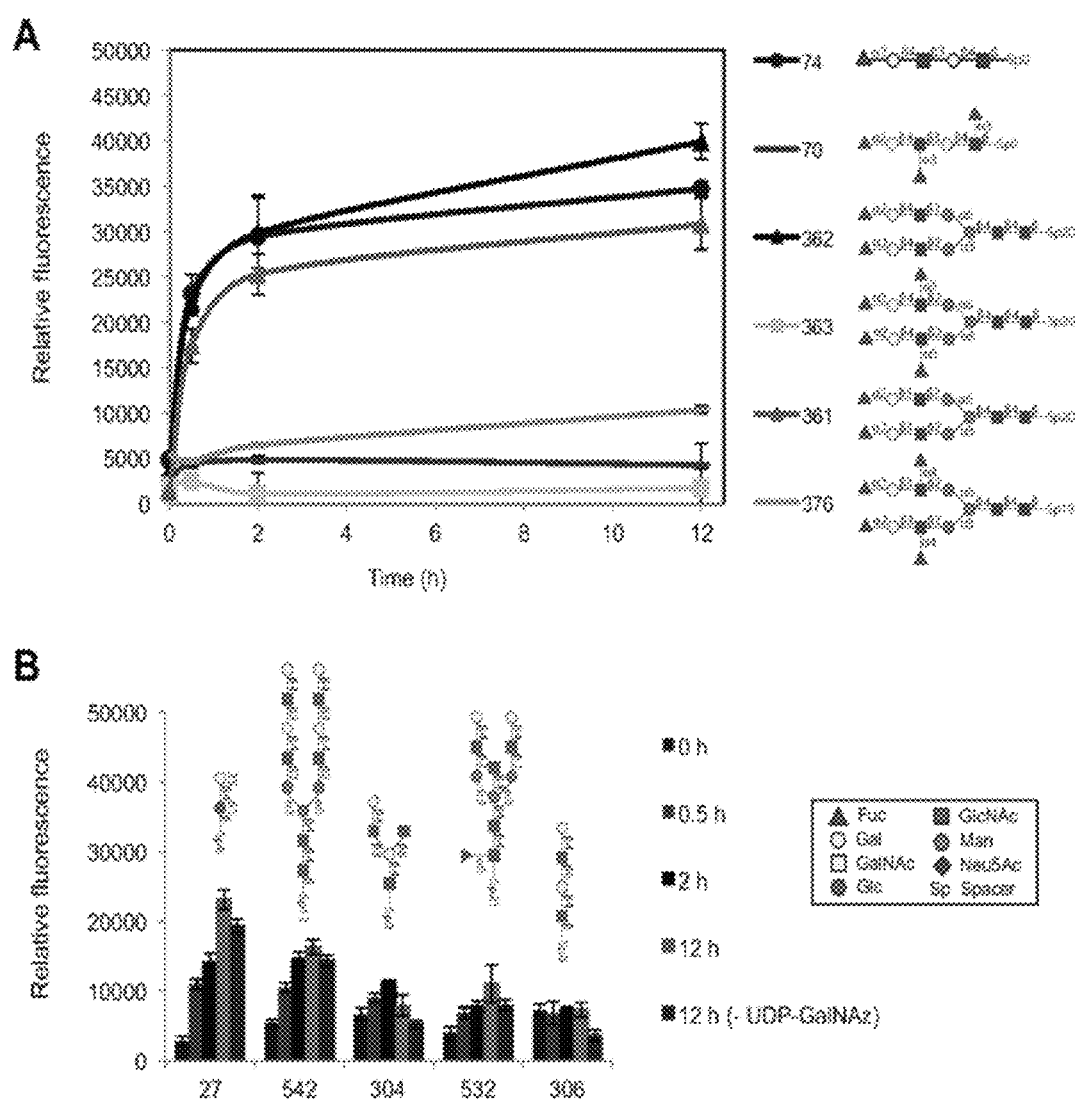
FIG. 11. The chemoenzymatic approach labels a variety of Fucα(1-2)Gal structures. (A) Branching at the third position GlcNAc via α(1-3) or α(1-4) fucosylation severely hindered the labeling efficiency. (B) Weak labeling of Galβ(1-4)GlcNAc structures was also observed. This labeling was accompanied by high background, as indicated by the 12 h time point in the absence of UDP-GalNAz. No labeling of these structures was observed in solution, suggesting that the labeling was likely due to non-covalent interactions with the microarray. Representative structures are shown for comparison. Relative fluorescence intensities are plotted as a function of time to show how changes in glycan structure affect the labeling reaction. Error bars represent the standard deviation of the mean of 4 values after removing the high and low values from n=6 replicates of each glycan printed on the array.

Consistent with a previous report, (Yi, W.; Shen, J.; Zhou, G.; Li, J.; Wang, P. G. *J. Am. Chem. Soc.* 2008, 130, 14420.) BgtA exhibited more relaxed specificity toward structures appended to the reducing end of the Gal residue. Specifically, glycans containing a β(1-3)GalNAc, β(1-3)GlcNAc, β(1-4)GlcNAc, or β(1-4)Glc in this position were efficiently labeled (e.g., 62, 66, 74, and 78, respectively; FIGS. 2A and 9, SI). Although moderate structural substitutions of the GlcNAc were tolerated such as 6-O-sulfation (e.g., 501 and 222; FIG. 2A), branching at this position via α(1-3) or α(1-4) fucosylation of the GlcNAc residue led to weak labeling, as in the case of the Lewis B (61) and Lewis Y (72, 73) antigens, or no appreciable labeling (e.g., 71, and 363; FIGS. 9 and 11, SI). Interestingly, we also observed weak labeling of Galβ(1-4)GlcNAc structures on the glycan array (FIG. 10, SI). However, these structures also exhibited high background signal even in the absence of UDP-GalNAz, and BgtA failed to label p-nitrophenyl 2-acetamido-2-deoxy-4-O-(β-D-galactopyranosyl)-β-D-glucopyranoside (Galβ(1-4)GlcNAc-pNP) in solution (2 h, 25° C.), suggesting that Galβ(1-4)GlcNAc structures are not covalently labeled by BgtA. Together, these studies demonstrate the strong specificity of BgtA for Fucα(1-2)Gal structures and the power of glycan microarrays to rapidly profile the specificities of glycosyltransferases for the development of chemoenzymatic detection strategies.

Figure 12:
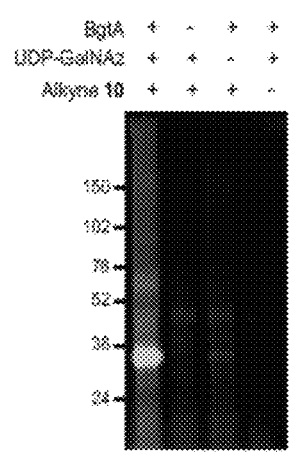
FIG. 12. In-gel fluorescence detection of Fucα(1-2)Gal glycoproteins from neuronal cell lysates. Low background fluorescence was observed in the absence of BgtA, UDP-GalNAz 2, or alkyne-TAMRA 10. The band at ~35 kDa is BgtA, which appears to label itself.
Figure 13:
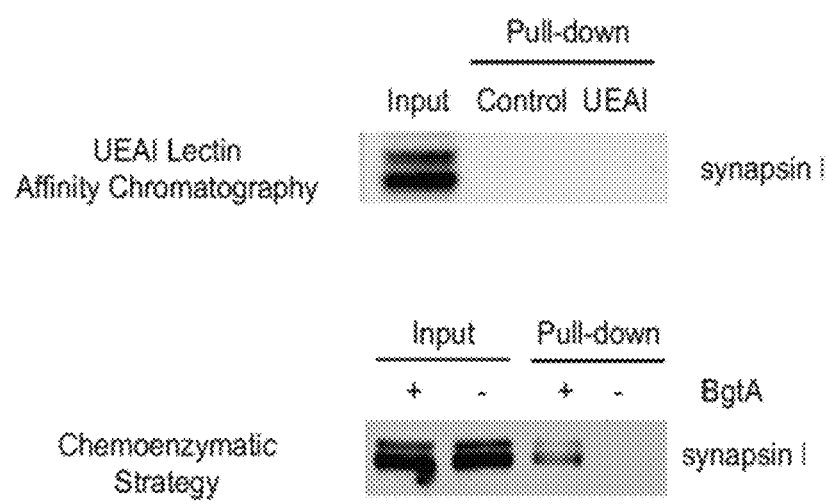
FIG. 13. Comparison of UEAI lectin affinity chromatography to the chemoenzymatic strategy. Glycosylated synapsin I from olfactory bulb lysate (500 µg) was subjected to lectin affinity chromatography or chemoenzymatic labeling followed by streptavidin capture. Western blotting for synapsin I indicated that UEAI failed to capture and detect glycosylated synapsin I, whereas the chemoenzymatic strategy allowed for ready detection.

To determine whether the approach could be used to track Fucα(1-2)Gal glycoproteins in complex cell lysates, we labeled proteins from rat brain extracts with BgtA and UDP-GalNAz, followed by Cu(I)-catalyzed reaction with the alkyne-functionalized tetramethyl-6-carboxy-rhodamine dye 10 (alkyne-TAMRA; FIG. 6, SI). We observed strong fluorescence labeling of Fucα(1-2)Gal glycoproteins, with minimal non-specific labeling in the absence of BgtA, UDP-GalNAz, or alkyne-TAMRA (FIG. 12, SI). To confirm further the specificity of the reaction, we labeled the lysates with the alkyne-biotin derivative 11 (FIG. 6, SI), captured the biotinylated proteins using streptavidin resin, and immunoblotted for the presence of known Fucα(1-2)Gal glycoproteins. ((a) Murrey, H. E.; Gama, C. I.; Kalovidouris, S. A.; Luo, W.-I.; Driggers, E. M.; Porton, B.; Hsieh-Wilson, L. C. *Proc. Natl. Acad. Sci. USA* 2006, 103, 21. (b) Murrey, H. E.; Ficarro, S. B.; Krishnamurthy, C.; Domino, S. E.; Peters, E. C.; Hsieh-Wilson, L. C. *Biochemistry* 2009, 48, 7261.) Neural cell adhesion molecule (NCAM), synapsin I, and munc18-1 were all chemoenzymatically labeled and detected in the presence, but not in the absence, of BgtA (FIG. 2B). In contrast, p44 mitogen-associated protein kinase (p44 MAPK), a protein that has not been shown to be fucosylated, was not detected. Glycosylated synapsin I was also readily observed following overexpression of Flag-tagged synapsin I in HeLa cells, chemoenzymatic labeling of the lysates with alkyne-TAMRA, synapsin immunoprecipitation, and visualization using an anti-TAMRA antibody (FIG. 2C). Importantly, UEAI lectin affinity chromatography failed to pull-down and detect glycosylated synapsin I when performed on the same scale (FIG. 13, SI). Moreover, previous studies have reported that the Fucα(1-2)Gal-specific antibody A46-B/B10 does not immunoprecipitate glycosylated synapsin I from the same neuronal lysates. (Murrey, H. E.; Gama, C. I.; Kalovidouris, S. A.; Luo, W.-I.; Driggers, E. M.; Porton, B.; Hsieh-Wilson, L. C. *Proc. Natl. Acad. Sci. USA* 2006, 103, 21.) Thus, our chemoenzymatic approach enables the highly sensitive detection of glycoproteins and provides a variety of different enrichment strategies and readouts for the Fucα(1-2)Gal motif.

Figure 3:
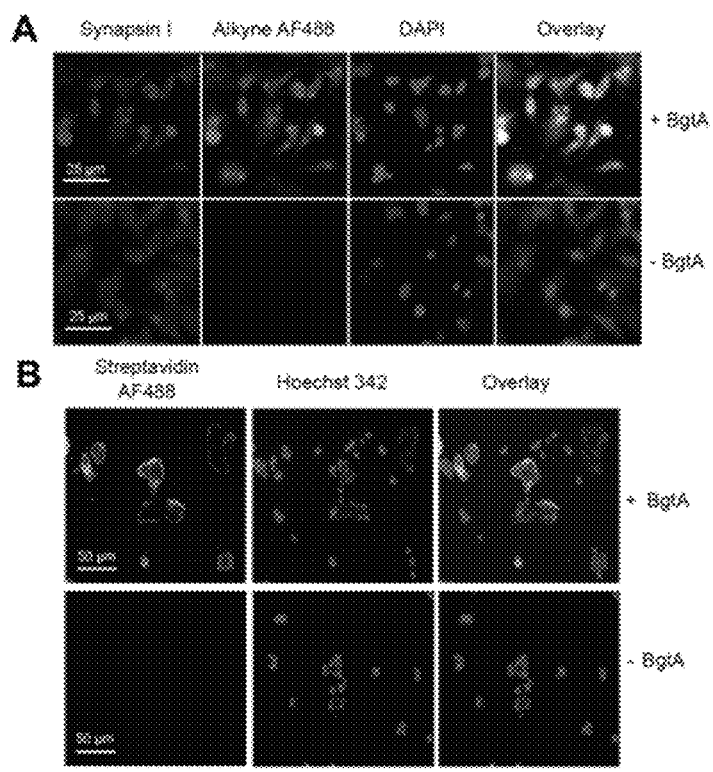
FIG. 3. (A) Fluorescence detection of Fucα(1,2)Gal glycans (green) in HeLa cells shows excellent co-localization (yellow) with Flag-tagged synapsin I (red). Nuclei were stained with 4',6-diamidino-2-phenylindole (DAPI; blue). (B) Fluorescence detection of Fucα(1,2)Gal glycans (green) on live MCF-7 cells. Nuclei were stained with Hoechst 342 (blue).
Figure 14:
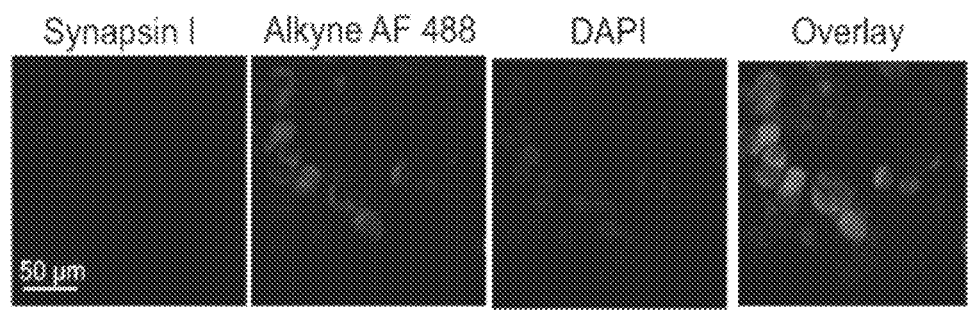
FIG. 14. Low fluorescence labeling of endogenous Fucα(1-2)Gal glycoproteins in HeLa cells. Cells were mock-transfected with an empty FLAG-vector and chemoenzymatically labeled with UDP-GalNAz and BgtA, followed by Alexa-Fluor (AF) 488 alkyne. Weak labeling of the glycoproteins (green) was observed in cells not transfected with synapsin I, suggesting low expression levels of endogenous Fucα(1-2)Gal glycoproteins. Nuclei were stained with 4',6-diamidino-2-phenylindole (DAPI; blue).

We next investigated whether the chemoenzymatic strategy could be used to image Fucα(1-2)Gal glycans in cells. HeLa cells overexpressing Flag-tagged synapsin I were fixed, permeabilized, and chemoenzymatically labeled on coverslip with BgtA and UDP-GalNAz. Cu(I)-catalyzed azide-alkyne cycloaddition (CuAAC) chemistry was then performed using an alkyne-functionalized Alexa Fluor 488 dye (12; FIG. 6, SI) to install a fluorescent reporter onto the Fucα(1-2)Gal glycans. Strong fluorescence labeling was observed in cells transfected with synapsin I, and the labeling showed excellent co-localization with intracellular synapsin I expression (FIG. 3A). No labeling of cells was observed in the absence of BgtA, and only weak labeling of endogenous Fucα(1-2)Gal glycoproteins was seen in the absence of synapsin I overexpression (FIG. 3A and FIG. 14, SI), confirming the specificity of the in situ chemoenzymatic reaction.

As the Fucα(1-2)Gal epitope has been reported to be a useful biomarker for cancer progression and prognosis, ((e) Miyake, M.; Taki, T.; Hitomi, S.; Hakomori, S.-i. *N. Engl. J. Med.* 1992, 327, 14. (f) Colnaghi, M. I.; Da Dalt, M. G.; Agresti, R.; Cattoretti, G.; Andreola, S.; Di Fronzo, G.; Del Vecchio, M.; Verderio, L.; Cascinelli, N.; Rilke, F. In Immunological Approaches to the Diagnosis and Therapy of Breast Cancer; Ceriani, R. L., Ed.; Plenum Publishing: New York, 1987, 21.) the ability to detect Fucα(1-2)Gal glycan levels on the surface of cancer cells would facilitate investigations into Fucα(1-2)Gal as a diagnostic or prognostic marker and a therapeutic target for cancer vaccines. However, antibodies and lectins that bind Fucα(1-2)Gal have been shown to cross-react with other sugar epitopes ((a) Manimala, J. C.; Roach, T. A.; Li, Z.; Gildersleeve, J. C. *Angew. Chem. Int. Ed.* 2006, 45, 3607. (b) Manimala, J. C.; Roach, T. A.; Li, Z.; Gildersleeve, J. C. *Glycobiology* 2007, 17, 17C.) such as β-linked Fuc (Manimala, J. C.; Roach, T. A.; Li, Z.; Gildersleeve, J. C. *Angew. Chem. Int. Ed.* 2006, 45, 3607.) or recognize an incomplete subset of Fucα(1-2)Gal glycans (Chang, C.-F.; Pan, J.-F.; Lin, C.-N.; Wu, I.-L.; Wong, C.-H.; Lin, C.-H. *Glycobiology* 2011, 21, 895), indicating the need for more selective, yet comprehensive, high-affinity detection methods. We therefore applied our chemoenzymatic approach to the detection of Fucα(1-2)Gal glycans on live cancer cells. Cells from the human breast adenocarcinoma cell line MCF-7 were chemoenzymatically labeled with BgtA and UDP-GalNAz for 1 h at 37° C. After reaction with ADIBO-biotin (1 h, rt), Fucα(1-2)Gal glycans were detected using streptavidin conjugated to Alexa Fluor 488 dye. Membrane-associated fluorescence was observed for cells treated with both BgtA and UDP-GalNAz, whereas no labeling was detected for control cells labeled in the absence of BgtA (FIG. 3B).

Figure 4:
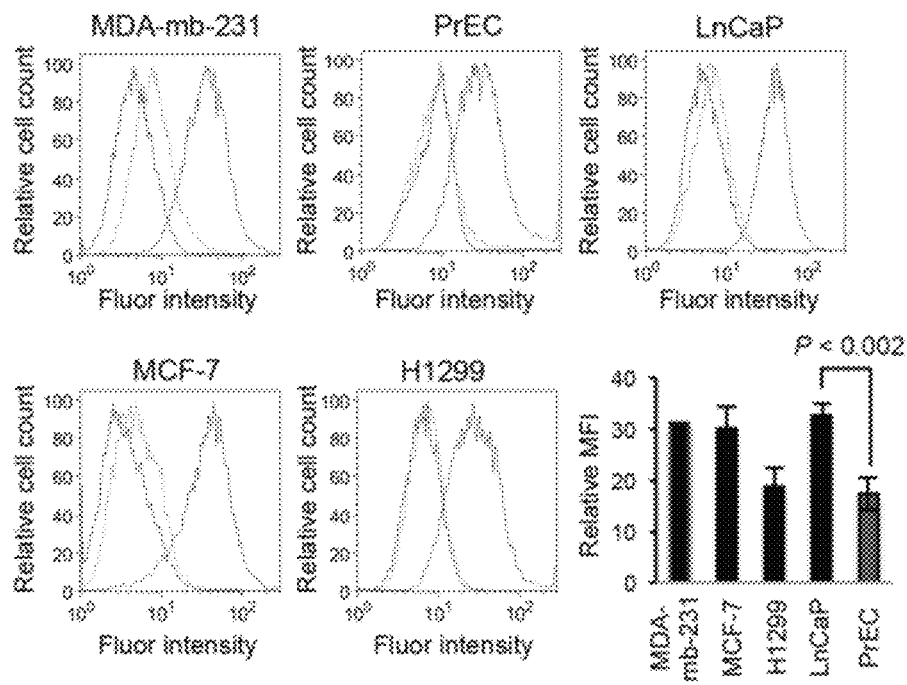
FIG. 4. Flow cytometry analysis of the relative expression levels of Fucα(1,2)Gal glycans across various cancer cell lines, with comparison to non-cancerous PrEC cells. Cells were untreated (red) or chemoenzymatically labeled in the presence (blue) or absence (green) of BgtA. Quantification of the mean fluorescence intensity (MFI) relative to cells labeled in the absence of BgtA is shown on the right. Error bars represent data from duplicate (MCF-7, MDA-mb-231, H1299) or triplicate (LnCAP, PrEC) experiments.

We next compared the expression levels of Fucα(1-2)Gal glycans across different cancer and non-cancer cell lines. MCF-7 (breast cancer), MDA-mb-231 (highly invasive breast cancer), H1299 (lung cancer), LnCAP (prostate cancer), and primary prostrate epithelial cells (PrEC) cells were chemoenzymatically labeled in suspension with BgtA and UDP-GalNAz (2 h, 37° C.), reacted with ADIBO-biotin (1 h, rt), and stained with the streptavidin-Alexa Fluor 488 conjugate (20 min, 4° C.). As shown by flow cytometry analysis, LnCaP, MCF-7, and MDA-mb-231 cells displayed the highest levels of fluorescence (FIG. 4), consistent with reports of high Globo H expression on mammary and prostate tumors. ((b) Chang, W.-W.; Lee, C. H.; Lee, P.; Lin, J.; Hsu, C.-W.; Hung, J.-T.; Lin, J.-J.; Yu, J.-C.; Shao, L.-e.; Yu, J.; Wong, C.-H.; Yu, A. L. *Proc. Natl Acad. Sci. USA* 2008, 105, 11667. (c) Menard, S.; Tagliabue, E.; Canevari, S.; Fossati, G.; Colnaghi, M. I. *Cancer Res.* 1983, 43, 1295. (d) Zhang, S.; Zhang, H. S.; Cordon-Cardo, C.; Ragupathi, G.; Livingston, P. O. *Clin. Cancer Res.* 1998, 4, 2669.) H1299 cells, a model for non-small cell lung carcinoma and also reported to express Globo H, (Lee J. S., R. J. Y., Sahin A. A., Hong, W. K., Brown, B. W., Mountain, C. F., Hittleman, W. N. *N. Engl. J. Med.* 1991, 324, 1084.) showed lower Fucα(1-2)Gal expression. Importantly, flow cytometry analysis revealed a 53% increase in Fucα(1-2)Gal expression on the surface of LnCAP cells compared to non-cancerous PrEC cells. These results demonstrate that our chemoenzymatic labeling approach can readily discriminate cancerous cells from normal cells, providing a new potential strategy for rapid biomarker detection. The method could be particularly useful for the detection of prostate cancer from tissue biopsies, as the current standard of PSA detection to diagnose prostate cancer has a significant false-positive rate, leading to overtreatment. (Schröder, F. H. et al. *N. Engl. J. Med.* 2009, 360, 1320.) In addition to histological detection, our chemoenzymatic approach could potentially provide a new strategy to distinguish normal PSA from tumorigenic PSA, which is reported to have higher levels of Fucα(1-2)Gal glycosylation. (Peracaula, R.; Tabares, G.; Royle, L.; Harvey, D. J.; Dwek, R. A.; Rudd, P. M.; de Llorens, R. *Glycobiology* 2003, 13, 457.)

In conclusion, we have developed a new chemoenzymatic strategy that detects Fucα(1-2)Gal glycans with improved efficiency and selectivity over existing methods. Our strategy detects a variety of complex Fucα(1-2)Gal glycans and glycoproteins and permits living cells or complex tissue extracts to be rapidly interrogated. We anticipate that the strategy will accelerate both the discovery of new Fucα(1-2)Gal glycoproteins and advance an understanding of the biological roles of this important sugar in neurobiology and cancer. Moreover, this study represents a proof-of-concept that chemoenzymatic labeling strategies can be extended to more complex oligosaccharides. Future studies will expand chemoenzymatic detection approaches to a broad range of glycans to provide a powerful new set of tools for glycomics research.

General Methods for Chemical Synthesis.

Unless otherwise stated, all starting materials and reagents were purchased from Sigma-Aldrich and used without further purification. All $^1$H and $^{13}$C NMR spectra were recorded on a Varian Innova 600 spectrometer and referenced to solvent peaks. Data for $^1$H NMR spectra are reported as follows: chemical shift (δ ppm), multiplicity (s=singlet, d=doublet, t=triplet, q=quartet, m=multiplet), coupling constant in Hz, and integration. Low-resolution mass spectra were recorded on an 1100 Agilent Liquid Chromatograph Mass Spectrometer with an Agilent SB-C18 reverse-phase column (3.5 μm, 4.6×250 mm) with monitoring at 280 and 310 nm. High-resolution mass spectra (HRMS) were obtained using an Agilent 6200 Series Time of Flight Mass Spectrometer with an Agilent G1978A Multimode source using mixed electrospray ionization/atmospheric pressure chemical ionization (MultiMode ESI/APCI).

Synthesis of 1-p-Nitrobenzyl-(2-fucosyl)-lactose (1)

A 0.35 M solution of p-nitrobenzylamine in 7:3 (v/v) DMSO/AcOH (50 μL 18 μmol) was added slowly to 2'-fucosyllactose (1.0 mg, 2.0 μmol) at rt. NaCNBH$_3$ (50 μL of a 1 M solution in 7:3 (v/v) DMSO/AcOH, 50 μmol) was then added slowly at rt, and the solution was stirred at 65° C. for 4 h. The reaction was quenched by adding 10 volumes of MeCN and incubated at −20° C. for 2 h. The precipitated mixture was then centrifuged at 10,000×g for 5 min at 4° C., and the supernatant was discarded. Ten additional volumes of MeCN were added to the pellet, and the vortexed mixture was incubated at −20° C. for 2 h and centrifuged as above. This step was repeated two more times to remove the excess p-nitrobenzylamine. The pellet was then resuspended in 5% MeCN and the product purified by semi-preparative HPLC (Agilent 1100) using two preparative reverse-phase columns (Agilent Eclipse XDB-C18; 5 μm, 9.4×250 mm) connected in series and a gradient of 5-20% B over 20 min at 4 mL/min (A, 0.5% aqueous AcOH; B, 100% MeCN). The product eluted at approximately 9.5 min. Lyophilization afforded a fluffy white solid (0.72 mg; 56% yield): $^1$H NMR (600 MHz, D$_2$O) δ 8.33 (d, J=8.6 Hz, 2H), 7.72 (d, J=8.7 Hz, 2H), 5.31 (s, 1H), 4.60 (d, J=7.8 Hz, 1H), 4.33 (q, J=13.7 Hz, 2H), 4.23 (t, J=6.3 Hz, 2H), 3.93 (d, J=3.4 Hz, 1H), 3.91-3.86 (m, 4H), 3.83 (t, J=4.4 Hz, 4H), 3.79-3.71 (m, 4H), 3.67 (dd, J=9.5, 7.9 Hz, 1H), 3.32 (d, J=11.7 Hz, 1H), 3.10 (t, J=11.1 Hz, 1H), 1.23 (d, J=6.6 Hz, 3H). $^{13}$C NMR (151 MHz, D$_2$O) δ 147.86, 130.43, 124.09, 109.99, 107.14, 100.42, 99.65, 76.94, 76.65, 75.19, 73.42, 71.69, 70.48, 70.19, 69.45, 68.97, 68.51, 68.21, 67.18, 61.93, 60.90, 50.51, 49.52, 23.19, 15.29. HRMS: [M+H]$^+$ calculated for C$_{25}$H$_{40}$N$_2$O$_{16}$ 625.5996. Found 625.2451.

Expression and Purification of BgtA.

*E. coli* BL21 (DE3) harboring the recombinant plasmid vector pET28a-BtgA-His was kindly provided by Dr. Peng George Wang (Ohio State University). The protein was expressed and purified as described. (Yi, W.; Shen, J.; Zhou, G.; Li, J.; Wang, P. G. *J. Am. Chem. Soc.* 2008, 130, 14420.) Briefly, the cells were grown in LB medium (1 L) at 37° C. Isopropyl-1-thio-β-D-galactospyranoside (IPTG, 0.8 mM final concentration; Sigma) was added when the cells reached an OD$_{600}$ of 0.8, and the cells were incubated for an additional 18 h at 16° C. The pelleted cells were lysed in Cell Lytic B Lysis Reagent (Sigma-Aldrich) supplemented with EDTA-free Complete™ protease inhibitors (Roche), 0.5 M NaCl, and 20 mM imidazole (Sigma-Aldrich) by rotating end-over-end for 20 min at rt. After centrifugation, the clarified lysate was added to prewashed Ni-NTA beads and incubated at 4° C. for 1 h, washed in 20 mM Tris.HCl pH 7.5, 0.5 M NaCl and 50 mM imidazole, and eluted in a step gradient with the elution buffer (20 mM Tris.HCl pH 7.5, 0.5 M NaCl, and 100, 200 or 500 mM imidazole). After SDS-PAGE analysis, the purified protein was concentrated with 10,000 Da molecular weight cut-off (MWCO) spin filters (Millipore) and dialyzed into 20 mM Tris.HCl pH 7.5 containing 10% glycerol and stored at 4° C.

BgtA Activity Assay and Monitoring of Chemoenzymatic Labeling Reactions by LC-MS/MS.

The Fucα(1-2)Gal substrate 1 (10 μM) was dissolved in 20 mM Tris.HCl pH 7.5, 50 mM NaCl, and 5 mM MnCl$_2$. BgtA enzyme (Yi, W.; Shen, J.; Zhou, G.; Li, J.; Wang, P. G. *J. Am. Chem. Soc.* 2008, 130, 14420.) and UDP-ketoGal 3

(Khidekel, N.; Arndt, S.; Lamarre-Vincent, N.; Lippert, A.; Poulin-Kerstien, K. G.; Ramakrishnan, B.; Qasba, P. K.; Hsieh-Wilson, L. C. *J. Am. Chem. Soc.* 2003, 125, 16162.) or UDP-GalNAz 2 (Invitrogen) were added to final concentrations of 0.16 mg/mL and 50 μM, respectively, in a final volume of 100 μL. The reaction was incubated at 4° C. in the dark for 12-16 h, and the reaction progress was monitored by LC-MS/MS. To label with aminooxy-biotin 7, the reactions were diluted 5-fold with saturated urea, 2.7 M NaOAc pH 3.9 (50 mM final concentration and pH 4.8), and 7 (5 mM final concentration, Dojindo) and incubated for 20-24 h at rt. To label with ADIBO-biotin 6, 250 μM of 6 (Click Chemistry Tools) was added, and the reaction was incubated for 3 h at rt. Following the labeling steps, the azido-labeled samples were filtered through a 3,000 Da MWCO Vivaspin 500 spin filter (GE Lifesciences) and injected on a reverse-phase HPLC column (Phenomenex Gemini; 5 m, 2.0×100 mm), fitted with a C8 guard column, using a ThermoScientific Accela 600 HPLC pump interfaced with a ThermoScientific LTQ mass spectrometer. A linear 3-90% gradient of B (A: 0.1% aqueous formic acid, B: 0.1% formic acid in MeCN) over 7 min was used to resolve peaks with a flow rate of 0.21 mL/min. Mass analysis was performed in positive ion mode except in the case of sulfated compound 8, where the analysis was performed in negative ion mode.

Kinetic Analysis of BgtA with UDP-GalNAz and UDP-GalNAc.

Reactions were performed in duplicate with 100 μM acceptor substrate (1), 0.7 μg BgtA, and varying concentrations of UDP-GalNAz or UDP-GalNAc (50 to 800 μM) in 20 mM Tris-HCl pH 7.5, 50 mM NaCl, 10 mM $MnCl_2$ at rt in a total volume of 20 μL. Product formation was monitored at 280 nm by reverse phase-HPLC (Agilent 1100), and time points were taken over the course of 5 min using a linear, 3-95% gradient of B (A: 0.1% aqueous trifluoroacetic acid B: 0.1% trifluoroacetic acid in MeCN) over 8 min with a flow rate of 1 mL/min. The kinetic parameters, apparent $K_m$, $V_{max}$, and $k_{cat}$, were obtained by linear regression analysis of initial velocity vs. donor substrate concentration using KaleidaGraph (version 4.1.2).

Chemoenzymatic Labeling on the Glycan Array.

Glycan Array version 5.0 was provided by the Consortium for Functional Glycomics (CFG). Pre-equilibrated arrays were treated with BgtA enzyme (0.16 mg/mL) and 500 μM UDP-GalNAz 2 in 20 mM Tris.HCl pH 7.4, 50 mM NaCl, 2 mM $MnCl_2$ containing 1% bovine serum albumin (BSA) for various times (0, 0.5, 2, and 12 h) at rt, washed 4 times with wash buffer (20 mM Tris.HCl pH 7.4, 50 mM NaCl, 0.1% Triton X-100) and then 4 times with rinse buffer (20 mM Tris.HCl pH 7.4, 50 mM NaCl). The arrays were then incubated with ADIBO-biotin (5 μM) in 20 mM Tris.HCl pH 7.4, 50 mM NaCl for 2 h at rt. After washing as described above, the arrays were washed further with 20% aqueous MeOH and then incubated with streptavidin Cy-5 (0.5 μg/mL; eBioSciences) in 20 mM Tris.HCl pH 7.4, 50 mM NaCl, 0.05% Tween-20, 1% BSA, for 1 h at rt. The arrays were then washed 4 times with wash buffer (containing 0.05% Tween-20 instead of 0.1% Triton X-100), 4 times with rinse buffer, 4 times with water, dried under a low stream of filtered air, and scanned using a PerkinElmer ScanArray Express fluorescence scanner and ImaGene data analysis software (BioDiscovery). Data were analyzed per the guidelines of the CFG. ((a) Blixt, O.; Head, S.; Mondala, T.; Scanlan, C.; Huflejt, M. E.; Alvarez, R.; Bryan, M. C.; Fazio, F.; Calarese, D.; Stevens, J.; Razi, N.; Stevens, D. J.; Skehel, J. J.; van Die, I.; Burton, D. R.; Wilson, I. A.; Cummings, R.; Bovin, N.; Wong, C.-H.; Paulson, J. C. *Proc. Natl Acad. Sci. USA* 2004, 101, 17033. (b) Smith, D. S.; Song, X.; Cummings, R. D. *Methods in Enzymology* 2010, 480, 417.) The background fluorescence for each spot was determined as the fluorescence signal outside of the area designated as a positive spot on the array. Because background fluorescence can be heterogeneous across the array, each array was divided into areas of 10 by 10 spots, or sub-arrays, and a background fluorescence value was calculated within each sub-array by the software. This value was then subtracted from the fluorescence signal for each glycan spot within the sub-array by the software. Note that each glycan is printed six different times on the array. To calculate the relative fluorescence intensity for a given glycan, the highest and lowest intensities for each glycan were discarded, and the mean and standard deviation of four fluorescence intensities were calculated.

Chemoenzymatic Labeling of Cell Lysates.

The olfactory bulbs of postnatal day 3 rat pups were dissected on ice and lysed in boiling 1% SDS (5 volumes/weight) with sonication until the mixture was homogeneous. Protein was precipitated using methanol/chloroform/water. Briefly, protein was diluted to 200 μL and precipitated by sequential mixing with 600 μL of MeOH, 200 μL of $CHCl_3$ and 450 μL $H_2O$, after which the mixture was centrifuged at 23,000×g for 15 min. Precipitated protein was washed with 450 μL of MeOH and centrifuged at 23,000×g for 10 min. After the protein pellet was allowed to dry briefly, the pellet was re-dissolved at 5 mg/mL in 20 mM HEPES pH 7.9 containing 1% SDS, and diluted 5-fold into a buffer with the following final concentrations: 20 mM HEPES pH 7.9, 50 mM NaCl, 2% NP-40, 5 mM $MnCl_2$. UDP-GalNAz 2 (25 μM; Invitrogen) and BgtA (0.16 mg/mL) were added, and the samples were incubated at 4° C. for 16-20 h. The labeled proteins were precipitated as above and resuspended in 50 mM Tris pH 7.4 containing 1% SDS at 4 mg/mL.

The resuspended proteins were subsequently reacted with alkyne-TAMRA 10 (Invitrogen) or alkyne-biotin 11 (Invitrogen) as per the Click-It™ TAMRA and Biotin Glycoprotein Detection Kit (Invitrogen) instructions, except that EDTA-free Complete™ protease inhibitors were added during the reaction. For TAMRA labeling, negative controls were performed under identical conditions except that BgtA, UDP-GalNAz 2, or alkyne-TAMRA 10 was omitted from the labeling reaction. After the labeling reactions, protein was precipitated using chloroform/methanol/water as described above and re-dissolved in boiling 2% SDS. This precipitation and resolubilization was then repeated once more to ensure removal of non-specific interactions. TAMRA-labeled proteins were resolved by SDS-PAGE and visualized in-gel using a Typhoon Scanner (GE Healthcare). Interestingly, BgtA itself was labeled, and attempts to remove the signal by precipitation or heat and detergent denaturation were unsuccessful, suggesting covalent modification of the protein. For biotin labeling, negative controls were performed under identical conditions except that BgtA was omitted from the labeling reaction.

Purification of Biotin-Labeled Fucα(1-2)Gal Proteins.

Chemoenzymatically labeled samples were precipitated using methanol/chloroform/water as described above and re-dissolved in boiling 1% SDS plus Complete™ protease inhibitors at a concentration of 2 mg/mL. The SDS was quenched with 1 volume of NETFD buffer (100 mM NaCl, 50 mM Tris.HCl pH 7.4, 5 mM EDTA, 6% NP-40) plus protease inhibitors. The samples were incubated with pre-washed streptavidin resin (Pierce; 100 μL/1 mg protein) for 2 h at 4° C. The resin was washed twice with 10 column volumes each of low salt buffer (0.1 M $Na_2HPO_4$ pH 7.5, 0.15 M NaCl, 1% Triton-X100, 0.1% SDS), twice with 10 column volumes each of high salt buffer (0.1 M $Na_2HPO_4$ pH 7.5, 0.5 M NaCl, 0.2% Triton-X100), and once with 10 column volumes of 50 mM Tris.HCl pH 7.4. Captured protein was eluted in boiling 2× sample buffer (100 mM Tris pH 6.8, 4% SDS, 200 mM DTT, 20% glycerol, 0.1% bromophenol blue; 50 µL/100 µL resin) for 5 min.

Western Blotting for Parallel Identification of Fucα(1-2) Gal Glycoproteins.

The purified, labeled material from above was resolved on a NuPAGE 4-12% Bis-Tris gel (Invitrogen) and transferred to a polyvinylidene difluoride (PVDF) membrane (Millipore). The membrane was blocked in 5% milk (BioRad) in TBST (50 mM Tris.HCl, 150 mM NaCl, 0.05% Tween 20, pH 7.4) for 1 h at rt. Primary antibodies in 5% milk in TBST were added overnight at 4° C. at the following concentrations: mouse anti-NCAM monoclonal antibody (Abcam) at 1 µg/mL, mouse anti-synapsin I ascites (Synaptic Systems) at 0.1 µg/ml, mouse anti-munc18-1 (Synaptic Systems) at 0.1 µg/mL, or mouse p44 MAPK monoclonal antibody (Cell Signaling) at 1:2000 dilution. Membranes were washed with TBST, and incubated with the appropriate Alexa Fluor 680-conjugated (Invitrogen) or IR800-conjugated (Rockland) secondary antibody, and visualized using a LiCOR Odyssey Imaging System.

Lectin Affinity Chromatography with UEAI.

UEAI lectin conjugated to agarose (Vector Laboratories) or control protein A conjugated to agarose (Vector Laboratories) was packed into a minicolumn (50 µL bed volume; Bio-Rad), and the columns were run in parallel. The resin was equilibrated with 10 column volumes of lectin binding buffer (100 mM Tris pH 7.5, 150 mM NaCl, 1 mM $CaCl_2$, 1 mM $MgCl_2$, 0.5% NP-40, and 0.2% sodium deoxycholate supplemented with EDTA-free Complete™ protease inhibitors). Olfactory bulb tissue from P3 rat pups was lysed in lectin binding buffer by sonication on ice. The lysate was clarified by centrifugation at 12000×g for 10 min, and the total protein concentration was determined using the BCA protein assay (Pierce). Lysate (500 µg) was bound batchwise with gentle end-over-end mixing at rt for 4 h. The agarose was then allowed to settle, and the flow-through was passed over the column three additional times. The columns were washed with 40 column volumes of lectin binding buffer, followed by 10 column volumes of lectin binding buffer lacking detergent. Proteins were eluted in 10 column volumes of lectin binding buffer lacking detergent and supplemented with 200 mM L-fucose and Complete™ protease inhibitors. Protein eluates were concentrated to a volume of 100 µL using a Vivaspin 500 spin filter (10,000 Da MWCO). Following concentration, samples were boiled in 1× sample buffer (35 µL of 200 mM Tris pH 6.8, 400 mM DTT, 8% SDS, 0.2% bromophenol blue, and 40% glycerol) and analyzed by SDS-PAGE and western blotting as described above. Synapsin I was detected using mouse anti-synapsin I ascites (Synaptic Systems) at 0.1 µg/mL.

Cell Culture.

HeLa, MCF-7, and MDA-mb-231 cells grown in DMEM medium supplemented with 10% fetal bovine serum (FBS), 100 units/mL penicillin, and 0.1 mg/mL streptomycin (Gibco). LNCaP and H1299 cells were grown in RPMI medium 1640 supplemented with 10% FBS, 100 units/mL penicillin, and 0.1 mg/mL streptomycin (Gibco). The PrEC line was maintained in PrEBM medium (Lonza). All transfections were carried out in antibiotic-free media. In all cases, cells were incubated in a 5% $CO_2$ humidified chamber at 37° C. The PrEC line was obtained from Lonza; all other cell lines were obtained from ATCC.

Immunoprecipitation of TAMRA-Labeled Synapsin I from HeLa Cell Lysates.

HeLa cells were transfected with pCMV-FLAG-synapsin Ia (Murrey, H. E.; Gama, C. I.; Kalovidouris, S. A.; Luo, W.-I.; Driggers, E. M.; Porton, B.; Hsieh-Wilson, L. C. Proc. Natl Acad. Sci. USA 2006, 103, 21.) using Lipofectamine LTX reagent (Invitrogen). The cells were lysed and chemoenzymatically labeled and protein was precipitated as described above. After the protein pellet was allowed to dry briefly, the pellet was re-dissolved in boiling 1% SDS plus Complete™ protease inhibitors at a concentration of 2 mg/mL. The SDS was quenched with 1 volume of NETFD buffer plus protease inhibitors, and the lysate was incubated with 40 µL of prewashed anti-Flag M2 Affinity Gel (Sigma-Aldrich) for 90 min at 4° C. The resin was washed once with 4 column volumes of NETFD buffer and three times with 4 column volumes of NETF buffer (100 mM NaCl, 50 mM Tris.HCl pH 7.4, 5 mM EDTA). Captured protein was eluted in boiling 2× sample buffer (50 µL buffer/100 µL resin). Purified, labeled material was resolved by SDS-PAGE and transferred to a polyvinylidene fluoride (PVDF) membrane (Millipore). Western blotting was performed as above except the primary anti-TAMRA rabbit antibody (0.1 µg/µL; Invitrogen) was used.

Detection of Cell-Surface Fucα(1-2)Gal Glycans on Live MCF-7 Cells by Fluorescence Microscopy.

MCF-7 cells (ATCC) were seeded at $2\times10^5$ cells/coverslip. Twelve hours after plating, the cells were washed twice with 1% FBS, 10 mM HEPES in calcium and magnesium free Hank's Balanced Salt Solution (CMF HBSS, Gibco) and incubated in the chemoenzymatic labeling buffer (2% FBS, 10 mM HEPES pH 7.9 in HBSS) with UDP-GalNAz 2 (500 µM) and BgtA (0.17 mg/mL) in a total volume of 100 µL for 2 h at 37° C. Mock reactions were performed without the addition of BgtA. After chemoenzymatic labeling, the cells were washed twice with 100% FBS and twice with the chemoenzymatic labeling buffer. Enzymatic addition of GalNAz onto Fucα(1-2)Gal glycans was detected by incubating the cells with ADIBO-biotin (20 µM in the chemoenzymatic labeling buffer; 500 µL) for 1 h at rt, washing the coverslips as described, and then incubation with streptavidin-Alexa Fluor 488 (1 µg/mL in PBS containing 3% BSA; Invitrogen) for 30 min at rt. Cells were washed once with PBS, after which nuclei were stained with Hoechst-33342 (1 µg/µL; Invitrogen) in PBS for 15 min at rt. Coverslips were washed twice with 100% FBS and mounted in media (on ice), sealed with paraffin, and imaged immediately using a 40× Plan-Achromat objective on a Zeiss Meta510 inverted microscope.

Detection of Fucα(1-2)-Gal Glycans on Synapsin I in Fixed HeLa Cells by Fluorescence Microscopy.

HeLa cells were plated onto 15 mm coverslips (Carolina Biologicals) at a density of 75 cells/mm². After 12 h, cells were transfected with pCMV-Flag-synapsin Ia (0.5 µg DNA/coverslip) using Lipofectamine LTX (4 µL in 200 µL Optimem; Invitrogen). After 24 h, the media was removed, and the cells were rinsed one time with PBS, fixed in 4% paraformaldehyde in PBS, pH 7.5 for 20 min at rt, washed twice with PBS, permeabilized in 0.3% Triton X-100 in PBS for 10 min at rt, and washed twice with the enzymatic labeling buffer (50 mM HEPES, 125 mM NaCl, pH 7.9). Reaction mixtures and negative controls (without BgtA) were prepared by adding 100 µL of 20 mM HEPES pH 7.9, 50 mM NaCl, 2% NP-40, 5 mM $MnCl_2$, UDP-GalNAz 1 (25 µM), and BgtA (0.17 mg/mL) at 4° C. for 24 h (100 µL/coverslip) in a humidified chamber. After chemoenzymatic labeling, the cells were washed twice with the chemoenzymatic labeling buffer. Enzymatic addition of Gal-NAz onto Fucα(1-2)Gal glycans was detected by treating the cells with 5 μM alkyne-functionalized Alexa Fluor 488 (Invitrogen), 0.1 mM triazoleamine ligand (Invitrogen), 2 mM sodium ascorbate (Sigma-Aldrich), and 1 mM $CuSO_4$ (Sigma-Aldrich) in 2% FBS (Gibco) in PBS at rt for 1 h. Synapsin I was detected by immunostaining with an anti-synapsin I antibody (Millipore, 1:250 in 3% BSA) for 1 h at rt, followed by an anti-rabbit secondary antibody conjugated to Alexa Fluor 546 (Invitrogen; 1:1000 in 3% BSA) for 1 h at rt. The coverslips were washed with PBS, mounted onto glass slides using Vectashield mounting medium with DAPI (4 μL; Vector Labs) and sealed with clear nail polish. Cells were imaged using a Nikon Eclipse TE2000-S inverted microscope, and images were captured with Metamorph software using a 20× Plan Fluor objective.

Detection of Cell-Surface Fucα(1-2)Gal Glycans on Live Cancer Cells by Flow Cytometry.

All cells were seeded at $4 \times 10^6$ cells per 10-cm plate in 10 mL of the appropriate media. On the day of analysis, cells were lifted off the plate with DNase (0.4 mg/mL; Worthington) and 1 mM EDTA and washed with 1% FBS, 10 mM HEPES in CMF HBSS. One million cells were chemoenzymatically labeled with UDP-GalNAz (500 μM) and BgtA (0.17 μg/μL) in 1% FBS, 10 mM HEPES in CMF HBSS (100 μL) for 2 h at 37° C. Cells were spun twice through 100% FBS (1 mL) to remove excess reagent (500×g, 5 min) and resuspended in 1% FBS, 10 mM HEPES in CMF HBSS (100 μL) containing ADIBO-biotin (20 μM) and incubated for 1 h at rt. Cells were again spun twice through 100% FBS (1 mL), and washed with 3% BSA in PBS (1 mL). Cells were then resuspended in 3% BSA in PBS (100 μL) containing streptavidin-Alexa Fluor 488 (1 μg/mL) and incubated for 20 min at 4° C. Cells were subsequently spun twice through 100% FBS (1 mL) and resuspended in 2% FBS, 10 mM HEPES in CMF HBSS (750 μL) for flow cytometry analysis. Immediately before analysis, 7-amino-actinomycin D (7-AAD, 5 μL; eBioscience) was added to measure cell viability. Cells were analyzed for FITC intensity on a Beckman Dickenson FACSCalibur flow cytometer equipped with a 488-nm argon laser. For each experiment, 10,000 live cells were analyzed, and data analysis was performed on FlowJo (Tristar Inc.). Data points for LnCAP and PrEC cells were collected in triplicate, and for all other cells, in duplicate.

We have developed a chemoenzymatic approach for the detection of glyco-conjugates containing the fucose-α(1-2)-galactose (Fucα(1,2)Gal) motif. Using the bacterial homologue to the blood group transferase A (BgtA), we can specifically install azido- or ketone-containing sugars (e.g., GalNAz, or 2-deoxy-keto-Gal) onto the disaccharide moiety. Following the use of "click chemistry" (Cu(I)-catalyzed or strain-promoted [3+2] cycloaddition chemistry) or oxime chemistry with detection reagents (affinity, fluorescent, mass tag, isotope tag, etc.) we can detect this glycan structure using various readouts (e.g., Western Blotting, in gel fluorescence, flow cytometry, mass spectrometry, and fluorescence microscopy).

We envision many other applications of our method. First, this method is amenable to proteomics. Following the labeling of Fucα(1,2)Gal the with affinity reagents such as biotin or TAMRA, proteins may be purified, digested with a protease, and the Fucα(1,2)Gal proteins identified by mass spectrometry. Alternatively, labeled proteins can be digested with proteases and the glycopeptides enriched by affinity chromatography (e.g., avidin agarose or using an anti-TAMRA antibody) and subjected to mass spectrometry to identify the corresponding Fucα(1,2)Gal proteins. Following this experimental workflow this method can also be used for identifying the site of glycosylation on the protein, that is, what amino acid side chain is modified with this glycan, as well as the entire Fucα(1,2)Gal-containing glycan. These proteomic studies would be interested for identifying glycoproteins from serum or tumors that have increasing amounts of Fucα(1,2)Gal epitope in various cancers, stages of cancer, or other disease states.

This method can also be used to identify changes in the levels of Fucα(1,2)Gal glycoconjugates on tissues or cells after various stimulations, such as neuronal activity or learning, cancer treatments (a method to identify efficacy of cancer treatment in patients), and pharmacological treatments (studying what signaling pathways in cells lead to differential expression of these glycans on the cell surface). This can be done using methods known in the field such as quantitative proteomics, Western blotting and/or in gel fluorescence.

Our method can also allow quantification of the stoichiometry of Fucα(1,2)Gal on specific proteins following the outline described in Rexach et al. (*Nature Chemical Biology* 2010, 9, 645-651). This method employs installing a polyethyleneglycol polymer mass tag instead of an affinity or fluorescent tag, immunoblotting for protein(s) of interest, and quantifying the relative intensities of the mass shifted bands to quantify the stoichiometry of glycosylation.

This labeling technology may also be applied as a diagnostic tool to detect the presence of Fucα(1,2)Gal on potential biomarkers. For example, fluorescently labeled Fucα(1,2)Gal proteins from cell lysates or serum could be captured (e.g., using antibodies against the protein of interest, such as against prostate specific antigen, PSA, for prostate cancer) on the bottom of a 96-well plate or other format, and the levels of Fucα(1,2)Gal on the protein of interest could be detected by fluorescence.

In summary the potential applications of this labeling method are as such:

1) Proteomics/Lipidomics—identification of glycoproteins/biomarkers bearing Fucα(1,2)Gal.

2) Site mapping—identification of amino acids modified by fucα(1,2)gal.

3) Monitoring changes in Fucα(1,2)Gal levels following various stimulations or normal versus disease states.

4) Characterizing the stoichiometry of the Fucα(1,2)Gal modification on specific proteins.

5) Use of this method as a diagnostic tool for detecting biomarkers in an ELISA assay-type format. Alterations in Fucα(1,2)Gal glycan expression could occur in the case of various cancers, learning, aging, neurodegenerative diseases and other diseases.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING
*Helicobacter mustelae* homologue of Human blood Group A transferase (BgtA)
SEQ ID NO: 1
MQSTAQNTQQNTHFAGSSQTTPQAAQSVQQASLALPKSSPTCYKIA
ILYICTGAYSIFWQDFYDSAKVHLLPAHRLTYFVFTDADSLYAEEA
SDVRKIYQENLGWPFNTLKRFEMFLGQEEALREFDFVFFFNANCLF
FQHIGDEFLPIEEDILVTQHYGFRDASPECFTYERNPKSLAYVPFG
KGKAYVYGSTNGGKAGAFLALARTLQERIQEDLSRGIIAIWHDESH
LNAYIIDHPNYKMLDYGYGFPEGYGRVPGGGVYIFLRDKSRVIDVN
AIKGMGSPANRRLKNALRKLKHFSKRLLGR

*Helicobacter mustelae* homologue of Human blood Group A transferase (BgtA)(Pet28a-BgtA-6His ("6His" disclosed as SEQ ID NO: 6))(this is the enzyme we actually use after cloning into Pet28a vector
SEQ ID NO: 2
MGQSTAQNTQQNTHFAGSSQTTPQAAQSVQQASLALPKSSPTCYKIA
ILYICTGAYSIFWQDFYDSAKVHLLPAHRLTYFVFTDADSLYAEEAS
DVRKIYQENLGWPFNTLKRFEMFLGQEEALREFDFVFFFNANCLFFQ
HIGDEFLPIEEDILVTQHYGFRDASPECFTYERNPKSLAYVPFGKGK
AYVYGSTNGGKAGAFLALARTLQERIQEDLSRGIIAIWHDESHLNAY
IIDHPNYKMLDYGYGFPEGYGRVPGGGVYIFLRDKSRVIDVNAIKGM
GSPANRRLKNALRKLKHFSKRLLGRLEHHHHHH Human blood Group A transferase
SEQ ID NO: 3
MAEVLRTLAGKPKCHALRPMILFLIMLVLVLFGYGVLSPRSLMPGSL
ERGFCMAVREPDHLQRVSLPRMVYPQPKVLTPCRKDVLVVTPWLAPI
VWEGTFNIDILNEQFRLQNTTIGLTVFAIKKYVAFLKLFLETAEKHF MVGHRVHYYVFTDQPAAVPRVTLGTGRQLSVLEVRAYKRWQDVSMRR
MEMISDFCERRFLSEVDYLVCVDVDMEFRDHVGVEILTPLFGTLHPG
FYGSSREAFTYERRPQSQAYIPKDEGDFYYLGGFFGGSVQEVQRLTR
ACHQAMMVDQANGIEAVWHDESHLNKYLLRHKPTKVLSPEYLWDQQL
LGWPAVLRKLRFTAVPKNHQAVRNP Rat blood Group A transferase
SEQ ID NO: 4
MDLRGRPKCYSLHLGILPFIVLVLVFFGYGFLSHKIQEFRNPGGET
CMATRQTDVQKVVSVPRMAYPQPNVLTPIRNDVLVFTPWLAPIIWE
GTFNIDILNEQFKLQNTTIGLTVFAIKKYVVFLKLFLETAEQHFMV
GHKVIYYVFTDRPSDVPQVPLGAGRKLVVLTVRNYTRWQDVSMHRM
EMISHFSEQRFQHEVDYLVCGDVDMKFSDHVGVEILSALFGTLHPG
FYRSRRESFTYERRPKSQAYIPRDEGDFYYAGGFFGGSVVEVHHLT
KACHQAMVEDQANGIEAVWHDESHLNKYLLYHKPTKVLSPEYVWDQ
KLLGWPSIMKKLRYVAVPKNHQAIRN Mouse blood Group A transferase
SEQ ID NO: 5
MNLRGRPKCNFLHLGILPFAVFVLVFFGYLFLSFRSQNLGHPGA
VTRNAYLQPRVLKPTRKDVLVLTPWLAPIIWEGTFNIDILNEQF
RIRNTTIGLTVFAIKKYVVFLKLFLETAEQHFMVGHKVIYYVFT
DRPADVPQVILGAGRQLVVLTVRNYTRWQDVSMHRMEMISHFSE
RRFLREVDYLVCADADMKFSDHVGVEILSTFFGTLHPGFYSSSR
EAFTYERRPQSQAYIPWDRGDFYYGGAFFGGSVLEVYHLTKACH
EAMMEDKANGIEPVWHDESYLNKYLLYHKPTKVLSPEYLWDQQL
LGWPSIMKKLRYVAVPKDHQAIRN

---

What is claimed is:

1. A glycan comprising:
   1) a first glycosyl group comprising fucose-α(1-2)-galactose; and
   2) a second glycosyl group covalently linked to the first glycosyl group, wherein the second glycosyl group is covalently linked to the first glycosyl group at the C-3 position of the galactose on the first glycosyl group, and wherein the second glycosyl group comprises a reactive group (R), wherein linking the second glycosyl group to the first glycosyl group involves reacting a labeling agent with a glycosyltransferase, wherein the labeling agent is a compound of the formula:

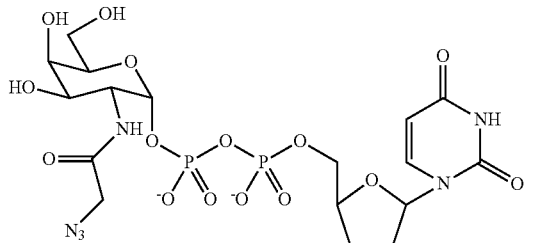

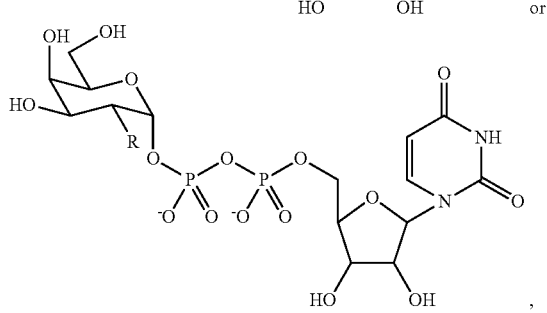

wherein R is a substituent selected from the group consisting of a straight chain or branched $C_1$-$C_{12}$ carbon chain bearing a carbonyl group, an azide group, a straight chain or branched $C_1$-$C_{12}$ carbon chain bearing an azide group, a straight chain or branched $C_1$-$C_{12}$ carbon chain bearing an alkyne, or a straight chain or branched $C_1$-$C_{12}$ carbon chain bearing an alkene.

2. The glycan of claim 1, wherein the glycan is attached to a glycoprotein or glycolipid.

3. The glycan of claim 1, further comprising a detection agent covalently linked to the second glycosyl group, wherein the detection agent is covalently linked to the second glycosyl group via a reaction between a coupling moiety on the detection agent and the reactive group, and wherein the detection agent is selected from the group consisting of a fluorescent reagent, an enzymatic reagent capable of converting substrates calorimetrically or fluorometrically, a fluorescent and luminescent probe, a metal-binding probe, a protein-binding probe, a probe for antibody-based binding, a radioactive probe, a photocaged probe, a spin-label, spectroscopic probe, a heavy-atom containing probe, poly(ethylene)glycol-containing probe and poly(propylene)glycol-containing probe.

4. The glycan of claim 1, wherein the glycan has the formula of

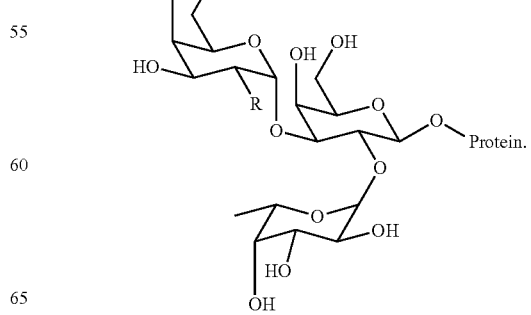

5. The glycan of claim 1, wherein the glycosyltransferase is specific for the fucose-α(1-2)-galactose group.

6. The glycan of claim 1, wherein the glycosyl transferase is a bacteria homologue of the human blood group A antigen glycosyltransferase (BgtA) or a variant or fragment thereof.

7. The glycan of claim 1, wherein the glycosyltransferase is a human blood group A antigen glycosyltransferase or a variant or fragment thereof.

8. A reaction mixture for generating the glycan of claim 4 comprising
1) fucose-α(1-2)-galactose;
2) a labeling agent of the formula:

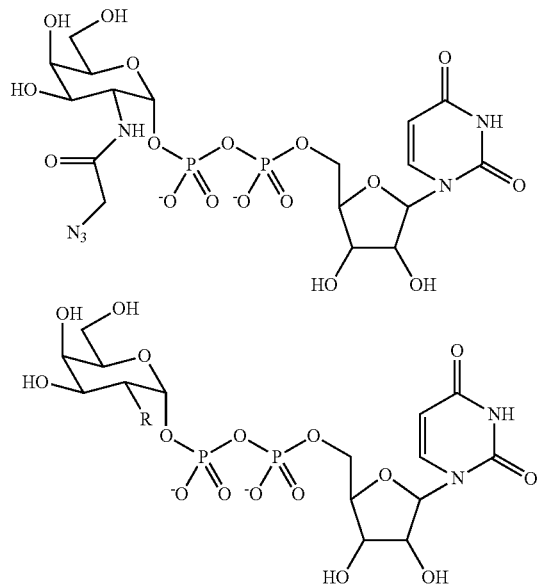

wherein R is a reactive group,
wherein R is a substituent selected from the group consisting of a straight chain or branched $C_1$-$C_{12}$ carbon chain bearing a carbonyl group, an azide group, a straight chain or branched $C_1$-$C_{12}$ carbon chain bearing an azide group, a straight chain or branched $C_1$-$C_{12}$ carbon chain bearing an alkyne, or a straight chain or branched $C_1$-$C_{12}$ carbon chain bearing an alkene;
wherein the labeling agent is recognized by the glycosyltransferase.

9. The mixture of claim 8, wherein the glycan is attached to a glycoprotein or glycolipid.

10. The reaction mixture of claim 8, further comprising a detection agent, and wherein the detection agent is selected from the group consisting of a fluorescent reagent, enzymatic reagent capable of converting substrates calorimetrically or fluorometrically, fluorescent and luminescent probe, metal-binding probe, protein-binding probe, probe for antibody-based binding, radioactive probe, photocaged probe, spin-label, spectroscopic probe, a heavy-atom containing probe, poly(ethylene)glycol-containing probe and poly(propylene)glycol-containing probe.

11. The reaction mixture of claim 8, wherein labeling agent is placed on a solid support.

12. A method for labeling a glycan comprising fucose-α (1-2)-galactose, the method comprising: reacting the fucose-α(1-2)-galactose with a labeling agent in the presence of a glycosyltransferase, wherein the labeling agent is a compound of the formula:

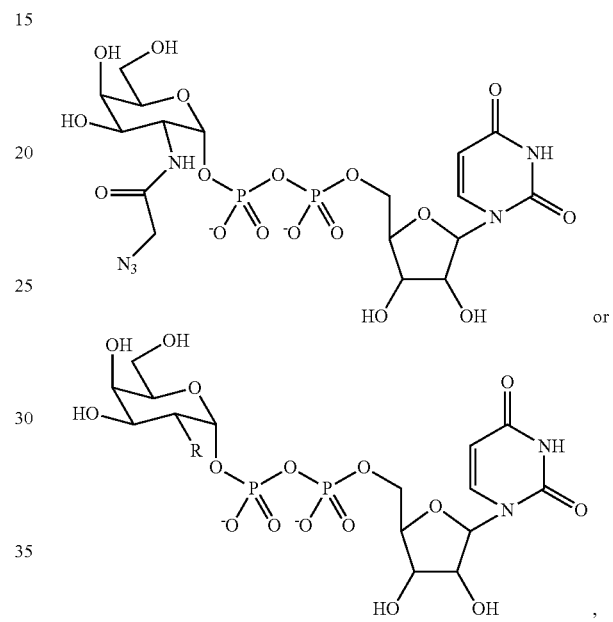

wherein R is a reactive group selected from the group consisting of a straight chain or branched $C_1$-$C_{12}$ carbon chain bearing a carbonyl group, an azide group, a straight chain or branched $C_1$-$C_{12}$ carbon chain bearing an azide group, a straight chain or branched $C_1$-$C_{12}$ carbon chain bearing an alkyne, or a straight chain or branched $C_1$-$C_{12}$ carbon chain bearing an alkene;
wherein the labeling agent is recognized by the glycosyltransferase;
wherein the reactive group is capable of reacting with a detection agent; and
wherein the glycosyltransferase is specific for the glycosyl group labeling agent.

* * * * *

UNITED STATES PATENT AND TRADEMARK OFFICE
CERTIFICATE OF CORRECTION

PATENT NO. : 9,766,245 B2  
APPLICATION NO. : 14/147446  
DATED : September 19, 2017  
INVENTOR(S) : Linda C. Hsieh-Wilson et al.

Page 1 of 1

It is certified that error appears in the above-identified patent and that said Letters Patent is hereby corrected as shown below:

In the Claims

Column 55, Claim 8, Lines 9 and 10:
Replace "the glycan of claim 4 comprising"
With --the glycan of claim 1 comprising--

Column 55, Claim 9, Line 49:
Replace "The mixture of claim 8,"
With --The reaction mixture of claim 8,--

Column 56, Claim 12, Lines 50 and 51:
Replace "is specific for the glycosyl group labeling agent."
With --is specific for the labeling agent.--

Signed and Sealed this
Twenty-first Day of August, 2018

Andrei Iancu
*Director of the United States Patent and Trademark Office*

SEQUENCE LISTING

<160> NUMBER OF SEQ ID NOS: 6

<210> SEQ ID NO 1
<211> LENGTH: 306
<212> TYPE: PRT
<213> ORGANISM: Helicobacter mustelae

<400> SEQUENCE: 1

Met Gln Ser Thr Ala Gln Asn Thr Gln Gln Asn Thr His Phe Ala Gly
1               5                   10                  15

Ser Ser Gln Thr Thr Pro Gln Ala Ala Gln Ser Val Gln Gln Ala Ser
            20                  25                  30

Leu Ala Leu Pro Lys Ser Ser Pro Thr Cys Tyr Lys Ile Ala Ile Leu
        35                  40                  45

Tyr Ile Cys Thr Gly Ala Tyr Ser Ile Phe Trp Gln Asp Phe Tyr Asp
    50                  55                  60

Ser Ala Lys Val His Leu Leu Pro Ala His Arg Leu Thr Tyr Phe Val
65                  70                  75                  80

Phe Thr Asp Ala Asp Ser Leu Tyr Ala Glu Glu Ala Ser Asp Val Arg
                85                  90                  95

Lys Ile Tyr Gln Glu Asn Leu Gly Trp Pro Phe Asn Thr Leu Lys Arg

```
                100              105                   110
Phe Glu Met Phe Leu Gly Gln Glu Glu Ala Leu Arg Glu Phe Asp Phe
            115                 120                 125

Val Phe Phe Phe Asn Ala Asn Cys Leu Phe Phe Gln His Ile Gly Asp
    130                 135                 140

Glu Phe Leu Pro Ile Glu Glu Asp Ile Leu Val Thr Gln His Tyr Gly
145                 150                 155                 160

Phe Arg Asp Ala Ser Pro Glu Cys Phe Thr Tyr Glu Arg Asn Pro Lys
                165                 170                 175

Ser Leu Ala Tyr Val Pro Phe Gly Lys Gly Lys Ala Tyr Val Tyr Gly
            180                 185                 190

Ser Thr Asn Gly Gly Lys Ala Gly Ala Phe Leu Ala Leu Ala Arg Thr
        195                 200                 205

Leu Gln Glu Arg Ile Gln Glu Asp Leu Ser Arg Gly Ile Ile Ala Ile
    210                 215                 220

Trp His Asp Glu Ser His Leu Asn Ala Tyr Ile Ile Asp His Pro Asn
225                 230                 235                 240

Tyr Lys Met Leu Asp Tyr Gly Tyr Gly Phe Pro Glu Gly Tyr Gly Arg
                245                 250                 255

Val Pro Gly Gly Gly Val Tyr Ile Phe Leu Arg Asp Lys Ser Arg Val
            260                 265                 270

Ile Asp Val Asn Ala Ile Lys Gly Met Gly Ser Pro Ala Asn Arg Arg
        275                 280                 285

Leu Lys Asn Ala Leu Arg Lys Leu Lys His Phe Ser Lys Arg Leu Leu
    290                 295                 300

Gly Arg
305

<210> SEQ ID NO 2
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gly Gln Ser Thr Ala Gln Asn Thr Gln Gln Asn Thr His Phe Ala
1               5                   10                  15

Gly Ser Ser Gln Thr Thr Pro Gln Ala Ala Gln Ser Val Gln Gln Ala
            20                  25                  30

Ser Leu Ala Leu Pro Lys Ser Pro Thr Cys Tyr Lys Ile Ala Ile
        35                  40                  45

Leu Tyr Ile Cys Thr Gly Ala Tyr Ser Ile Phe Trp Gln Asp Phe Tyr
    50                  55                  60

Asp Ser Ala Lys Val His Leu Leu Pro Ala His Arg Leu Thr Tyr Phe
65                  70                  75                  80

Val Phe Thr Asp Ala Asp Ser Leu Tyr Ala Glu Ala Ser Asp Val
                85                  90                  95

Arg Lys Ile Tyr Gln Glu Asn Leu Gly Trp Pro Phe Asn Thr Leu Lys
                100                 105                 110

Arg Phe Glu Met Phe Leu Gly Gln Glu Glu Ala Leu Arg Glu Phe Asp
            115                 120                 125

Phe Val Phe Phe Phe Asn Ala Asn Cys Leu Phe Phe Gln His Ile Gly
        130                 135                 140
```

```
Asp Glu Phe Leu Pro Ile Glu Glu Asp Ile Leu Val Thr Gln His Tyr
145                 150                 155                 160

Gly Phe Arg Asp Ala Ser Pro Glu Cys Phe Thr Tyr Glu Arg Asn Pro
                165                 170                 175

Lys Ser Leu Ala Tyr Val Pro Phe Gly Lys Gly Lys Ala Tyr Val Tyr
            180                 185                 190

Gly Ser Thr Asn Gly Gly Lys Ala Gly Ala Phe Leu Ala Leu Ala Arg
        195                 200                 205

Thr Leu Gln Glu Arg Ile Gln Glu Asp Leu Ser Arg Gly Ile Ile Ala
    210                 215                 220

Ile Trp His Asp Glu Ser His Leu Asn Ala Tyr Ile Ile Asp His Pro
225                 230                 235                 240

Asn Tyr Lys Met Leu Asp Tyr Gly Tyr Gly Phe Pro Glu Gly Tyr Gly
                245                 250                 255

Arg Val Pro Gly Gly Val Tyr Ile Phe Leu Arg Asp Lys Ser Arg
            260                 265                 270

Val Ile Asp Val Asn Ala Ile Lys Gly Met Gly Ser Pro Ala Asn Arg
        275                 280                 285

Arg Leu Lys Asn Ala Leu Arg Lys Leu Lys His Phe Ser Lys Arg Leu
    290                 295                 300

Leu Gly Arg Leu Glu His His His His His His
305                 310                 315

<210> SEQ ID NO 3
<211> LENGTH: 354
<212> TYPE: PRT
<213> ORGANISM: Homo sapiens

<400> SEQUENCE: 3

Met Ala Glu Val Leu Arg Thr Leu Ala Gly Lys Pro Lys Cys His Ala
1               5                   10                  15

Leu Arg Pro Met Ile Leu Phe Leu Ile Met Leu Val Leu Val Leu Phe
                20                  25                  30

Gly Tyr Gly Val Leu Ser Pro Arg Ser Leu Met Pro Gly Ser Leu Glu
            35                  40                  45

Arg Gly Phe Cys Met Ala Val Arg Glu Pro Asp His Leu Gln Arg Val
        50                  55                  60

Ser Leu Pro Arg Met Val Tyr Pro Gln Pro Lys Val Leu Thr Pro Cys
65                  70                  75                  80

Arg Lys Asp Val Leu Val Val Thr Pro Trp Leu Ala Pro Ile Val Trp
                85                  90                  95

Glu Gly Thr Phe Asn Ile Asp Ile Leu Asn Glu Gln Phe Arg Leu Gln
            100                 105                 110

Asn Thr Thr Ile Gly Leu Thr Val Phe Ala Ile Lys Lys Tyr Val Ala
        115                 120                 125

Phe Leu Lys Leu Phe Leu Glu Thr Ala Glu Lys His Phe Met Val Gly
    130                 135                 140

His Arg Val His Tyr Tyr Val Phe Thr Asp Gln Pro Ala Ala Val Pro
145                 150                 155                 160

Arg Val Thr Leu Gly Thr Gly Arg Gln Leu Ser Val Leu Glu Val Arg
                165                 170                 175

Ala Tyr Lys Arg Trp Gln Asp Val Ser Met Arg Arg Met Glu Met Ile
            180                 185                 190

Ser Asp Phe Cys Glu Arg Arg Phe Leu Ser Glu Val Asp Tyr Leu Val
        195                 200                 205
```

-continued

Cys Val Asp Val Asp Met Glu Phe Arg Asp His Val Gly Val Glu Ile
                210                 215                 220

Leu Thr Pro Leu Phe Gly Thr Leu His Pro Gly Phe Tyr Gly Ser Ser
225                 230                 235                 240

Arg Glu Ala Phe Thr Tyr Glu Arg Arg Pro Gln Ser Gln Ala Tyr Ile
                245                 250                 255

Pro Lys Asp Glu Gly Asp Phe Tyr Tyr Leu Gly Gly Phe Phe Gly Gly
                260                 265                 270

Ser Val Gln Glu Val Gln Arg Leu Thr Arg Ala Cys His Gln Ala Met
                275                 280                 285

Met Val Asp Gln Ala Asn Gly Ile Glu Ala Val Trp His Asp Glu Ser
                290                 295                 300

His Leu Asn Lys Tyr Leu Leu Arg His Lys Pro Thr Lys Val Leu Ser
305                 310                 315                 320

Pro Glu Tyr Leu Trp Asp Gln Gln Leu Leu Gly Trp Pro Ala Val Leu
                325                 330                 335

Arg Lys Leu Arg Phe Thr Ala Val Pro Lys Asn His Gln Ala Val Arg
                340                 345                 350

Asn Pro

<210> SEQ ID NO 4
<211> LENGTH: 348
<212> TYPE: PRT
<213> ORGANISM: Rattus sp.

<400> SEQUENCE: 4

Met Asp Leu Arg Gly Arg Pro Lys Cys Tyr Ser Leu His Leu Gly Ile
1               5                   10                  15

Leu Pro Phe Ile Val Leu Val Leu Val Phe Phe Gly Tyr Gly Phe Leu
                20                  25                  30

Ser His Lys Ile Gln Glu Phe Arg Asn Pro Gly Gly Glu Thr Cys Met
            35                  40                  45

Ala Thr Arg Gln Thr Asp Val Gln Lys Val Val Ser Val Pro Arg Met
50                  55                  60

Ala Tyr Pro Gln Pro Asn Val Leu Thr Pro Ile Arg Asn Asp Val Leu
65                  70                  75                  80

Val Phe Thr Pro Trp Leu Ala Pro Ile Ile Trp Glu Gly Thr Phe Asn
                85                  90                  95

Ile Asp Ile Leu Asn Glu Gln Phe Lys Leu Gln Asn Thr Thr Ile Gly
            100                 105                 110

Leu Thr Val Phe Ala Ile Lys Lys Tyr Val Val Phe Leu Lys Leu Phe
        115                 120                 125

Leu Glu Thr Ala Glu Gln His Phe Met Val Gly His Lys Val Ile Tyr
    130                 135                 140

Tyr Val Phe Thr Asp Arg Pro Ser Asp Val Pro Gln Val Pro Leu Gly
145                 150                 155                 160

Ala Gly Arg Lys Leu Val Val Leu Thr Val Arg Asn Tyr Thr Arg Trp
                165                 170                 175

Gln Asp Val Ser Met His Arg Met Glu Met Ile Ser Phe Ser Glu
            180                 185                 190

Gln Arg Phe Gln His Glu Val Asp Tyr Leu Val Cys Gly Asp Val Asp
        195                 200                 205

Met Lys Phe Ser Asp His Val Gly Val Glu Ile Leu Ser Ala Leu Phe
    210                 215                 220

Gly Thr Leu His Pro Gly Phe Tyr Arg Ser Arg Arg Glu Ser Phe Thr
225                 230                 235                 240

Tyr Glu Arg Arg Pro Lys Ser Gln Ala Tyr Ile Pro Arg Asp Glu Gly
                245                 250                 255

Asp Phe Tyr Tyr Ala Gly Gly Phe Phe Gly Gly Ser Val Val Glu Val
            260                 265                 270

His His Leu Thr Lys Ala Cys His Gln Ala Met Val Glu Asp Gln Ala
        275                 280                 285

Asn Gly Ile Glu Ala Val Trp His Asp Glu Ser His Leu Asn Lys Tyr
    290                 295                 300

Leu Leu Tyr His Lys Pro Thr Lys Val Leu Ser Pro Glu Tyr Val Trp
305                 310                 315                 320

Asp Gln Lys Leu Leu Gly Trp Pro Ser Ile Met Lys Lys Leu Arg Tyr
                325                 330                 335

Val Ala Val Pro Lys Asn His Gln Ala Ile Arg Asn
                340                 345

<210> SEQ ID NO 5
<211> LENGTH: 332
<212> TYPE: PRT
<213> ORGANISM: Mus sp.

<400> SEQUENCE: 5

Met Asn Leu Arg Gly Arg Pro Lys Cys Asn Phe Leu His Leu Gly Ile
1               5                   10                  15

Leu Pro Phe Ala Val Phe Val Leu Val Phe Phe Gly Tyr Leu Phe Leu
            20                  25                  30

Ser Phe Arg Ser Gln Asn Leu Gly His Pro Gly Ala Val Thr Arg Asn
        35                  40                  45

Ala Tyr Leu Gln Pro Arg Val Leu Lys Pro Thr Arg Lys Asp Val Leu
    50                  55                  60

Val Leu Thr Pro Trp Leu Ala Pro Ile Ile Trp Glu Gly Thr Phe Asn
65                  70                  75                  80

Ile Asp Ile Leu Asn Glu Gln Phe Arg Ile Arg Asn Thr Thr Ile Gly
                85                  90                  95

Leu Thr Val Phe Ala Ile Lys Lys Tyr Val Val Phe Leu Lys Leu Phe
            100                 105                 110

Leu Glu Thr Ala Glu Gln His Phe Met Val Gly His Lys Val Ile Tyr
        115                 120                 125

Tyr Val Phe Thr Asp Arg Pro Ala Asp Val Pro Gln Val Ile Leu Gly
    130                 135                 140

Ala Gly Arg Gln Leu Val Val Leu Thr Val Arg Asn Tyr Thr Arg Trp
145                 150                 155                 160

Gln Asp Val Ser Met His Arg Met Glu Met Ile Ser His Phe Ser Glu
                165                 170                 175

Arg Arg Phe Leu Arg Glu Val Asp Tyr Leu Val Cys Ala Asp Ala Asp
            180                 185                 190

Met Lys Phe Ser Asp His Val Gly Val Glu Ile Leu Ser Thr Phe Phe
        195                 200                 205

Gly Thr Leu His Pro Gly Phe Tyr Ser Ser Arg Glu Ala Phe Thr
    210                 215                 220

Tyr Glu Arg Arg Pro Gln Ser Gln Ala Tyr Ile Pro Trp Asp Arg Gly
225                 230                 235                 240

Asp Phe Tyr Tyr Gly Gly Ala Phe Phe Gly Gly Ser Val Leu Glu Val

```
                    245                 250                 255
Tyr His Leu Thr Lys Ala Cys His Glu Ala Met Met Glu Asp Lys Ala
            260                 265                 270

Asn Gly Ile Glu Pro Val Trp His Asp Glu Ser Tyr Leu Asn Lys Tyr
            275                 280                 285

Leu Leu Tyr His Lys Pro Thr Lys Val Leu Ser Pro Glu Tyr Leu Trp
        290                 295                 300

Asp Gln Gln Leu Leu Gly Trp Pro Ser Ile Met Lys Lys Leu Arg Tyr
305                 310                 315                 320

Val Ala Val Pro Lys Asp His Gln Ala Ile Arg Asn
                325                 330

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 6

His His His His His His
1               5
```